(12) United States Patent
Andrews et al.

(10) Patent No.: US 10,357,509 B2
(45) Date of Patent: Jul. 23, 2019

(54) METHODS AND COMPOSITIONS FOR TREATING CANCERS USING ANTISENSE

(71) Applicant: THOMAS JEFFERSON UNIVERSITY, Philadelphia, PA (US)

(72) Inventors: David W. Andrews, Philadelphia, PA (US); Douglas C. Hooper, Medford, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 15/917,050

(22) Filed: Mar. 9, 2018

(65) Prior Publication Data
US 2018/0201939 A1   Jul. 19, 2018

Related U.S. Application Data

(60) Provisional application No. 62/629,972, filed on Feb. 13, 2018, provisional application No. 62/469,003, filed on Mar. 9, 2017.

(51) Int. Cl.
| | | |
|---|---|---|
| C07H 21/04 | (2006.01) | |
| A61K 31/7105 | (2006.01) | |
| C12N 15/113 | (2010.01) | |
| A61K 31/713 | (2006.01) | |
| A61P 35/00 | (2006.01) | |
| A61K 39/00 | (2006.01) | |
| G01N 33/574 | (2006.01) | |

(52) U.S. Cl.
CPC ........ *A61K 31/7105* (2013.01); *A61K 31/713* (2013.01); *A61K 39/0011* (2013.01); *A61P 35/00* (2018.01); *C12N 15/1138* (2013.01); A61K 2039/545 (2013.01); A61K 2039/55561 (2013.01); A61K 2039/585 (2013.01); C12N 2310/11 (2013.01); C12N 2320/32 (2013.01); G01N 33/57484 (2013.01)

(58) Field of Classification Search
CPC .................................................. C12N 15/113
USPC ........................................................ 536/24.5
See application file for complete search history.

(56) References Cited

U.S. PATENT DOCUMENTS

| | | | |
|---|---|---|---|
| 5,643,788 | A | 7/1997 | Baserga |
| 5,714,170 | A | 2/1998 | Baserga |
| 6,331,526 | B1 | 12/2001 | Baserga et al. |
| 6,541,036 | B1 | 4/2003 | Andrews et al. |
| 2011/0092572 | A1 | 4/2011 | Tachas et al. |
| 2015/0320409 | A1 | 11/2015 | Lehmann et al. |
| 2017/0056065 | A1 | 3/2017 | Do et al. |
| 2017/0056430 | A1 | 3/2017 | Andrews et al. |
| 2018/0235996 | A1 | 8/2018 | Andrews et al. |
| 2018/0256625 | A1 | 9/2018 | Andrews et al. |
| 2018/0271894 | A1 | 9/2018 | Andrews et al. |

FOREIGN PATENT DOCUMENTS

| | | |
|---|---|---|
| CA | 2 447 400 A1 | 3/2005 |
| WO | WO 96/14746 A1 | 5/1996 |
| WO | WO 2016/164916 A1 | 10/2016 |

OTHER PUBLICATIONS

McLaughlin N, Filho LFSD, Prevedello DM, Kelly DF, Carrau RL, Kassam AB. Side-Cutting Aspiration Device for Endoscopic and Microscopic Tumor Removal. Journal of Neurological Surgery Part B, Skull Base. 2012;73(1):11-20. doi:10.1055/s-0032-1304834.*
"Antisense102: Pilot Immunotherapy for Newly Diagnosed Malignant Glioma." ClinicalTrials.gov, NCT02507583, First Received Jun. 29, 2015, Verified Apr. 2016 by Thomas Jefferson University, 4 pages. https://clinicaltrials.gov/ct2/shrm/NCT02507583?term=NCT02507583&rank=1 [downloaded Mar. 18, 2017].
"Pilot Immunotherapy Trial for Recurrent Malignant Gliomas." ClinicalTrials.gov, NCT01550523, Study Completed, First Received Feb. 14, 2012, Verified Dec. 2013 by Thomas Jefferson University, 4 pages. https://clinicaltrials.gov/ct2/show/NCT01550523?term=%22diffusion+chamber%22&rank=2 [downloaded Mar. 18, 2017].
Andrews, D.W., et al., "Phase 1 Trial of Vaccination with Autologous Tumor Cells and Antisense Directed Against the Insulin Growth Factor Type 1 Receptor (IGF-1R AS ODN) in Patients with Recurrent Malignant Glioma." Departments of Neurological Surgery, Thomas Jefferson University, Philadelphia, PA, Feb. 12, 2016, 10 pages.
Andrews, D.W., et al., "Results of a Pilot Study Involving the Use of an Antisense Oligodeoxynucleotide Directed Against the Insulin-Like Growth Factor Type I Receptor in Malignant Astrocytomas." Journal of Clinical Oncology (2001); 19(8): 2189-2200.
Baserga, Renato, et al. "The role of the IGF-I receptor in apoptosis." Vitamins & Hormones (1997); 53: 65-98.
De Vries, M., et al., "Tumor-Associated Macrophages Are Related to Volumetric Growth of Vestibular Schwannomas." Otology & Neurotology (2013); 34(2): 347-352.
Harshyne, L.A., et al., "Glioblastoma exosomes and IGF-1R/AS-ODN are immunogenic stimuli in a translational research immunotherapy paradigm." Cancer Immunol Immunother (2015); 64(3): 299-309.

(Continued)

*Primary Examiner* — Kimberly Chong
(74) *Attorney, Agent, or Firm* — Cozen O'Connor

(57) ABSTRACT

The present disclosure relates to compositions and methods for treating cancers using antisense (AS) nucleic acids directed against Insulin-like Growth Factor 1 Receptor (IGF-1R). The AS may be administered to the patients systemically, or may be used to produce an autologous cancer cell vaccine. In embodiments, the AS are provided in an implantable irradiated biodiffusion chamber comprising tumor cells and an effective amount of the AS. The chambers are irradiated and implanted in the abdomen of subjects and stimulate an immune response that attacks tumors distally. The compositions and methods disclosed herein may be used to treat many different kinds of cancer, for example glioblastoma.

17 Claims, 45 Drawing Sheets
(37 of 45 Drawing Sheet(s) Filed in Color)
Specification includes a Sequence Listing.

(56) References Cited

OTHER PUBLICATIONS

Harshyne, L.A., et al., "Th2 bias in glioblastoma patient peripheral blood." Neuro-Oncology (2016); 18(2): 206-215. (Advance Access Publication Jul. 14, 2015).
International Preliminary Report on Patentability, PCT appl. No. PCT/US2016/026970, dated Oct. 10, 2017, 6 pages.
International Search Report, PCT appl. No. PCT/US2016/026970, 4 pages (dated Jul. 29, 2016).
Jin et al., "Cell surface Nestin is a biomarker for glioma stem cells," Biochem Biophys Res Commun. (2013); 433(4): 496-501.
Kanno, H., et al., "Expression of CD163 prevents apoptosis through the production of granulocyte colony-stimulating factor in meningioma." Neuro-Oncology (2013); 15(7): 853-864. (Advance Access publication Mar. 28, 2013).
Martinez et al., "Transcriptional Profiling of the Human Monocyte-to-Macrophage Differentiation and Polarization: New Molecules and Patterns of Gene Expression," J. Immunol. 177:7303-7311 (2006).
Morin-Brureau, M., et al., "Enhancement of glioma-specific immunity in mice by "NOBEL", an insulin-like growth factor 1 receptor antisense oligodeoxynucleotide." Cancer Immunol Immunother (2015); 64(4): 447-457.
Okwan-Duodu et al., "Obesity-driven inflammation and cancer risk: role of myeloid derived suppressor cells and alternately activated macrophages," Am. J. Cancer Res. 3(1):21-33 (2013).
Prosniak, M., et al., "Glioma Grade Is Associated with the Accumulation and Activity of Cells Bearing M2 Monocyte Markers." Clinical Cancer Research (2013); 19(14): 3776-3786. (Published Online First Jun. 5, 2013).
Stein, David, et al., "The polarity of the dorsoventral axis in the *Drosophila* embryo is defined by an extracellular signal." Cell (1991); 65(5): 725-735.
Written Opinion of the International Searching Authority, PCT appl. No. PCT/US2016/026970, 5 pages (dated Jul. 29, 2016).
Dlouhy et al., "Emerging technology in intracranial neuroendoscopy: application of the NICO Myriad," Neurosurgical Focus, Apr. 2011; 30(4):E6, 9 pages. doi: 10.3171/2011.2.FOCUS10312.
Schillaci, R., et al., "Immunization with Murine Breast Cancer Cells Treated with Antisense Oligodeoxynucleotides to Type I Insulin-Like Growth Factor Receptor Induced an Antitumoral Effect Mediated by a CD8+ Response Involving Fas/Fas Ligand Cytotoxic Pathway." The Journal of Immunology (2006); 176: 3426-3437.
Andrews, D.W., et al., "Phase 1 Trial of Vaccination with Autologous Tumor Cells and Antisense Directed Against the Insulin Growth Factor Type 1 Receptor (IGF-1R AS ODN) in Patients with Recurrent Malignant Glioma," JHN Journal, Winter 2018, vol. 13, Issue 1, Article 2, pp. 7-13.
Resnicoff, Mariana, et al., "The Insulin-like Growth Factor I Receptor Protects Tumor Cells from Apoptosis in Vivo,". Jun. 1995. American Association for Cancer Research. [Retrieved Mar. 15, 2019]. Retrieved from cancerres.aacrjournals.org. pp. 2463-2469.
Weigel, "Controlling Operating Room Temperature and Humidity, and Managing Expectations," Webpage, Dec. 17, 2015 [Retrieved on May 1, 2018]. Retrieved from the Internet: <URL:https://buildingenergy.cx-associates.com/2014/12/controlling-operaling-room-temperature-and-humidity-and-managing-expectations/>, 8 pages.

\* cited by examiner

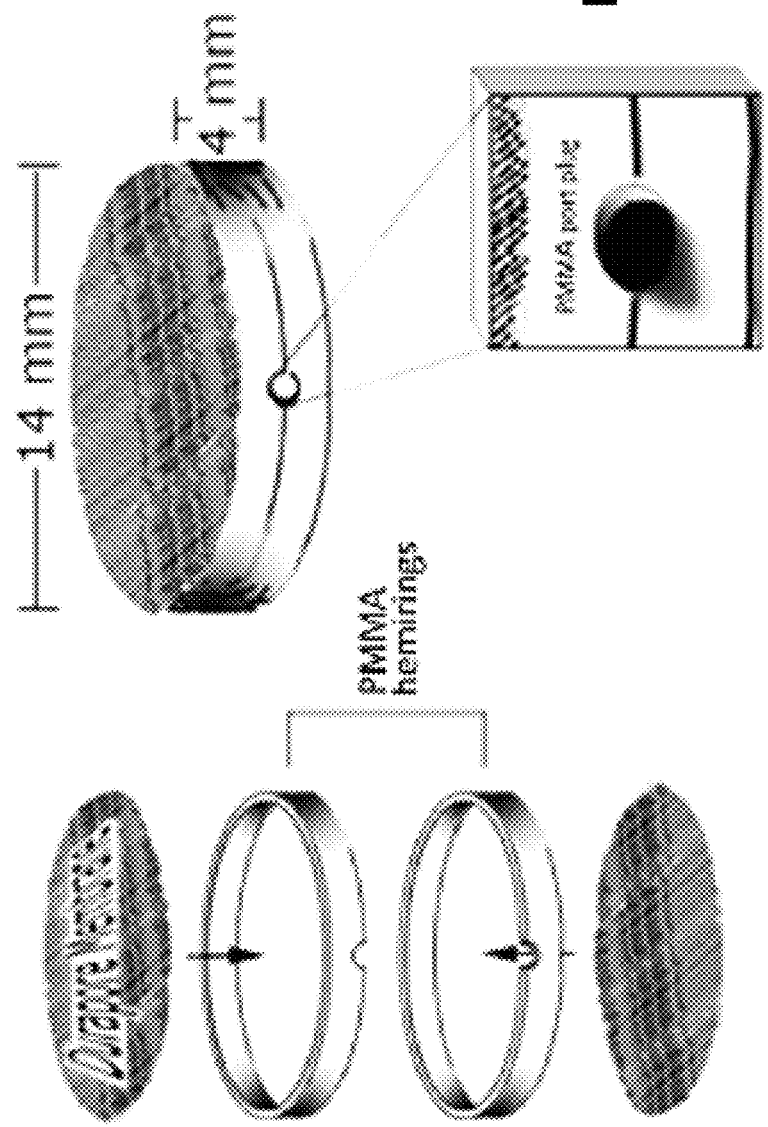

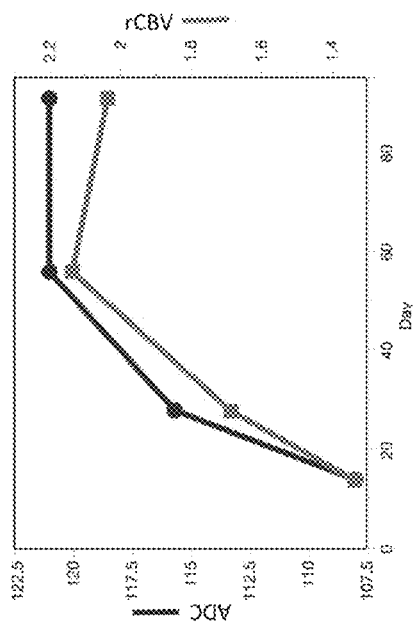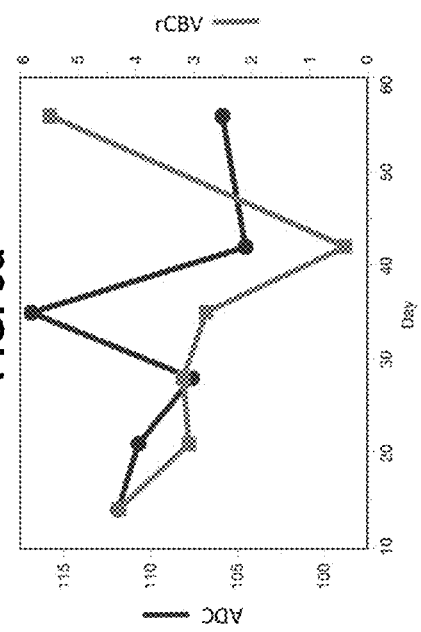

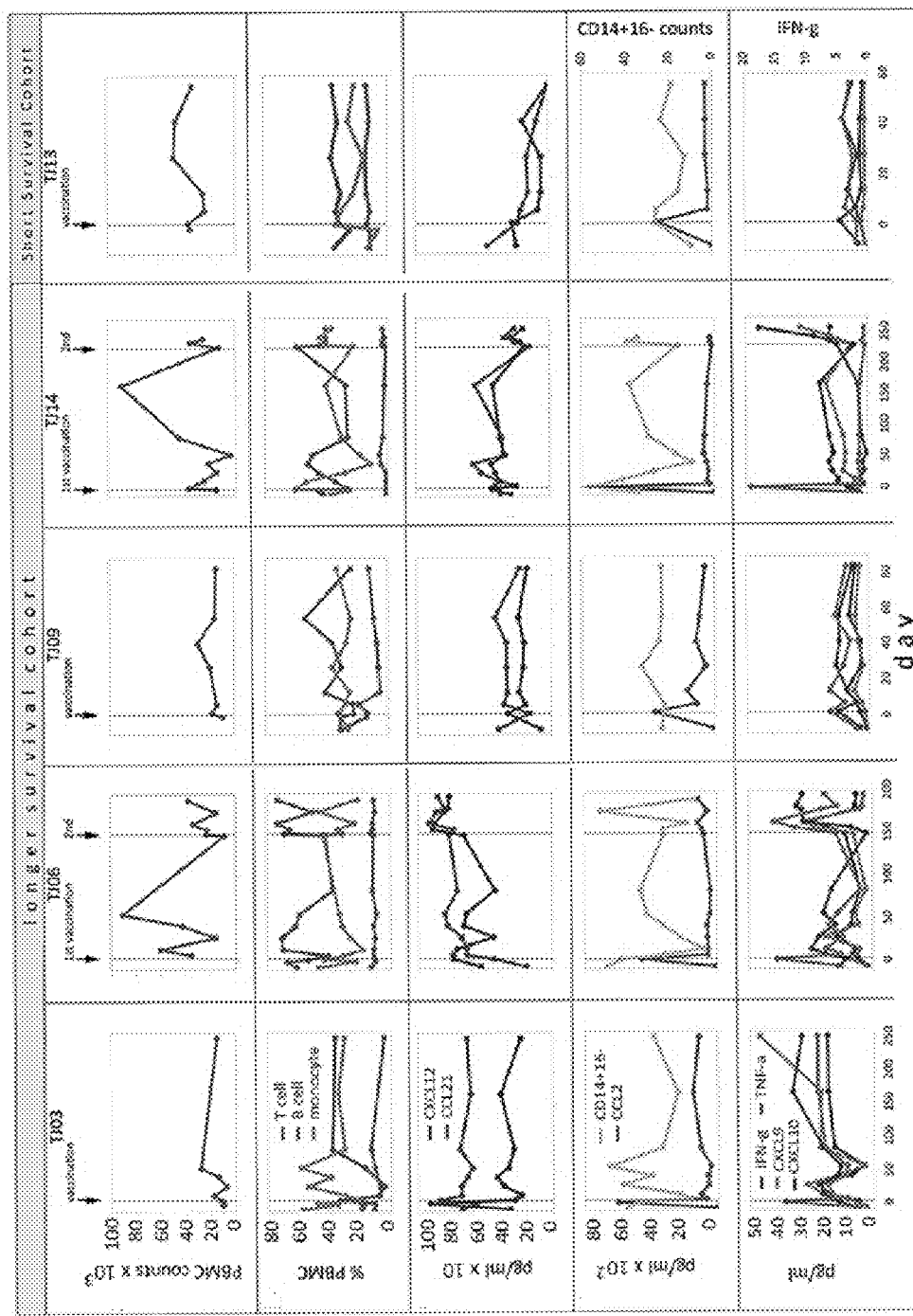

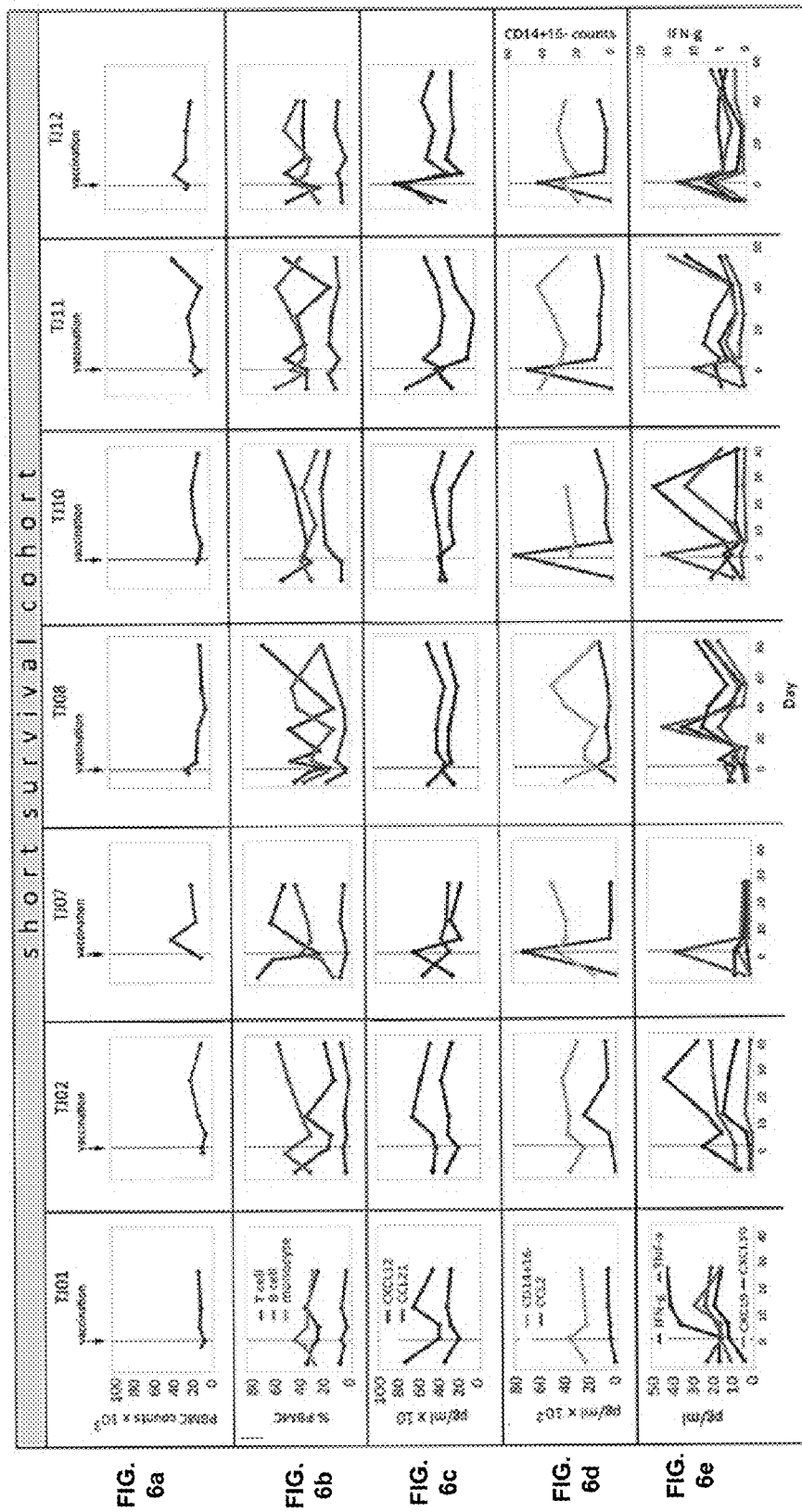

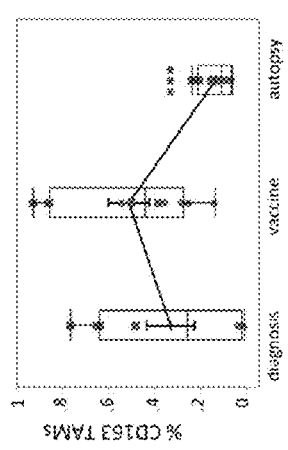
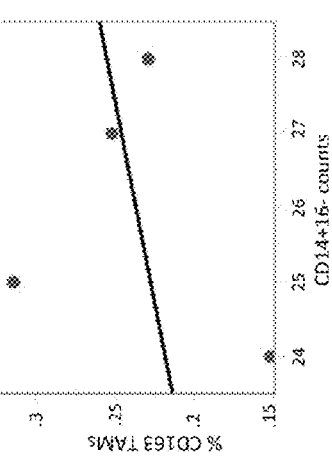
FIG. 7d
FIG. 7e
FIG. 7f weeks

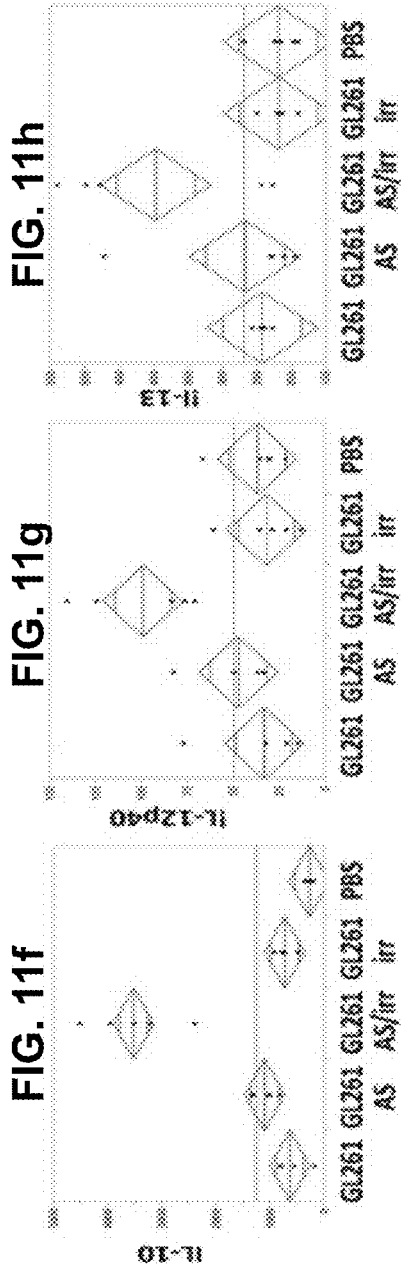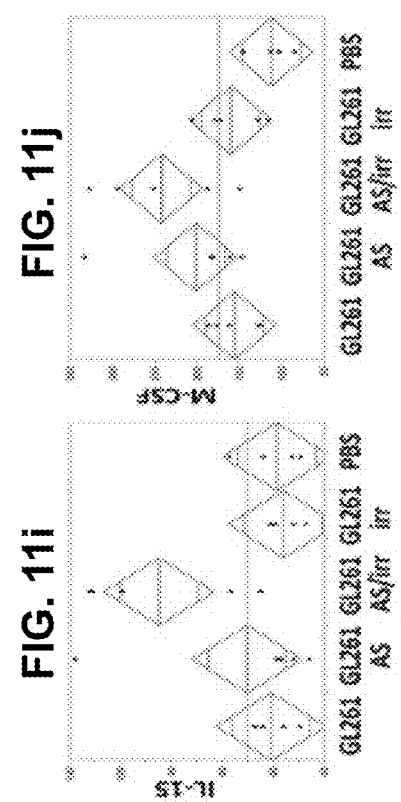

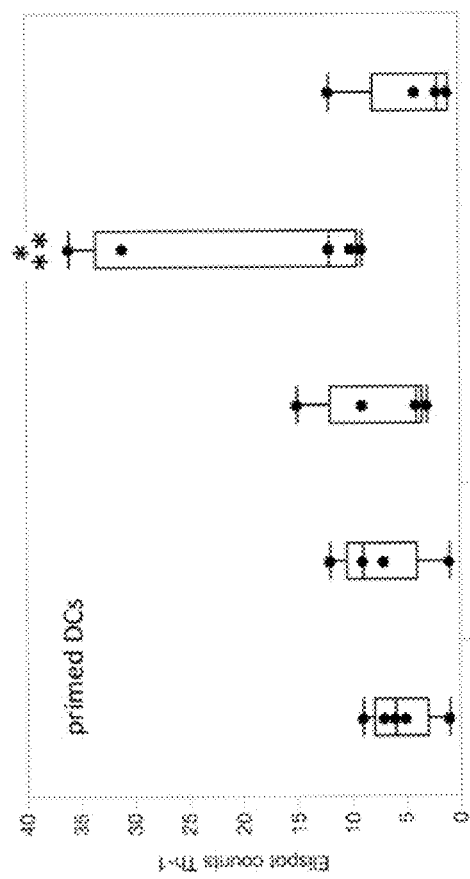
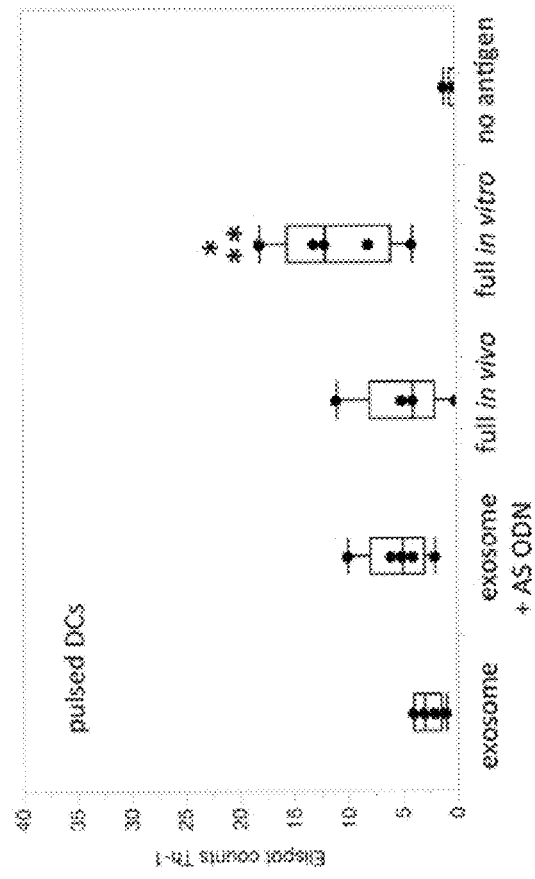
FIG. 13a
FIG. 13b

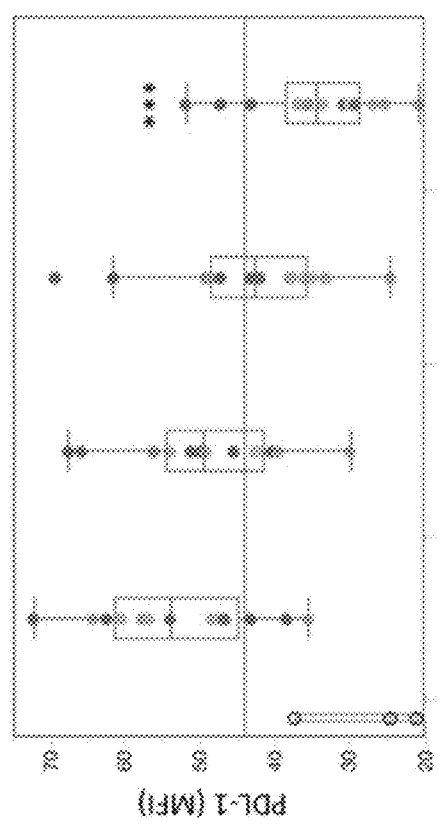
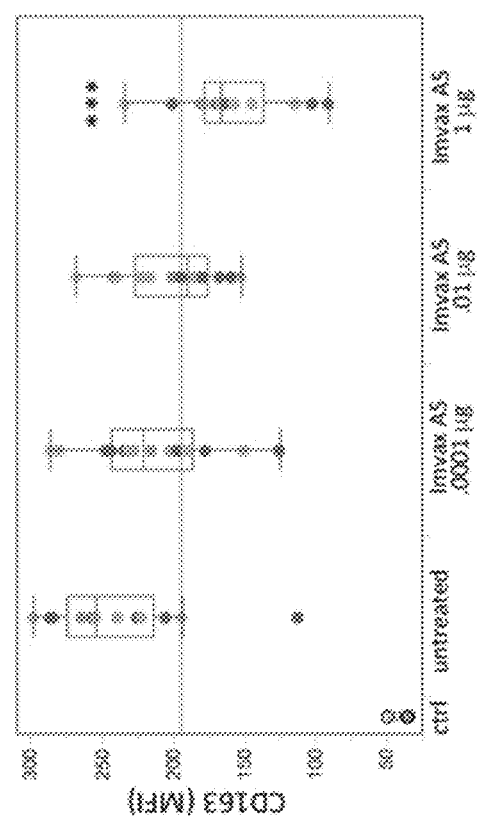
FIG. 15a
FIG. 15b

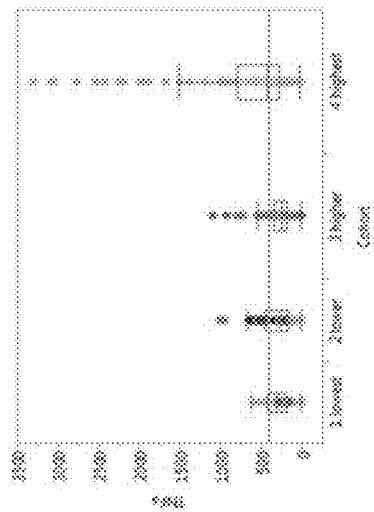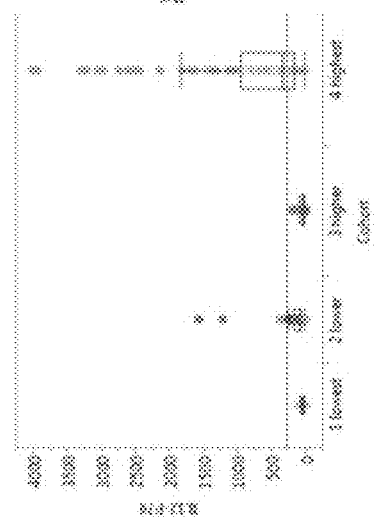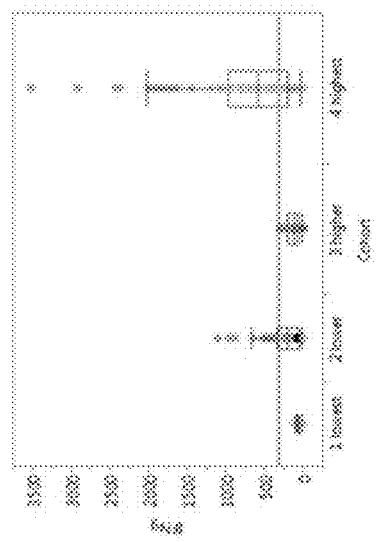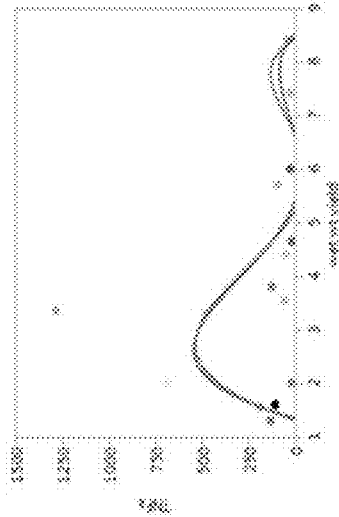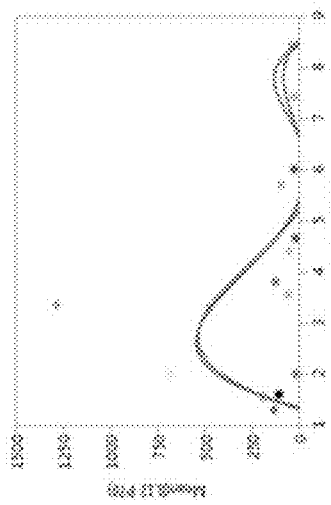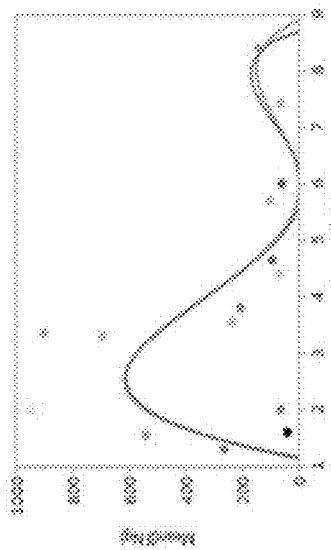

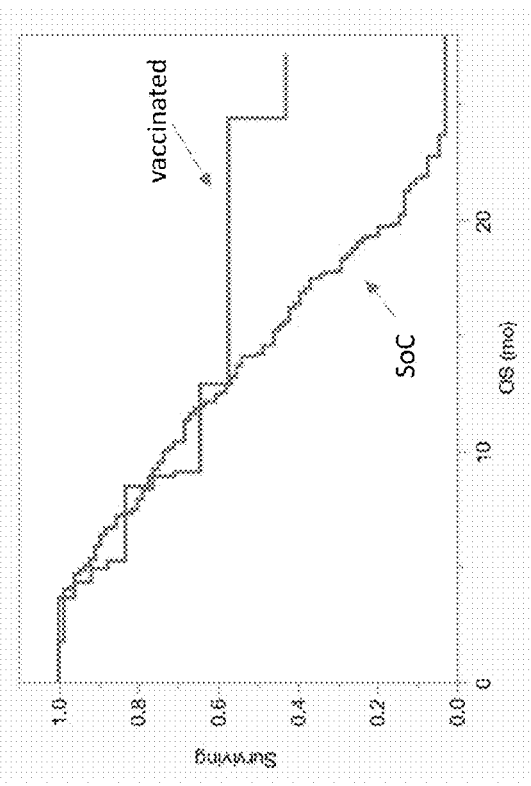
FIG. 24b: Overall survival in Intention to Treat group
Median OS 24.5 v. 14.2 mo, p = .03
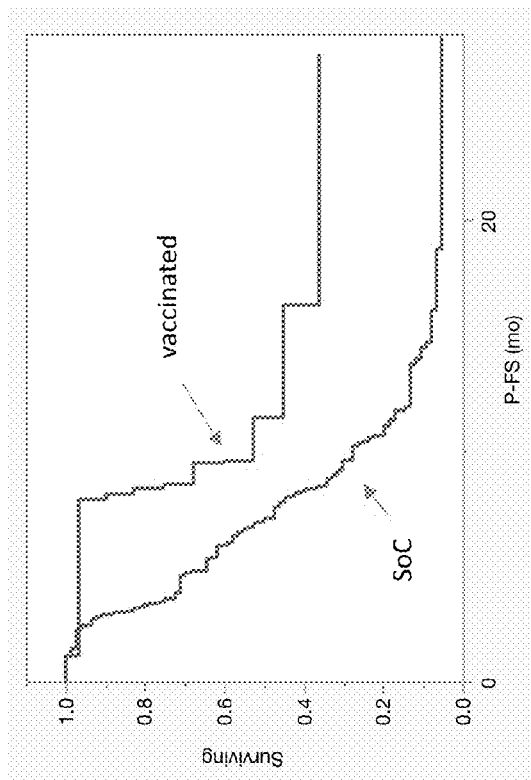
FIG. 24a: Progression Free Survival Intention to Treat group
Median P-FS 11.5 mo v. 7.1 mo, p = .0003
(N = 30 v. TJUH SoC, N = 76)

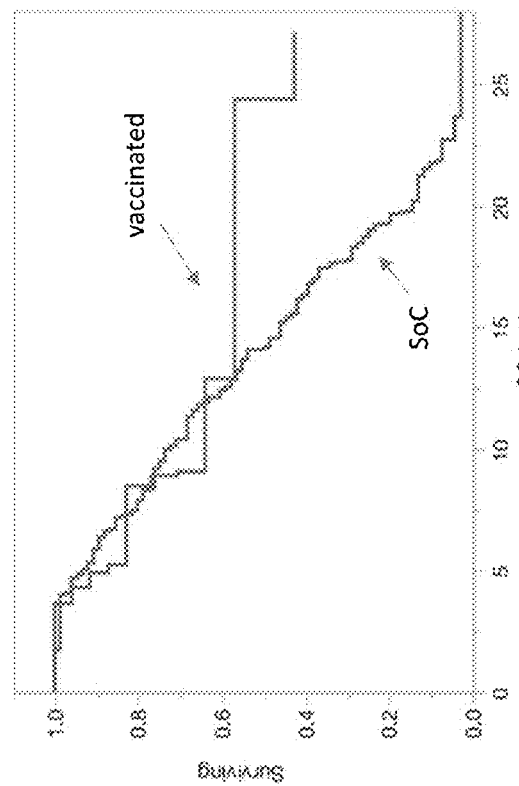
FIG. 25b: Overall survival in Age and Gender-matched Intention to Treat
Median OS 24.5 mo. v. 12.6 mo, p = .01
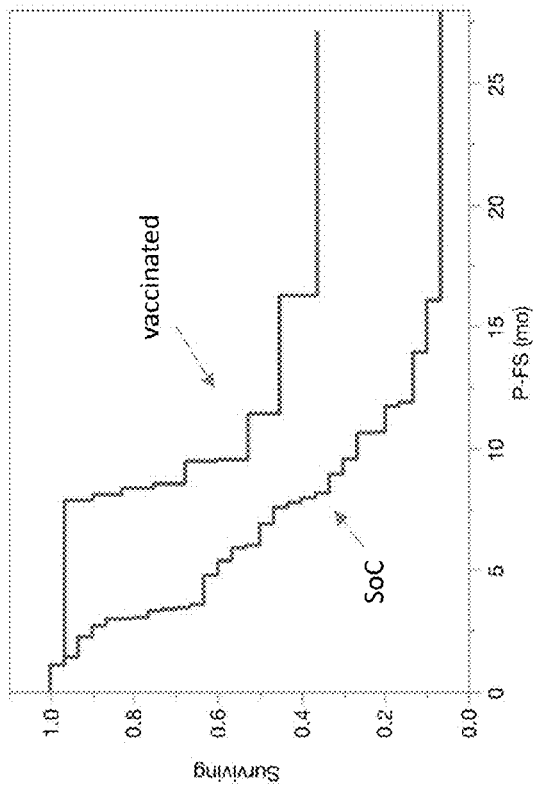
FIG. 25a: Progression Free Age and Gender-matched Intention to Treat
Median P-FS 11.5 mo v. 6.5 mo, p = .0007
(Median age is 61.5 and F/M is 12/18 for both groups)
(N = 30 v. TJUH SOC, N = 30)

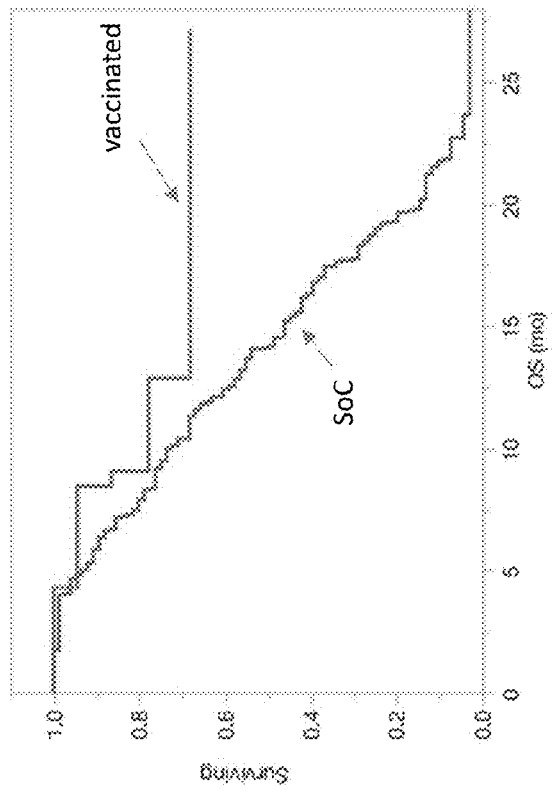
FIG. 26a: Progression-Free survival in patients excluding protocol withdrawals and death from other causes
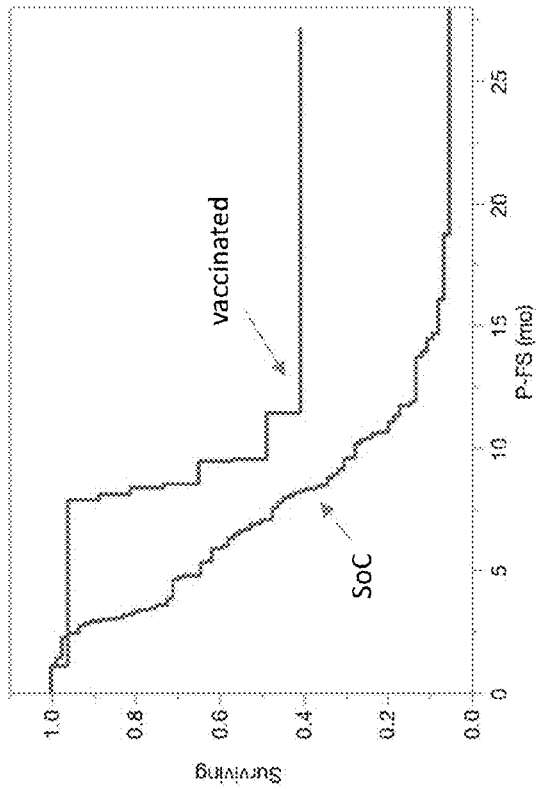
FIG. 26b: Overall survival in patients excluding protocol withdrawals and death from other causes
Median OS NR v. 14.2 mo, p = .0046
Median P-FS 9.6 mo v. 7.1 mo, p = .001
(N = 25) v. TJUH SOC, (N = 76)

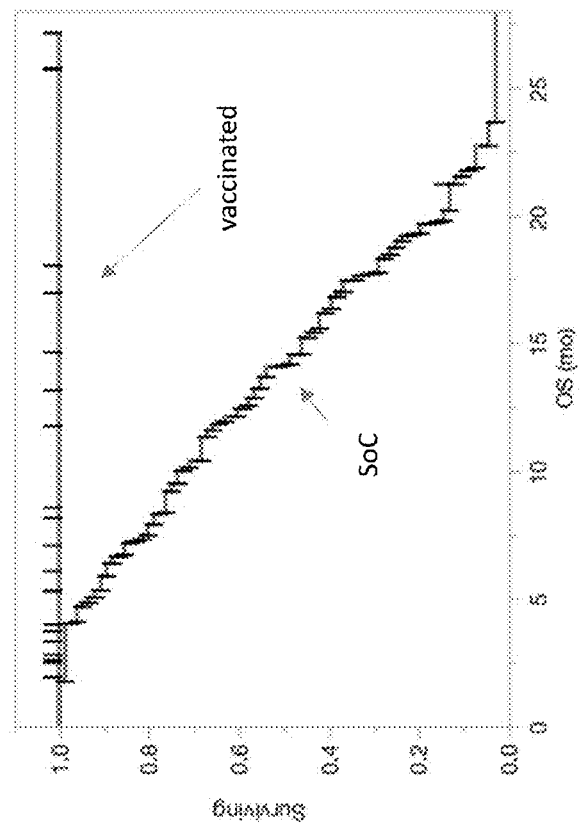
FIG. 27b: Overall survival in patients excluding patients not completing SoC phase of protocol
Median OS NR v. 14.2 mo, p = .0001
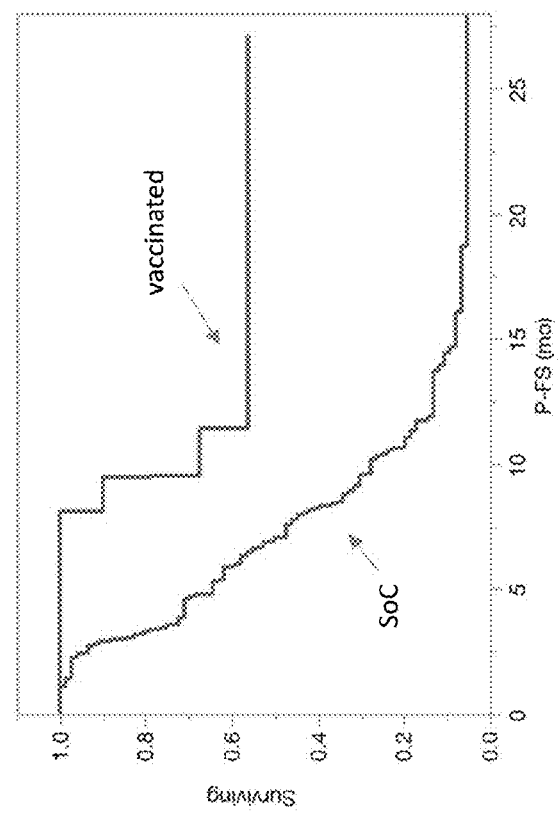
FIG. 27a: Progression-Free survival in patients excluding patients not completing SoC phase of protocol
P-FS NR v. 7.1 mo, p = .0001
(N = 21) v. TJUH SoC (N = 76)

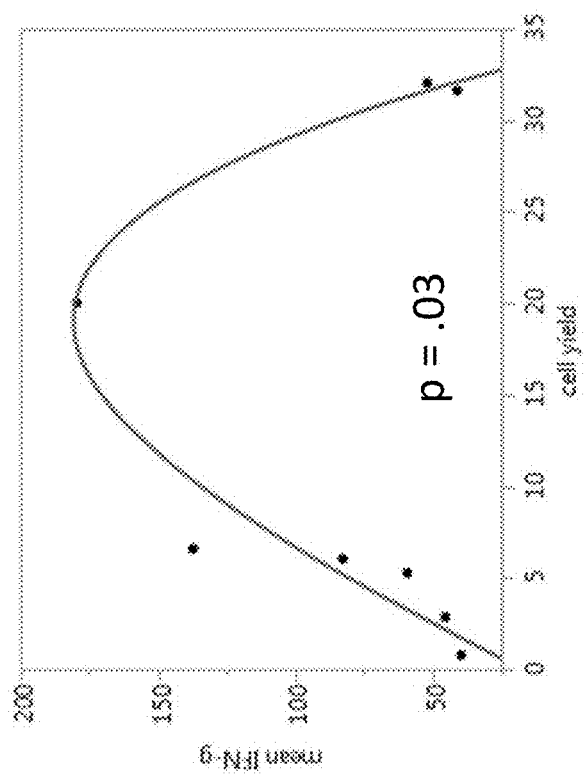
FIG. 28b: mean IFN-g levels
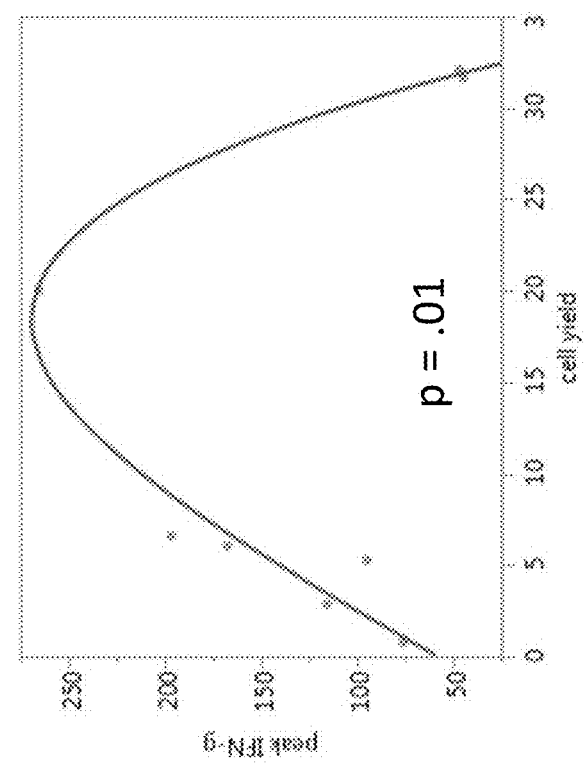
FIG. 28a: Peak IFN-g levels

SEQUENCE LISTING

```
<160> NUMBER OF SEQ ID NOS: 19

<210> SEQ ID NO 1
<211> LENGTH: 18
<212> TYPE: DNA
<213> ORGANISM: Artificial Sequence
<220> FEATURE:
<223> OTHER INFORMATION: NOBEL phosphorothioate AS ODN
<220> FEATURE:
<221> NAME/KEY: misc_feature
<222> LOCATION: (1)..(18)
<223> OTHER INFORMATION: May be joined by a phosphorothioate linkage

<400> SEQUENCE: 1
tcctccggag ccagactt                                                18

<210> SEQ ID NO 2
<211> LENGTH: 17
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 2
ttctccactc gtcggcc                                                 17

<210> SEQ ID NO 3
<211> LENGTH: 18
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 3
acaggccgtg tcgttgtc                                                18

<210> SEQ ID NO 4
<211> LENGTH: 18
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)
```

<400> SEQUENCE: 4
gcactcgccg tcgtggat                                               18

<210> SEQ ID NO 5
<211> LENGTH: 18
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 5
cggatatggt cgttctcc                                               18

<210> SEQ ID NO 6
<211> LENGTH: 18
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 6
tctcagcctc gtggttgc                                               18

<210> SEQ ID NO 7
<211> LENGTH: 18
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 7
ttgcggcctc gttcactg                                               18

<210> SEQ ID NO 8
<211> LENGTH: 18
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 8
aagcttcgtt gagaaact                                               18

<210> SEQ ID NO 9
<211> LENGTH: 18
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 9
ggacttgctc gttggaca                                               18

<210> SEQ ID NO 10
<211> LENGTH: 18
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

```
<400> SEQUENCE: 10
ggctgtctct cgtcgaag                                                 18

<210> SEQ ID NO 11
<211> LENGTH: 20
<212> TYPE: DNA
<213> ORGANISM: Artificial Sequence
<220> FEATURE:
<223> OTHER INFORMATION: IDT1220 phosphorothioate AS ODN
<220> FEATURE:
<221> NAME/KEY: misc_feature
<222> LOCATION: (1)..(20)
<223> OTHER INFORMATION: May be joined by a phosphorothioate linkage

<400> SEQUENCE: 11
cagatttctc cactcgtcgg                                               20

<210> SEQ ID NO 12
<211> LENGTH: 17
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 12
ccggagccag acttcat                                                  17

<210> SEQ ID NO 13
<211> LENGTH: 20
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 13
ctgctcctcc tctaggatga                                               20

<210> SEQ ID NO 14
<211> LENGTH: 15
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 14
ccctcctccg gagcc                                                    15

<210> SEQ ID NO 15
<211> LENGTH: 18
<212> TYPE: DNA
<213> ORGANISM: Artificial Sequence
<220> FEATURE:
<223> OTHER INFORMATION: DWA phosphorothioate AS ODN
<220> FEATURE:
<221> NAME/KEY: misc_feature
<222> LOCATION: (1)..(18)
<223> OTHER INFORMATION: May be joined by a phosphorothioate linkage

<400> SEQUENCE: 15
ggaccctcct ccggagcc                                                 18

<210> SEQ ID NO 16
<211> LENGTH: 18
<212> TYPE: DNA
```

```
<213> ORGANISM: Artificial Sequence
<220> FEATURE:
<223> OTHER INFORMATION: DWA locked nucleic acid AS ODN
<220> FEATURE:
<221> NAME/KEY: misc_feature
<222> LOCATION: (1)..(6)
<223> OTHER INFORMATION: May be joined by a locked nucleic acid linkage
<220> FEATURE:
<221> NAME/KEY: misc_feature
<222> LOCATION: (6)..(13)
<223> OTHER INFORMATION: May be joined by a phosphodiester linkage
<220> FEATURE:
<221> NAME/KEY: misc_feature
<222> LOCATION: (13)..(18)
<223> OTHER INFORMATION: May be joined by a locked nucleic acid linkage

<400> SEQUENCE: 16
ggaccctcct ccggagcc                                                  18

<210> SEQ ID NO 17
<211> LENGTH: 18
<212> TYPE: DNA
<213> ORGANISM: Artificial Sequence
<220> FEATURE:
<223> OTHER INFORMATION: DWA phosphodiester AS ODN
<220> FEATURE:
<221> NAME/KEY: misc_feature
<222> LOCATION: (1)..(18)
<223> OTHER INFORMATION: May be joined by a phosphodiester linkage

<400> SEQUENCE: 17
ggaccctcct ccggagcc                                                  18

<210> SEQ ID NO 18
<211> LENGTH: 927
<212> TYPE: RNA
<213> ORGANISM: Homo sapiens

<400> SEQUENCE: 18 cuuuguuuc uuuucuuccu cacagaccuu cgggcaagga ccuucacaag ggaugcagua      60
caugcucugg cugccguugc ggaugaagcc cgaggggcac uccugcaugc acucgccguc    120
guggaucaca aaccccucgg agucgcugcu cucggcgcug aggauguugg cgcagaaguc    180
acgguccaca cagcgccagc ccucaaaccu guaggguguug ggcgggcagg caggcacaca   240
gacaccggca uaguaguagu ggcggcaagc uacacaggcc gugucguugu caggcgcgcu   300
gcagcugccc aggcacucgg gguggcagca cucauuguuc ucggugcacg cccgcuuccc   360
acacgugcuu gggcacauuu ucuggcagcg guuugugguc cagcagcggu aguuguacuc   420
auuguugaug guggucuucu cacacaucgg cuucuccucc augguccug gacacagguc    480 cccacauucc uuuggggcu uauucccac aaguguaguua uuggacaccg cauccaggau    540
cagggaccag uccacagugg agagguaaca gaggucagca uuuuucacaa uccugauggc   600
cccccgagua auguuccuca gguuguaaag cccaauaucc uugagauugg ucaucucgaa   660 gauugaccagg gcguaguugu agaagaguuu ccagccgcgg augaccguga gguuggggaa  720
gaggucuccg aggcucucga ggccagccac ucggaacagc agcaaguacu cgguaaugac   780
cgugagcuug gggaagcggu agcugcggua guccucggcc uuggagauga gcaggaugug   840
gagguagccc ucgaucaccg ugcaguucuc caggcgcuuc agcugcugau agucguugcg   900
gaugucgaug ccuggcccgc agauuuc                                       927

<210> SEQ ID NO 19
<211> LENGTH: 4104
```

<212> TYPE: DNA
<213> ORGANISM: Homo sapiens

<400> SEQUENCE: 19

| | | | | | |
|---|---|---|---|---|---|
| atgaagtctg | gctccggagg | agggtccccg | acctcgctgt | gggggctcct | gtttctctcc | 60 |
| gccgcgctct | cgctctggcc | gacgagtgga | gaaatctgcg | ggccaggcat | cgacatccgc | 120 |
| aacgactatc | agcagctgaa | gcgcctggag | aactgcacgg | tgatcgaggg | ctacctccac | 180 |
| atcctgctca | tctccaaggc | cgaggactac | cgcagctacc | gcttcccaa | gctcacggtc | 240 |
| attaccgagt | acttgctgct | gttccgagtg | gctggcctcg | agagcctcgg | agacctcttc | 300 |
| cccaacctca | cggtcatccg | cggctggaaa | ctcttctaca | actacgccct | ggtcatcttc | 360 |
| gagatgacca | atctcaagga | tattgggctt | tacaacctga | ggaacattac | tcgggggcc | 420 |
| atcaggattg | agaaaaatgc | tgacctctgt | tacctctcca | ctgtggactg | gtccctgatc | 480 |
| ctggatgcgg | tgtccaataa | ctacattgtg | gggaataagc | ccccaaagga | atgtggggac | 540 |
| ctgtgtccag | ggaccatgga | ggagaagccg | atgtgtgaga | agaccaccat | caacaatgag | 600 |
| tacaactacc | gctgctggac | cacaaaccgc | tgccagaaaa | tgtgcccaag | cacgtgtggg | 660 |
| aagcgggcgt | gcaccgagaa | caatgagtgc | tgccaccccg | agtgcctggg | cagctgcagc | 720 |
| gcgcctgaca | acgacacggc | ctgtgtagct | tgccgccact | actactatgc | cggtgtctgt | 780 |
| gtgcctgcct | gcccgcccaa | cacctacagg | tttgagggct | ggcgctgtgt | ggaccgtgac | 840 |
| ttctgcgcca | acatcctcag | cgccgagagc | agcgactccg | aggggtttgt | gatccacgac | 900 |
| ggcgagtgca | tgcaggagtg | cccctcgggc | ttcatccgca | acggcagcca | gagcatgtac | 960 |
| tgcatccctt | gtgaaggtcc | ttgcccgaag | gtctgtgagg | aagaaaagaa | aacaaagacc | 1020 |
| attgattctg | ttacttctgc | tcagatgctc | caaggatgca | ccatcttcaa | gggcaatttg | 1080 |
| ctcattaaca | tccgacgggg | gaataacatt | gcttcagagc | tggagaactt | catggggctc | 1140 |
| atcgaggtgg | tgacgggcta | cgtgaagatc | cgccattctc | atgccttggt | ctccttgtcc | 1200 |
| ttcctaaaaa | accttcgcct | catcctagga | gaggagcagc | tagaagggaa | ttactccttc | 1260 |
| tacgtcctcg | acaaccagaa | cttgcagcaa | ctgtgggact | gggaccaccg | caacctgacc | 1320 |
| atcaaagcag | ggaaaatgta | ctttgctttc | aatcccaaat | atgtgtttc | cgaaatttac | 1380 |
| cgcatggagg | aagtgacggg | gactaaaggg | cgccaaagca | aggggacat | aaacaccagg | 1440 |
| aacaacgggg | agagagcctc | ctgtgaaagt | gacgtcctgc | atttcacctc | caccaccacg | 1500 |
| tcgaagaatc | gcatcatcat | aacctggcac | cggtaccggc | cccctgacta | cagggatctc | 1560 |
| atcagcttca | ccgtttacta | caaggaagca | ccctttaaga | atgtcacaga | gtatgatggg | 1620 |
| caggatgcct | gcggctccaa | cagctggaac | atggtggacg | tggacctccc | gcccaacaag | 1680 |
| gacgtggagc | ccggcatctt | actacatggg | ctgaagcct | ggactcagta | cgccgtttac | 1740 |
| gtcaaggctg | tgaccctcac | catggtggag | aacgaccata | tccgtggggc | caagagtgag | 1800 |
| atcttgtaca | ttcgcaccaa | tgcttcagtt | ccttccattc | ccttggacgt | tctttcagca | 1860 |
| tcgaactcct | cttctcagtt | aatcgtgaag | tggaaccctc | cctctctgcc | caacggcaac | 1920 |
| ctgagttact | acattgtgcg | ctggcagcgg | cagcctcagg | acggctacct | ttaccggcac | 1980 |
| aattactgct | ccaaagacaa | aatccccatc | aggaagtatg | ccgacggcac | catcgacatt | 2040 |
| gaggaggtca | cagagaaccc | caagactgag | gtgtgtggtg | gggagaaagg | gccttgctgc | 2100 |
| gcctgcccca | aaactgaagc | cgagaagcag | gccgagaagg | aggaggctga | ataccgcaaa | 2160 |
| gtctttgaga | atttcctgca | caactccatc | ttcgtgccca | gacctgaaag | gaagcgggaga | 2220 |

```
gatgtcatgc aagtggccaa caccaccatg tccagccgaa gcaggaacac cacggccgca    2280
gacacctaca acatcaccga cccggaagag ctggagacag agtacccttt ctttgagagc    2340
agagtggata acaaggagag aactgtcatt tctaaccttc ggcctttcac attgtaccgc    2400
atcgatatcc acagctgcaa ccacgaggct gagaagctgg gctgcagcgc ctccaacttc    2460
gtctttgcaa ggactatgcc cgcagaagga gcagatgaca ttcctgggcc agtgacctgg    2520
gagccaaggc ctgaaaactc catcttttta aagtggccgg aacctgagaa tcccaatgga    2580
ttgattctaa tgtatgaaat aaaatacgga tcacaagttg aggatcagcg agaatgtgtg    2640
tccagacagg aatacaggaa gtatggaggg gccaagctaa accggctaaa cccgggggaac   2700 tacacagccc ggattcaggc cacatctctc tctgggaatg ggtcgtggac agatcctgtg    2760
ttcttctatg tccaggccaa aacaggatat gaaaacttca tccatctgat catcgctctg    2820
cccgtcgctg tcctgttgat cgtgggaggg ttggtgatta tgctgtacgt cttccataga    2880
aagagaaata acagcaggct ggggaatgga gtgctgtatg cctctgtgaa cccggagtac    2940
ttcagcgctg ctgatgtgta cgttcctgat gagtgggagg tggctcggga gaagatcacc    3000
atgagccggg aacttgggca ggggtcgttt gggatggtct atgaaggagt tgccaagggt    3060
gtggtgaaag atgaacctga aaccagagtg gccattaaaa cagtgaacga ggccgcaagc    3120
atgcgtgaga ggattgagtt tctcaacgaa gcttctgtga tgaaggagtt caattgtcac    3180
catgtggtgc gattgctggg tgtggtgtcc caaggccagc caacactggt catcatggaa    3240
ctgatgacac ggggcgatct caaaagttat ctccggtctc tgaggccaga aatggagaat    3300
aatccagtcc tagcacctcc aagcctgagc aagatgattc agatggccgg agagattgca    3360
gacggcatgg catacctcaa cgccaataag ttcgtccaca gagaccttgc tgcccggaat    3420
tgcatggtag ccgaagattt cacagtcaaa atcggagatt ttggtatgac gcagatatc    3480 tatgagacag actattaccg gaaaggaggg aaagggctgc tgcccgtgcg ctggatgtct    3540
cctgagtccc tcaaggatgg agtcttcacc acttactcgg acgtctggtc cttcggggtc    3600
gtcctctggg agatcgccac actggccgag cagccctacc agggcttgtc caacgagcaa    3660
gtccttcgct tcgtcatgga gggcggcctt ctggacaagc cagacaactg tcctgacatg    3720
ctgtttgaac tgatgcgcat gtgctggcag tataaccccca agatgaggcc ttccttcctg    3780
gagatcatca gcagcatcaa agaggagatg gagcctggct tccgggaggt ctccttctac    3840
tacagcgagg agaacaagct gcccgagccg gaggagctgg aacctggagcc agagaacatg    3900 gagagcgtcc ccctggaccc ctcggcctcc tcgtcctccc tgccactgcc cgacagacac    3960
tcaggacaca aggccgagaa cggccccggc cctggggtgc tggtcctccg cgccagcttc    4020
gacgagagac agccttacgc ccacatgaac gggggccgca agaacgagcg ggccttgccg    4080
ctgccccagt cttcgacctg ctga                                          4104
```

METHODS AND COMPOSITIONS FOR TREATING CANCERS USING ANTISENSE

CROSS-REFERENCE TO RELATED APPLICATIONS

This application claims priority to U.S. Provisional Patent Application Nos. 62/469,003 filed on Mar. 9, 2017, and 62/629,972, filed on Feb. 13, 2018, each entitled "Methods and Compositions for Treating Cancers Using Antisense," the disclosure of each of which is hereby incorporated by reference in its entirety.

FIELD OF THE INVENTION

The present disclosure relates to compositions and methods for treating cancers using antisense nucleic acids directed against Insulin-like Growth Factor-1 Receptor (IGF-1R). The present disclosure also relates to compositions and methods for treating cancers by treating subjects with at least one implantable irradiated biodiffusion chamber (see U.S. Pat. No. 6,541,036 and PCT/US2016/026970, which are incorporated herein by reference in their entireties) comprising tumor cells and an antisense nucleic acid directed against IGF-1R.

DESCRIPTION OF THE TEXT FILE SUBMITTED ELECTRONICALLY

The contents of the text file submitted electronically herewith are incorporated by reference in their entirety: a computer readable format copy of the Sequence Listing (filename: IMVX_005_03US_SeqList.txt, date recorded Mar. 8, 2018, file size 12 kilobytes).

BACKGROUND

Despite advances in cancer therapy, the prognosis for malignant glioma, particularly glioblastoma multiforme, and many other cancers remains poor. Modifications of standard treatments such as, for example, chemotherapy, external beam radiation, and brachytherapy provide only small increments of improvement in both progression-free survival and overall survival. Immunotherapy trials, although promising in theory, have not addressed the challenges created by solid tumors. For the treatment of glioma, the National Cancer Institute estimates an annual incidence of around 28,000 cases annually which increases to over 50,000 if patients with recurrent gliomas are included. Therefore, there is a need in the art to obtain new and improved treatments for cancers, and cancers of the brain in particular.

SUMMARY OF THE INVENTION

The present disclosure demonstrates that an antisense oligodeoxynucleotide (AS-ODN) targeting the insulin-like growth factor receptor-1 (IGF-1R) effectively stimulates a response in a subject that treats cancer when used in the therapeutic approaches described herein. In particular aspects, methods are effective for treating cancer in a patient as part of an autologous cancer cell vaccine alone or, optionally, along with systemic administration. In preferred approaches, the methods disclosed herein provide effective cancer therapy as a monotherapy; i.e. in the absence of chemotherapy and in the absence of radiation therapy.

In embodiments, the present disclosure provides a biodiffusion chamber for implantation into a subject suffering from a tumor, the biodiffusion chamber comprising irradiated tumor cells and irradiated insulin-like growth factor receptor-1 antisense oligodeoxynucleotide (IGF-1R AS ODN). In embodiments, the tumor cells are removed from a resection site of the subject.

In embodiments, the present disclosure provides a diffusion chamber comprising irradiated IGF-1R AS ODN and irradiated, adhesion-enriched, morselized tumor cells; wherein the biodiffusion chamber comprises a membrane that is impermeable to the cells and permeable to the IGF-1R AS ODN.

In embodiments, the tumor cells are removed from the resection site using an endoscopic device. In further embodiments, the tumor cells are removed from the resection site using a tissue morselator. In other embodiments, the tissue morselator comprises a high-speed reciprocating inner cannula within a stationary outer cannula. The outer cannula may comprise a side aperture, and further wherein the tumor cells are drawn into the side aperture by electronically controlled variable suction. In embodiments, the tissue morselator does not produce heat at the resection site. In still further embodiments, the tumor cells are enriched for nestin expression before they are placed into the biodiffusion chamber. In some embodiments, implantation of the chamber inhibits regrowth of the tumor in the subject. In some embodiments, implantation of the chamber inhibits regrowth of the tumor for at least 3 months, at least 6 months, at least 12 months, or at least 36 months.

In additional embodiments, the present disclosure provides a method for preparing a biodiffusion chamber for implantation into a subject suffering from a tumor, the method comprising placing tumor cells into the biodiffusion chamber in the presence of an IGF-1R AS ODN, and irradiating the biodiffusion chamber, wherein the tumor cells are removed from a resection site in the subject using a tissue morselator that does not produce heat at the resection site. Typically, multiple chambers are used. For example, about 10 chambers, or about 20 chambers. Advantageously, an optimal anti-tumor response is obtained when the number of cells in the chamber is about 750,000 to about 1,250,000; for example about 1,000,000 per chamber where 20 chambers are implanted.

In some embodiments, the tissue morselator is an endoscopic device. In further embodiments, the tissue morselator comprises a high-speed reciprocating inner cannula within a stationary outer cannula. In additional embodiments, the outer cannula comprises a side aperture, and the tumor cells are drawn into the side aperture by electronically controlled variable suction.

In embodiments, the present disclosure provides a method of treating a subject suffering from a tumor, the method comprising implanting one or more biodiffusion chambers into the subject, wherein the one or more biodiffusion chambers comprise irradiated tumor cells, and irradiated insulin-like growth factor receptor-1 antisense oligodeoxynucleotide (IGF-1R AS ODN), wherein the tumor cells are removed from a resection site in the subject using a tissue morselator that does not produce heat at the resection site.

BRIEF DESCRIPTION OF THE DRAWINGS

The patent application file contains at least one drawing executed in color. Copies of this patent application publication with color drawing(s) will be provided by the Office upon request and payment of the necessary fee.

FIGS. 1a-1g depict a representative biodiffusion chamber. FIG. 1a. component parts; FIG. 1b. assembled chamber;

FIG. 1c. PMMA port plug to seal the chamber; FIG. 1d. photomicrograph of polyvinylidine fluoride Durapore membrane; FIG. 1e. overhead and lateral view of the actual chamber; FIG. 1f. and FIG. 1g. H & E stained paraffin sections of Durapore membranes after explantation; FIG. 1f. explanted phosphate buffered saline control chamber from human trial 14379-101; FIG. 1g. explanted vaccine chamber from human trial 14379-101.

FIG. 2a. Overall survival of patients in trial; FIG. 2b. protocol survival with two survival cohorts. Nine patients died of disease progression while one died of intracerebral hemorrhage and two of sepsis. Overall protocol survival was 48.2 weeks and 9.2 weeks, respectively for longer (N=4) and shorter (N=8) survival cohorts (log-rank=0.014). FIG. 2c. Excluding one profoundly lymphopenic outlier and three non-disease-related deaths linear regression revealed high correlation between protocol survival and lymphocyte count at enrollment ($R^2=0.8$, p=0.0028).

FIGS. 3a-3d shows radiographic responses with associated physiologic measurements. FIG. 3a. Examples of patient imaging from short survival cohort. Patient TJ11: A-D; Patient TJ10: E-H. A, E: pre-operative T1-gadolinium-enhanced axial images; G: T1-gadolinium-enhanced coronal image; C: pre-operative axial FLAIR image. B, D, F, H: respective 3 month post-operative images. FIG. 3b. Examples of patient imaging from longer survival cohort. Patient TJ06: A-D; Patient TJ09: E-H. A, E: pre-operative T1-gadolinium-enhanced axial images; C, F: pre-operative axial FLAIR images. B, D, F, H: respective 3 month post-operative images. FIG. 3c. Relationship between relative cerebral blood volume in tumor v. apparent diffusion coefficient in longer survival cohort; there is a high correlation between the ADC and rCBV ($R^2=0.96$, p=0.0005). FIG. 3d. Relationship between relative cerebral blood volume in tumor v. apparent diffusion coefficient in short survival cohort.

FIG. 4a. Explanted chambers were structurally intact with no viable cells. Outer surfaces of membranes from both C-p and C-v chambers were coated with CD15+ and CD163+ cells, with dramatically increased numbers on C-v membranes; FIG. 4b. analysis of factors in chambers between survival cohorts revealed significant chamber elevations of VEGF, PDGF-a, IL-11, CCL5, MCP-3 and MIP-1d in the longer cohort while a number of soluble cancer markers were significantly elevated in the short cohort including NSE, osteonectin, and YKL40. Mixture discriminant analysis independently identified these cohort differences; FIG. 4c. for both cohorts, two chemokines associated with glioma macrophage recruitment were significantly lower in C-v than other measurable sources. Both Periostin and CCL2 levels were significantly lower than serum or SN (tumor cell supernatant) values, suggesting elimination of cells producing these chemokines in the chambers.

FIGS. 5a-5e depict post-vaccination levels of PBMCs and cytokines. Serial measurements of immune effector cell shifts and cytokine/chemokine shifts after vaccination in the post-treatment period; longer survival cohort, (patients TJ03, TJ14, TJ06, TJ09); example of short survival cohort, patient TJ13 (for all other short survival cohorts, see FIG. 6). Rows: FIG. 5a. serial PBMC counts after vaccination; FIG. 5b. serial assessments of PBMC subpopulation percentages after vaccination, FIG. 5c. serial levels of CCL21 and CXCL12; FIG. 5d. relationship of absolute CD14+CD16− macrophage counts with MCP-1 (CCL2); note correlation with macrophage levels in FIG. 5b. and CCL2 spike post-operatively. CC12 levels remained significantly higher in the short survival cohort (see FIG. 6); FIG. 5e. scaled comparisons of putative TH-1 cytokine responses after vaccinations (TNF-α×2; CXCL9×350; CXCL10×80). Significant correlations were noted as follows: TNF-α spikes were highly correlated with CCL2 spikes for both cohorts ($R^2=0.99$, p=0.003). There was a significant immediate perioperative decrease in CD14+16− cells (p=0.008) not seen in the short cohort (p=0.78). For the longer cohort only, there was a significant correlation between CD4 and CXCL12 ($R^2=0.62$, p<0.0001). Also, a high correlation was noted between total monocyte count and CD14+16− monocyte levels (FIGS. 5B and 5D, $R^2=0.8$, p<0.0001) and inverse relationships between circulating T cell and monocyte numbers ($R^2=0.66$, p<0.0001) were noted in the longer survival cohort (FIG. 5) without significant differences in the short survival cohort (see FIG. 6).

FIGS. 6a-6e depicts post-vaccination levels of PBMC and cytokines in short cohort patients, (patients TJ01, TJ01, TJ07, TJO8, TJ10, TJ11, TJ12). Rows: FIG. 6a. serial PBMC counts after vaccination; FIG. 6b. serial assessments of PBMC subpopulation percentages after vaccination (T-cell; B-cell; monocyte); FIG. 6c. serial levels of CCL21 and CXCL12; FIG. 6d. relationship of absolute CD14+ CD16− macrophage counts with MCP-1 (CCL2). CC12 levels remained significantly higher in the short survival cohort compared to long survival cohort. FIG. 6e. scaled comparisons of putative TH-1 cytokine responses after vaccinations (TNF-α×2; CXCL9×350; CXCL10×80). IFN-g is also shown.

FIGS. 7a-7h depict the loss of specific, tumor-promoting monocyte cell populations after vaccination. Substantial tumor regression was observed over a 3 month period. FIG. 7a. Monophasic trend for TME IGF-1R+ cells (ordinal scale); in matched pairs cases from initial diagnosis to vaccination (N=5) no significant difference; matched pairs from vaccine to autopsy (N=4) reveals significant decrease in IGF-1R+ cells (p=0.003). FIG. 7b. IGF-1R positive cells in two patients with evaluable paraffin sections from initial diagnosis through vaccine and autopsy (patients TJ06 and TJ10). FIG. 7c. Biphasic trend for TME CD163 M2 macrophages with significant increase from diagnosis to recurrence (Aperio five 400× fields per phase of treatment per patient; left plot, matched pairs *p<0.0001, N=6) followed by significant loss from recurrence to autopsy after vaccination (right plot, matched pairs *p<0.0001, N=4). FIG. 7d. CD163+ cells in same two patients with evaluable paraffin sections from initial diagnosis through vaccine and autopsy (patients TJ06 and TJ10); increase in CD163 at vaccine v. recurrence (matched pairs, p=0.052) followed by significant decrease in TME CD163 M2 macrophages at autopsy v. vaccine (matched pairs, *p=0.001). FIG. 7e. Significant correlation in the short survival cohort between peripheral CD163 monocytes and CD163 TAM levels documented at surgery ($R^2=0.80$, p=0.02). FIG. 7f. Non-significant correlation between peripheral and TAM CD163 cells in the longer cohort. FIG. 7g. Fluorescence immunohistochemistry photomicrographs from paraffin sections. A, C: Patient TJ10 at Second surgical resection prior to vaccination and B, D: at autopsy; E-H: autopsy specimens obtained from glioblastoma patients undergoing re-resection after standard of care; I, J: untreated, incidentally found post-mortem glioblastoma. FIG. 7h. Time course for treatment response in TJ06 from initial diagnosis through autopsy. Biphasic occurrence of CD163 cells in the TME with increase after standard treatment and decrease after vaccination through autopsy. Loss of CD163 TAMs is associated with increases in both rCBV and ADC values in the tumor. Serum nitrate levels spike after each vaccination and are associated with concomitant rCBV/ADC increases.

FIG. 8a. Upregulation of IGF-1R after polarization of monocytes with M2 cytokines. M1 macrophages do not upregulate the IGF-1R, *p=0.0004. FIG. 8b. Differences in monocyte subset distribution after treatment with IGF-1R AS ODN according to macrophage polarization protocol described in materials and methods. Flow cytometry reveals that IGF-1R AS ODN selectively targets the removal of M2 macrophages. FIG. 8c. Protocol patient serum differentiates immature monocytes into a CD163+ phenotype that co-expresses IGF-1R and PD-L1. IGF-1R AS ODN knocks down this macrophages population in a dose-dependent fashion over a 100-fold concentration range. All values are mean fluorescence intensity. Duplicate measurements for each patient serum co-incubation, comparison of means. *p<0.0001, ♦♦p=0.0001, *p=0.0002, ♦♦♦p=0.0003, ♦♦p=0.0009, ♦p=0.009, ❖❖p=0.0018, ❖p=0.026. FIG. 8d. Summary of means in FIG. 8c.

FIG. 9a. Progression-free survival (PFS) of entire study cohort compared to standard of care (SOC); dotted black lines are 95% confidence interval; FIG. 9b. Overall survival (OS). In both cases SOC falls below the lower 95% CI reflecting a significant improvement; FIG. 9c. PFS by survival cohort at interim analysis; FIG. 9d. OS by survival cohort at interim analysis.

FIG. 10a. Trend of increasing IFN-γ after vaccination in the newly diagnosed vaccine cohort (p=0.06); FIG. 10b. Significant increase in median IFN-γ in the newly diagnosed vaccine cohort (p=0.02); FIG. 10c. Significant increases in IFN-γ levels in 20 chamber cohorts *p<0.0001, p<0.006, *p<0.02; FIG. 10d. Rate of diffusion of labeled IGF-1R AS ODN from the biodiffusion chamber over time.

FIGS. 11a-11j depict the effect of fully formulated biodiffusion chamber (both irradiation and exogenously added AS ODN) on pro-inflammatory cytokine production in a naïve mouse model. Luminex analysis of explanted mouse chamber contents at 24 hour post implantation filled with GL261 cells alone; partial formulation with either addition of 2 µg IGF-1R AS ODN, irradiation of GL261 cells with 5 Gy of X-irradiation; or the fully formulated autologous vaccine (GL261, 2 µg IGF-1R AS ODN, and 5 Gy of gamma-irradiation). FIG. 11a. G-CSF GL261-AS-irr v. GL261-irr p<0.0117; FIG. 11b. IL-la, GL261-AS-irr v. GL261-irr p<0.008; FIG. 1c. IL-1b, GL261-AS-irr v. GL261-irr p<0.0067; FIG. 11d. IL-2, GL261-AS-irr v. GL261-irr p<0.0002; FIG. 11e. IL-9, GL261-AS-irr v. GL261-irr p<0.0413; FIG. 11f. IL-10, GL261-AS-irr v. GL261-irr p<0.0001; FIG. 11g. IL-12(p40), GL261-AS-irr v. GL261-irr p<0.001; FIG. 11h. IL-13, GL261-AS-irr v. GL261-irr p<0.0065; FIG. 11i. IL-15, GL261-AS-irr v. GL261-irr p<0.0013; FIG. 11j. M-CSF, GL261-AS-irr v. PBS p=0.007. Others tested but not shown: IL-6, GL261-AS-irr v. GL261-irr p<0.0836; GM-CSF, GL261-AS-irr v. GL261-irr p<0.0854; lix, GL261-AS-irr v. GL261-irr p<0.0001; kc, GL261-AS-irr v.GL261-irr p<0.0112; TNF-α, GL261-AS-irr v. GL261-irr p<0.0082; VEGF, GL261-AS-irr v. GL261-irr p<0.0004; lif, GL261-AS-irr v. GL261-irr p<0.0140; IL-7, GL261-AS-irr v. GL261-irr p<0.0038; IL-12(p70) GL261-AS-irr v. GL261-irr p<0.0120; IFN-γ, GL261-AS-irr v. GL261-irr p<0.0290.

FIGS. 13a-13b depict in vitro T cell response from contents of fully formulated chamber utilizing T cells derived from vaccinated mice. FIG. 13a. Pro-inflammatory T cell response with DCs primed with antigen retrieved from chambers; **p<0.01 for full formulation in vitro v. no antigen; *p<0.03 for full formulation v. exosomes; FIG. 13b. Pro-inflammatory T cell response with DCs pulsed with antigen retrieved from chambers; **p<0.005 for full formulation v. no antigen; *p<0.007 for full formulation v. exosomes.

FIGS. 15a-15b depict M2 polarization of allogenic monocytes from three normal subjects with overnight incubation from serum derived from six different glioma patients. Controls were not incubated with serum. 1000-fold dilution curve revealed a decrease of M2 macrophages co-expressing FIG. 15a. PDL-1 and FIG. 15b. CD163 from 100 pg of NOBEL antisense to a significant knockdown at 1 µg. Line in each graph is the grand mean. 1 µg of NOBEL v. untreated ***p<0.0002.

FIGS. 21a, 21b, and 21c show pro-inflammatory cytokine levels (pg/ml) in patient serum after vaccination, pooled from serial blood draws over time (days 14-42 post-surgery). A significant dose-dependent increase in pro-inflammatory cytokines was observed in patient serum. FIGS. 21d, 21e, and 21f depict the relationship (polynomial best fit) between wet weight yield of tumor tissue and cytokine yield by subject. A wet weight yield of tissue of 3 grams produced the highest cytokine yield when, after processing, the cells were distributed among 20 chambers.

FIGS. 24a and 24b are Kaplan-Meier curves illustrating median progression-free survival (P-FS) and median overall survival (OS) in the intention-to-treat group (N=30), respectively, in human patients having brain tumors. (Interim analysis is shown in FIG. 9 above.) The "vaccinated" population is treated with 20 chambers implanted and each chamber containing 2 µg NOBEL. The "SoC" population is represented using historical data (N=76). The data shows substantially increased survival both overall and without progression of the cancer.

FIGS. 25a and 25b are Kaplan-Meier curves illustrating progression-free survival and overall survival comparing the same gender and median age in the vaccinated and Standard of Care (SoC) groups respectively. The data shows substantially increased survival both overall and without progression of the cancer.

FIGS. 26a and 26b are Kaplan-Meier curves illustrating progression-free survival and overall survival when excluding the 5 patients who withdrew from treatment and who died from other causes.

FIGS. 27a and 27b are Kaplan-Meier curves illustrating progression-free survival and overall survival when excluding the 9 patients who did not complete the standard of care (SOC) protocol.

FIGS. 28a, 28b, 28c, 28d. illustrate IFN-γ responses induced based on cell yield in the high vaccine cohort. The data show that the optimum IFN-γ release, based on cell number in the chamber. For FIGS. 28a and 28b cell yield is shown in millions of cell. IFN-γ are shown as mean fluorescent intensity (MFI). These data are from the 20-chamber cohort with each chamber containing 2 µg of NOBEL. Data is presented as a polynomial fit (cubic). FIGS. 28c and 20db is an extract of the data in FIGS. 28a and b showing the substantially linear relationship between cell number yield versus mean and peak IFNγ response, respectively, up to 20 million cells. The data are presented here as pg/ml.

FIG. 29a shows the protocol for assessing T-cell response to tumor antigen. For FIG. 29b Antigen was prepared following the in-vivo clinical chamber paradigm. Approximately 1 million ex-vivo GL261 tumor cells were injected into chambers alone or with indicated antisense concentrations and incubated overnight in the chamber which was placed in PBS). The following day, chamber content was extracted and used to pulse naïve dendritic cells. Chamber content which was not treated overnight with antisense was added to the dendritic cells with the indicated amounts of NOBEL. Dendritic cells were also left naïve for control. Following an overnight pulse with antigen, dendritic cells were collected and incubated overnight with T cells from immunized animals in a cell culture plate coated with an ELIPSPOT detection antibody for the cytokine IFNγ. After overnight incubation, the coated plate was processed and developed to enumerate the number of IFNγ producing T-cells which responded to each respective antigen. The data in FIG. 29b shows that tumor antigens were detected in materials recovered from chambers containing GL261 cells plus antisense but not materials from chambers cultured with cells alone, even if antisense was added to the material when the dendritic cells (DC) were pulsed. The data illustrates that antisense in chambers with the glioma cells is required to produce immunostimulatory tumor antigen. For FIG. 29c, GL261 cells were plated in petri dishes and treated overnight with 4 mg NOBEL per 1 million cells or were left untreated. The cells were then collected and placed into chambers at 1 million cells and 2 g NOBEL per chamber. The chambers were then incubated overnight in PBS and the content was extracted the following day. Dendritic cells were then pulsed with the chamber content and IFNγ secretion was measured as described above. The data illustrates that overnight treatment of GL261 cells with antisense enhances the amount of antigen produced by these cells as detected by an increase in the numbers of tumor-immune T cells producing IFN γ.

FIG. 30a shows that high level of Nestin is associated with improved survival following IGF-1R antisense treatment. Mice were implanted in the flank with chambers containing GL261 cells that expressed high or low levels of the nestin protein as well as 4 mg antisense. A control group received high nestin expressing cells alone with no antisense added. The chambers were left in the flank for 24 hours. The immune response was then allowed to develop for several weeks and the mice were challenged intra-cranially on day 35 post-chamber implantation. The immunized mice as well as non-immune controls were monitored for survival after challenge. FIG. 30b shows that a high level of Nestin is associated with better clinical disease score. The data shows scored morbidity associated with brain tumor progression in orthotopic model after vaccination with fully formulated chamber by treatment cohort. FIG. 30c and FIG. 30d show increased production of antibody against GL261 cells associated with high levels of nestin expression. FIG. 30c shows day 28 post chamber/pre-intra-cranial. implantation cell ELISA assay data performed with sera from experimental mice was tested for antibody reactivity to GL261 cell; isolated sera from whole blood taken from the mice. The sera was tested for whole IgG reactivity to GL261 cells with an ELISA assay. FIG. 30d shows cell ELISA data from day 35 post intra-cranial challenge/71 days post-chamber explanation, using sera from experimental mice, tested for antibody reactivity to GL261 cells.

DETAILED DESCRIPTION

Definitions

Figure 1D:
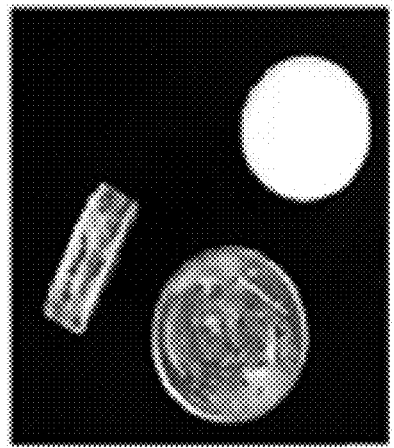
Figure 1E:
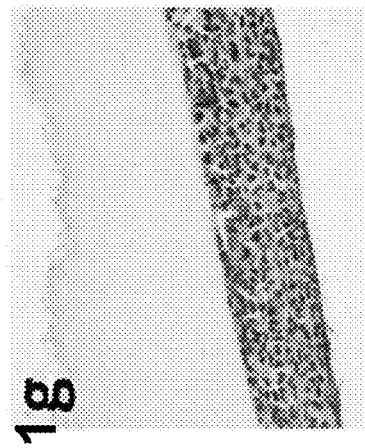

All terms not defined herein have their common art-recognized meanings.

As used herein, terms such as "a," "an," and "the" include singular and plural referents unless the context clearly demands otherwise.

As used herein, the term "about" when preceding a numerical value indicates the value plus or minus a range of 10%. For example, "about 100" encompasses 90 and 110.

As used herein, the term "autologous" means cells or tissues obtained from the same individual.

As used herein, the term "autologous cancer cell vaccine" refers to a therapeutic produced in part by isolating tumor cells from an individual and processing these tumor cells ex vivo. The cells are then re-administered to the individual from whom the tumor cells were isolated. In embodiments, an autologous cancer cell vaccine may comprise additional components in addition to the tumor cells, such as a buffer and/or antisense nucleic acids. In embodiments, "autologous cancer cell vaccine" may refer to a biodiffusion chamber containing the tumor cells and one or more additional components. In certain aspects, the "autologous cancer cell vaccine" may be a "fully formulated chamber" also referred to herein as "fully formulated biodiffusion chamber."

As used herein, the term "fully formulated chamber" or "fully formulated biodiffusion chamber" is a biodiffusion chamber that includes autologous tumor cells and other cells included in the tumor microenvironment (TME) that may or may not be treated prior to encapsulation in the chamber with a first amount of an IGF-1R AS ODN. The cells are encapsulated with exogenous addition of a second amount, for example at least 2 µg, of IGF-1R AS ODN and the chamber is then irradiated with 5 Gy of gamma-irradiation.

As used herein, the term "small molecules" includes nucleic acids, peptides, proteins, and other chemicals (such as, for example, cytokines and growth hormones produced by cells), but does not include cells, exosomes, or microvesicles.

The term "targeting IGF-1R expression" or "targets IGF-1R expression" as used herein refers to administering an antisense nucleic acid that has a sequence designed to bind to the IGF-1R.

As used herein, the term "systemic administration" refers to achieving delivery of a substance throughout the body of a subject. Typical systemic routes of administration include parenteral administration, transdermal administration, intraperitoneal administration, intravenous administration, subcutaneous administration, and intramuscular administration.

Other administration routes include oral administration, nasal administration topical administration, intraocular administration, buccal administration, sublingual administration, vaginal administration, intraheptic, intracardiac, intrapancreatic, by inhalation, and via an implanted pump.

Antisense Molecules

Antisense molecules are nucleic acids that work by binding to a targeted complimentary sequence of mRNA by Watson and Crick base-pairing rules. The translation of target mRNA is inhibited by an active and/or passive mechanism when hybridization occurs between the complementary helices. In the passive mechanism, hybridization between the mRNA and exogenous nucleotide sequence leads to duplex formation that prevents the ribosomal complex from reading the message. In the active mechanism, hybridization promotes the binding of RnaseH, which destroys the RNA but leaves the antisense intact to hybridize with another complementary mRNA target. Either or both mechanisms inhibit translation of a protein contributing to or sustaining a malignant phenotype. As therapeutic agents, antisense molecules are far more selective and as a result, more effective and less toxic than conventional drugs.

The methods and compositions disclosed herein involve the use of antisense molecules for treating cancer. Typically, the antisense molecule is an antisense oligodeoxynucleotide (AS-ODN). In some embodiments, the antisense molecule comprises a modified phosphate backbone. In certain aspects, the phosphate backbone modification renders the antisense more resistant to nuclease degradation. In certain embodiments, the modification is a locked antisense. In other embodiments, the modification is a phosphorothioate linkage. In certain aspects, the antisense contains one or more phosphorothioate linkages. In certain embodiments, the phosphorothioate linkages stabilize the antisense molecule by conferring nuclease resistance, thereby increasing its half-life. In some embodiments, the antisense may be partially phosphorothioate-linked. For example, up to about 1%, up to about 3%, up to about 5%, up to about 10%, up to about 20%, up to about 30%, up to about 40%, up to about 50% up to about 60%, up to about 70%, up to about 80%, up to about 90%, up to about 95%, or up to about 99% of the antisense may be phosphorothioate-linked. In some embodiments, the antisense is fully phosphorothioate-linked. In other embodiments, phosphorothioate linkages may alternate with phosphodiester linkages. In certain embodiments, the antisense has at least one terminal phosphorothioate monophosphate.

In some embodiments, the antisense molecule comprises one or more CpG motifs. In other embodiments, the antisense molecule does not comprise a CpG motif. In certain aspects, the one or more CpG motifs are methylated. In other aspects, the one or more CpG motifs are unmethylated. In certain embodiments, the one or more unmethylated CpG motifs elicit an innate immune response when the antisense molecule is administered to a subject. In some aspects, the innate immune response is mediated by binding of the unmethylated CpG-containing antisense molecule to Toll like Receptors (TLR).

In certain embodiments, the antisense molecule comprises at least one terminal modification or "cap". The cap may be a 5' and/or a 3'-cap structure. The terms "cap" or "end-cap" include chemical modifications at either terminus of the oligonucleotide (with respect to terminal ribonucleotides), and including modifications at the linkage between the last two nucleotides on the 5' end and the last two nucleotides on the 3' end. The cap structure may increase resistance of the antisense molecule to exonucleases without compromising molecular interactions with the target sequence or cellular machinery. Such modifications may be selected on the basis of their increased potency in vitro or in vivo. The cap can be present at the 5'-terminus (5'-cap) or at the 3'-terminus (3'-cap) or can be present on both ends. In certain embodiments, the 5'- and/or 3'-cap is independently selected from phosphorothioate monophosphate, abasic residue (moiety), phosphorothioate linkage, 4'-thio nucleotide, carbocyclic nucleotide, phosphorodithioate linkage, inverted nucleotide or inverted abasic moiety (2'-3' or 3'-3'), phosphorodithioate monophosphate, and methylphosphonate moiety. The phosphorothioate or phosphorodithioate linkage(s), when part of a cap structure, are generally positioned between the two terminal nucleotides on the 5' end and the two terminal nucleotides on the 3' end.

In preferred embodiments, the antisense molecule targets the expression of Insulin like Growth Factor 1 Receptor (IGF-1R). IGF-1R is a tyrosine kinase cell surface receptor that shares 70% homology with the insulin receptor. When activated by its ligands (IGF-I, IGF-II and insulin), it regulates broad cellular functions including proliferation, transformation and cell survival. The IGF-1R is not an absolute requirement for normal growth, but it is essential for growth in anchorage-independent conditions that may occur in malignant tissues. A review of the role of IGF-1R in tumors is provided in Baserga et al., *Vitamins and Hormones,* 53:65-98 (1997), which is incorporated herein by reference in its entirety.

In certain embodiments, the antisense molecule is an oligonucleotide directed against DNA or RNA of a growth factor or growth factor receptor, such as, for example, IGF-1R.

In certain embodiments, the antisense is a deoxynucleotide directed against IGF-1R (IGF-1R AS ODN). The full length coding sequence of IGF-1R is provided as SEQ ID NO:19 (see, for example, PCT/US2016/26970, which is incorporated herein by reference in its entirety).

In certain embodiments, the antisense molecule comprises nucleotide sequences complementary to the IGF-1R signal sequence, comprising either RNA or DNA. The signal sequence of IGF-1R is a 30 amino acid sequence. In other embodiments, the antisense molecule comprises nucleotide sequences complementary to portions of the IGF-1R signal sequence, comprising either RNA or DNA. In some embodiments, the antisense molecule comprises nucleotide sequences complementary to codons 1-309 of IGF-1R, comprising either RNA or DNA. In other embodiments, the antisense molecule comprises nucleotide sequences complementary to portions of codons 1-309 of IGF-1R, comprising either RNA or DNA.

In certain embodiments, the IGF-1R AS ODN is at least about 5 nucleotides, at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, or at least about 50 nucleotides in length. In some embodiments, the IGF-1R AS ODN is from about 15 nucleotides to about 22 nucleotides in length. In certain aspects, the IGF-1R AS ODN is about 18 nucleotides in length.

In certain embodiments, the IGF-1R AS ODN forms a secondary structure at 18° C., but does not form a secondary structure at about 37° C. In other embodiments, the IGF-1R AS ODN does not form a secondary structure at about 18° C. or at about 37° C. In yet other embodiments, the IGF-1R AS ODN does not form a secondary structure at any temperature. In other embodiments, the IGF-1R AS ODN does not form a secondary structure at 37° C. In particular embodiments, the secondary structure is a hairpin loop structure.

In some aspects, the IGF-1R AS ODN comprises the nucleotide sequence of SEQ ID NO: 1, or a fragment thereof. In certain embodiments, the IGF-1R AS ODN may have at least about 70%, at least about 75%, at least about 80%, at least about 85%, at least about 90%, at least about 95%, at least about 96%, at least about 98%, or 100% identity to SEQ ID NO: 1, or a fragment thereof. In some embodiments, the IGF-1R AS ODN comprises one or more phosphorothioate linkages.

In certain aspects, the IGF-1R AS ODN consists of SEQ ID NO: 1. NOBEL is an 18-mer oligodeoxynucleotide with a phosphorothioate backbone and a sequence complimentary to codons 2 through 7 in the IGF-1R gene. As such, NOBEL is an antisense oligonucleotide directed against IGF-1R (IGF-1R AS ODN). The NOBEL sequence, derived as the complimentary sequence of the IGF-1R gene at the 5' end, is:

5'-TCCTCCGGAGCCAGACTT-3'.

NOBEL has a stable shelf life and is resistant to nuclease degradation due to its phosphorothioate backbone. Administration of NOBEL can be provided in any of the standard methods associated with introduction of oligodeoxynucleotides known to one of ordinary skill in the art. Advantageously, the AS ODNs disclosed herein, including NOBEL, may be administered with little/no toxicity. Even levels of about 2 g/kg (scaled) based on mice tests (40 μg in the tail vain) did not reveal toxicity issues. NOBEL can be manufactured according to ordinary procedures known to one of ordinary skill in the art.

The antisense molecule, for example the NOBEL sequence of SEQ ID NO: 1, may also comprise one or more p-ethoxy backbone modifications as disclosed in U.S. Pat. No. 9,744,187, which is incorporated by reference herein in its entirety. In some embodiments, the nucleic acid backbone of the antisense molecule comprises at least one p-ethoxy backbone linkage. For example, up to about 1%, up to about 3%, up to about 5%, up to about 10%, up to about 20%, up to about 30%, up to about 40%, up to about 50% up to about 60%, up to about 70%, up to about 80%, up to about 90%, up to about 95%, or up to about 99% of the antisense molecule may be p-ethoxy-linked. The remainder of the linkages may be phosphodiester linkages or phosphorothioate linkages or a combination thereof. In a preferred embodiment 50% to 80% of the phosphate backbone linkages in each oligonucleotide are p-ethoxy backbone linkages, wherein 20% to 50% of the phosphate backbone linkages in each oligonucleotide are phosphodiester backbone linkages.

Various IGF-1R antisense sequences are bioactive in some or all of the multi-modality effects of the NOBEL sequence. The 18-mer NOBEL sequence has both IGF-1R receptor downregulation activity as well as TLR agonist activity, and further experimentation in mice suggests that both activities are necessary for in vivo anti-tumor immune activity. While the AS ODN molecule has anti-tumor activity, the complimentary sense sequence does not, despite also having a CpG motif.

In certain embodiments, the sequence of the antisense is selected from the group consisting of SEQ ID NOS 1-14, as shown in Table 1. In some embodiments, the antisense has 90% sequence identity to one or more of SEQ ID NOS 1-14. In some embodiments, the antisense has 80% sequence identity to one or more of SEQ ID NOS 1-14. In some embodiments, the antisense has 70% sequence identity to one or more of SEQ ID NOS 1-14.

TABLE 1

Additional downstream sequences for IGF-1R AS ODN Formulation

| Sequences with ACGA Motif | Corresponds to IGF-1R Codons | SEQ ID NO: |
|---|---|---|
| 5'-TCCTCCGGAGCCAGACTT-3' | 2-7 | 1 |
| 5'-TTCTCCACTCGTCGGCC-3' | 26-32 | 2 |
| 5'-ACAGGCCGTGTCGTTGTC-3' | 242-248 | 3 |
| 5'-GCACTCGCCGTCGTGGAT-3' | 297-303 | 4 |
| 5'-CGGATATGGTCGTTCTCC-3' | 589-595 | 5 |
| 5'-TCTCAGCCTCGTGGTTGC-3' | 806-812 | 6 |
| 5'-TTGCGGCCTCGTTCACTG-3' | 1,033-1,039 | 7 |
| 5'-AAGCTTCGTTGAGAAACT-3' | 1,042-1,048 | 8 |
| 5'-GGACTTGCTCGTTGGACA-3' | 1,215-1,221 | 9 |
| 5'-GGCTGTCTCTCGTCGAAG-3' | 1,339-1,345 | 10 |

TABLE 1-continued

Additional downstream sequences
for IGF-1R AS ODN Formulation

| Sequences with ACGA Motif | Corresponds to IGF-1R Codons | SEQ ID NO: |
|---|---|---|
| 5'-CAGATTTCTCCACTCGTCGG-3' | 27-34 | 11 |
| 5'-CCGGAGCCAGACTTCAT-3' | 1-6 | 12 |
| 5'-CTGCTCCTCCTCTAGGATGA-3' | 407-413 | 13 |
| 5'-CCCTCCTCCGGAGCC-3' | 4-8 | 14 |

In certain embodiments, the IGF-1R AS ODN comprises the nucleotide sequence of any one of SEQ ID NOs:1-14, or fragments thereof. In certain embodiments, the IGF-1R AS ODN may have at least about 70%, at least about 75%, at least about 80%, at least about 85%, at least about 90%, at least about 95%, at least about 96%, at least about 98%, or 100% identity to any one of SEQ ID NOs: 1-14, or fragments thereof.

In some embodiments, the antisense molecule downregulates the expression of genes downstream of IGF-1R pathway in a cell. In certain aspects, the downstream gene is hexokinase (Hex II). In some embodiments, the antisense molecule downregulates the expression of housekeeping genes in the cell. In some aspects, the housekeeping gene is L13.

In certain aspects, the IGF-1R AS ODN is chemically synthesized. In certain embodiments, the IGF-1R AS ODN is manufactured by solid phase organic synthesis. In some aspects, the synthesis of the IGF-1R AS ODN is carried out in a synthesizer equipped with a closed chemical column reactor using flow-through technology. In some embodiments, each synthesis cycle sequence on the solid support consists of multiple steps, which are carried out sequentially until the full-length IGF-1R AS ODN is obtained. In certain embodiments, the IGF-1R AS ODN is stored in a liquid form. In other embodiments, the IGF-1R AS ODN is lyophilized prior to storing. In some embodiments, the lyophilized IGF-1R AS ODN is dissolved in water prior to use. In other embodiments, the lyophilized IGF-1R AS ODN is dissolved in an organic solvent prior to use. In yet other embodiment, the lyophilized IGF-1R AS ODN is formulated into a pharmaceutical composition. In some aspects the pharmaceutical composition is a liquid pharmaceutical composition. In other aspects, the pharmaceutical composition is a solid pharmaceutical composition. Additional antisense nucleic acids are also described in U.S. Publication No. 2017/0056430, which is incorporated herein by reference in its entirety.

Autologous Cancer Cell Vaccine

Introduction

Figure 22:
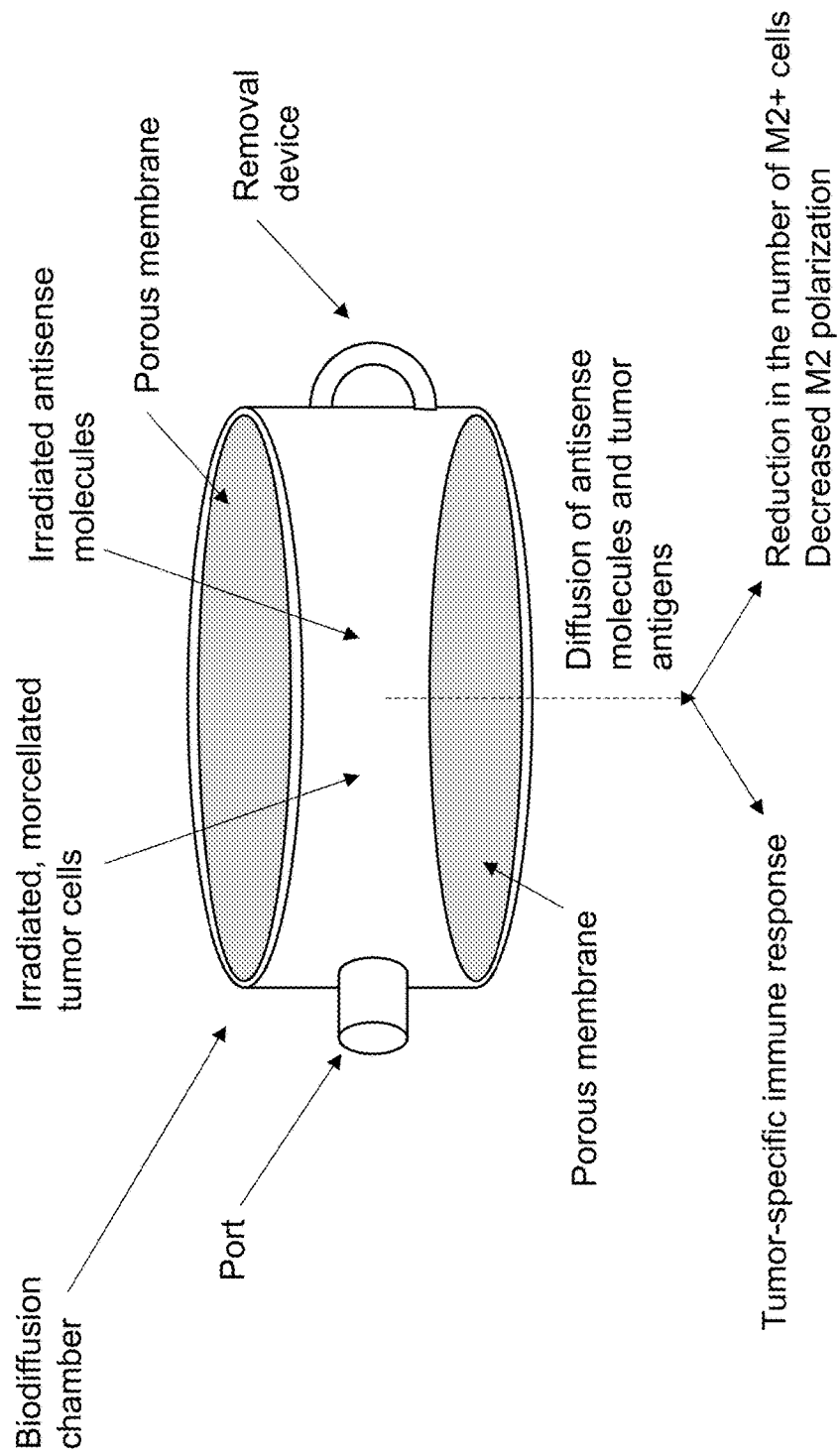
FIG. 22 is a schematic of a representative fully formulated biodiffusion chamber. When the chamber is implanted into a patient, antisense molecules and tumor antigens diffuse through the porous membranes of the chamber, leading to a tumor-specific immune response, decreased M2 polarization, and reduction in the number of M2+ cells.
Figure 23:
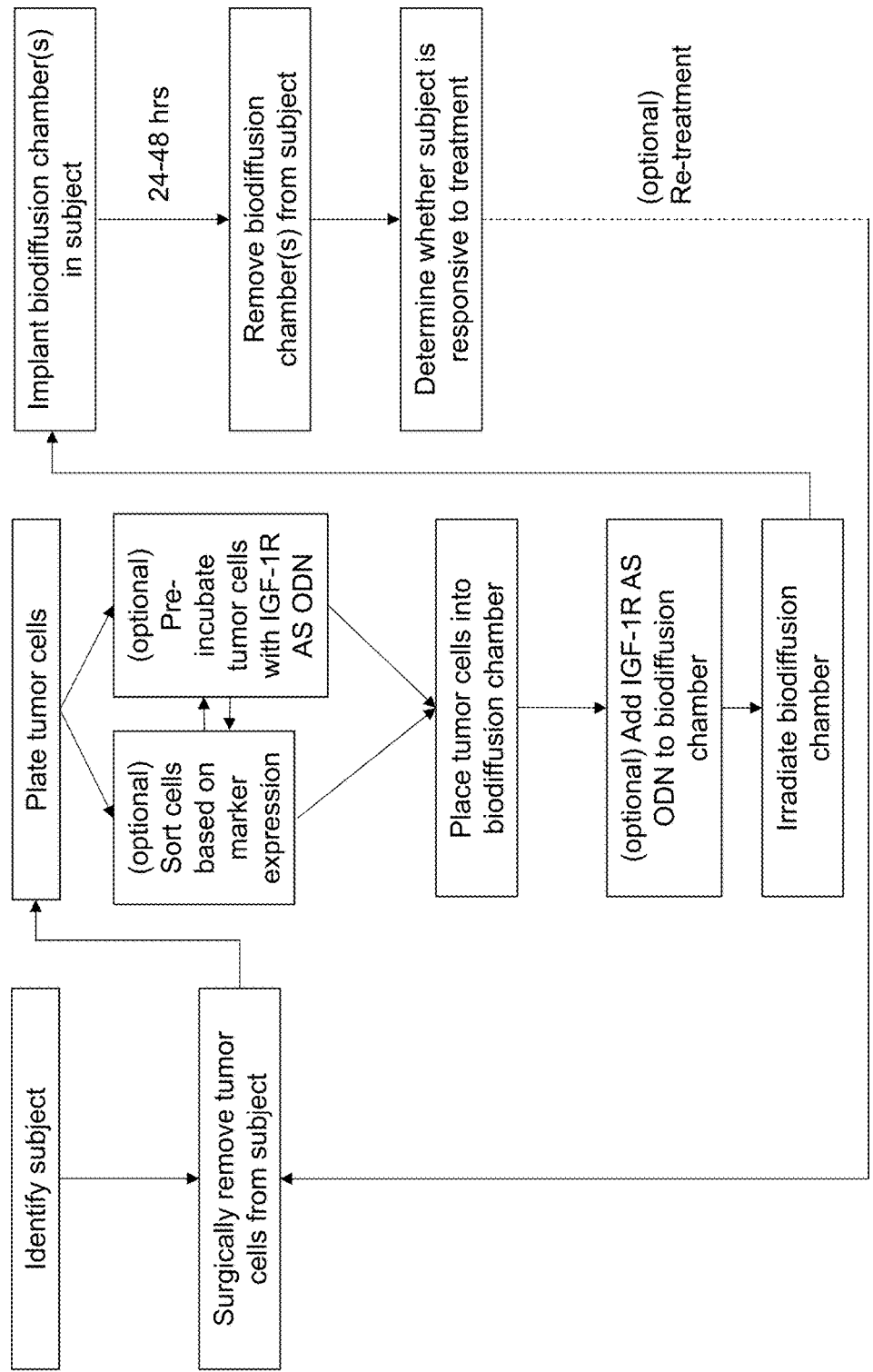
FIG. 23 is a schematic of a representative immunization method. If a patient does not adequately respond to a first round of vaccination, the procedure is optionally repeated as many times as necessary, sometimes in combination with other treatments.

Immunotherapy is currently used to target hematologic malignancies with one common cellular antigen. Unfortunately, solid tumors are far more complex, representing epigenetic progression of genetic changes to a malignant state with an unidentifiable number of tumor-specific targets. Even more challenging, within a WHO diagnostic cancer group there exists marked variations in tumor phenotypes. An autologous cell vaccine would encompass all such variations and all such targets and represent an ideal subject-specific immunotherapy for solid tumor cancers. An autologous cancer cell vaccine however, cannot be derived from primary cell cultures because serial passages alter the tumor phenotype thus diminishing the array of tumor-specific antigens. This would also require impossible lot-release qualification at each passage. The present disclosure eliminates these concerns by plating freshly resected, morselized tumor cells and reimplanting them within 24 hours as a depot antigen, as shown in FIG. 22. In certain aspects, the excellent results achieved herein are obtained by ensuring that an appropriate number of cells are present in the chamber(s), among other specifics described herein.

Previous studies have designed autologous cell vaccine through the use of antigen presenting cells, instead of autologous tumor cells. In this paradigm, a subject's monocytes are collected from a pre-treatment plasma leukopheresis and differentiated into autologous dendritic cells (DC) ex vivo. The dendritic cells are then presented with the subject's tumor crude lysate inducing DC activation/maturation, and at a later time point, the matured dendritic cells, now cross-primed with tumor antigens are injected in the subject as a DC vaccine. Ex vivo differentiation, however, is missing a number of key stimulatory components only occurring in vivo. In addition, differentiation of DCs from hematopoietic precursors requires extensive in vitro manipulations with labor-intensive cell processing in expensive facilities. The present disclosure obviates these concerns by providing an endogenous DC maturation process and an immunomodulatory and immunostimulatory antisense oligodeoxynucleotide (AS-ODN) that promotes the development of an appropriate immune response. More specifically, the present disclosure provides a biodiffusion chamber comprising dispersed tumor cells derived from the patient and irradiated antisense molecules, which is implanted into the patient for therapeutically effective time. Without being bound by any theory, it is thought that the combination of irradiated tumor cells, antisense, and biodiffusion chamber act in concert to simulate the local immune response, and enhance the response by reducing or eliminating M2 cells, preventing dampening of the immune system.

Thus, the present disclosure shows that an irradiated, implantable biodiffusion chamber comprising freshly resected tumor cells and IGF-1R AS ODN safely serves as an effective, subject-specific autologous cell vaccine for cancer immunotherapy. As such, the use of the claimed implantable biodiffusion chamber to mount an immune response that selectively targets tumor cells in a subject provides a new and significant approach for the treatment of cancer, especially GBM.

Biodiffusion Chamber

A representative diffusion chamber comprises a chamber barrel having two ends, a first end and a second end. In embodiments, the biodiffusion chamber is a small ring capped on either side by a porous, cell-impermeable membrane, such as the Duropore membrane manufactured by Millipore Corporation. Optionally, one of the ends may be closed off as part of the chamber body leaving only one end open to be sealed using the porous membrane. The membranes can be made of plastic, teflon, polyester, or any inert material which is strong, flexible and able to withstand chemical treatments. The chamber can be made of any substance, such as and not limited to plastic, teflon, lucite, titanium, Plexiglass or any inert material which is non-toxic to and well tolerated by humans. In addition, the chambers should be able to survive sterilization. In some aspects, the diffusion chambers are sterilized with ethylene oxide prior to use. Other suitable chambers are described in U.S. Prov. No. 62/621,295, filed Jan. 24, 2018, U.S. Pat. No. 6,541,036, PCT/US16/26970, and U.S. Pat. No. 5,714,170, which are each incorporated herein by reference in their entirety.

In certain embodiments, the membrane allows passage of small molecules but does not allow passage of cells (i.e., the cells cannot leave or enter the chamber). In some aspects, the diameter of the pores of the membrane allows nucleic acids and other chemicals (such as, for example, cytokines produced by cells) to diffuse out of the chamber, does not allow passage of cells between the chamber and the subject in which it is implanted. The biodiffusion chambers useful in the present disclosure include any chamber which does not allow passage of cells between the chamber and the subject in which it is implanted, provided however, that the chamber permits interchange and passage of factors between the chamber and the subject. Thus, in certain aspects, the pore size has a cut-off that prevent passage of materials that are greater than 100 $\mu m^3$ in volume into and out of the chamber. In some embodiments, the pores of the membrane have a diameter of about 0.25 μm or smaller. For example, the pores may have a diameter of about 0.1 μm (see FIG. 1). In particular aspects, the pores range in diameter from 0.1 μm to 0.25 m. See also, Lange, et al., J. Immunol., 1994, 153, 205-211 and Lanza, et al., Transplantation, 1994, 57, 1371-1375, each of which is incorporated herein by reference in their entireties. This pore diameter prevents the passage of cells in or out of the chamber. In certain embodiments, diffusion chambers are constructed from 14 mm Lucite rings with 0.1 μm pore-sized hydrophilic Durapore membranes (Millipore, Bedford, Mass.).

In certain embodiments, a biodiffusion chamber comprises a membrane that allows the IGF-1R AS ODN to diffuse out of the chamber. In some embodiments, about 50% of the IGF-1R AS ODN diffuses out of the chamber in about 12 hours, about 60% of the IGF-1R AS ODN diffuses out of the chamber in about 24 hours, about 80% of the IGF-1R AS ODN diffuses out of the chamber in about 48 hours, and/or about 100% of the IGF-1R AS ODN diffuses out of the chamber in about 50 hours.

In an exemplary approach, to assemble the biodiffusion chamber, a first porous membrane is attached to one side of a first diffusion chamber, using glue and pressure to create a tight seal. A second porous membrane is similarly attached to a second diffusion chamber ring. The membranes can be secured in position with rubber gaskets which may also provide a tighter seal. The diffusion chamber rings are left overnight (minimum 8 hours) to dry. Then, the first diffusion chamber ring and the second diffusion chamber ring are attached to one another using glue and left overnight (minimum 8 hours) to dry. In a preferred embodiment, the first chamber ring and second chamber ring joining process comprises using 2 dichloroethane as a solvent to facilitate adhesion between the two rings. See, for example, FIG. 22 showing two porous membranes. In an alternative approach, the chamber may have only one side that contains a porous membrane.

On the barrel portion of the chamber, one or more openings (e.g. ports) are provided which can be covered by a cap which is accessed from outside of the subject's body once the chamber is implanted, thus allowing the diffusion chamber to be refilled. The openings allow for multiple and sequential sampling of the contents, without contamination and without harming the subject, therefore significantly reducing the number of implantation procedures performed on the subject. Before implantation into the patient, the one or more openings may be sealed with bone wax, a port plug or cap made from, for example, PMMA. The cap can be a screw-on type of self-sealing rubber and fitted to the opening. In some configurations, the diffusion chamber may contain two or more injection openings or ports. Sampling of the chamber contents can be performed by accessing the opening by removing the cap on the outside of the subject's body and inserting an ordinary needle and syringe. In some embodiments, the chamber may further include a removal device. Such a device facilitates removal of the chamber from the patient.

Figure 12:
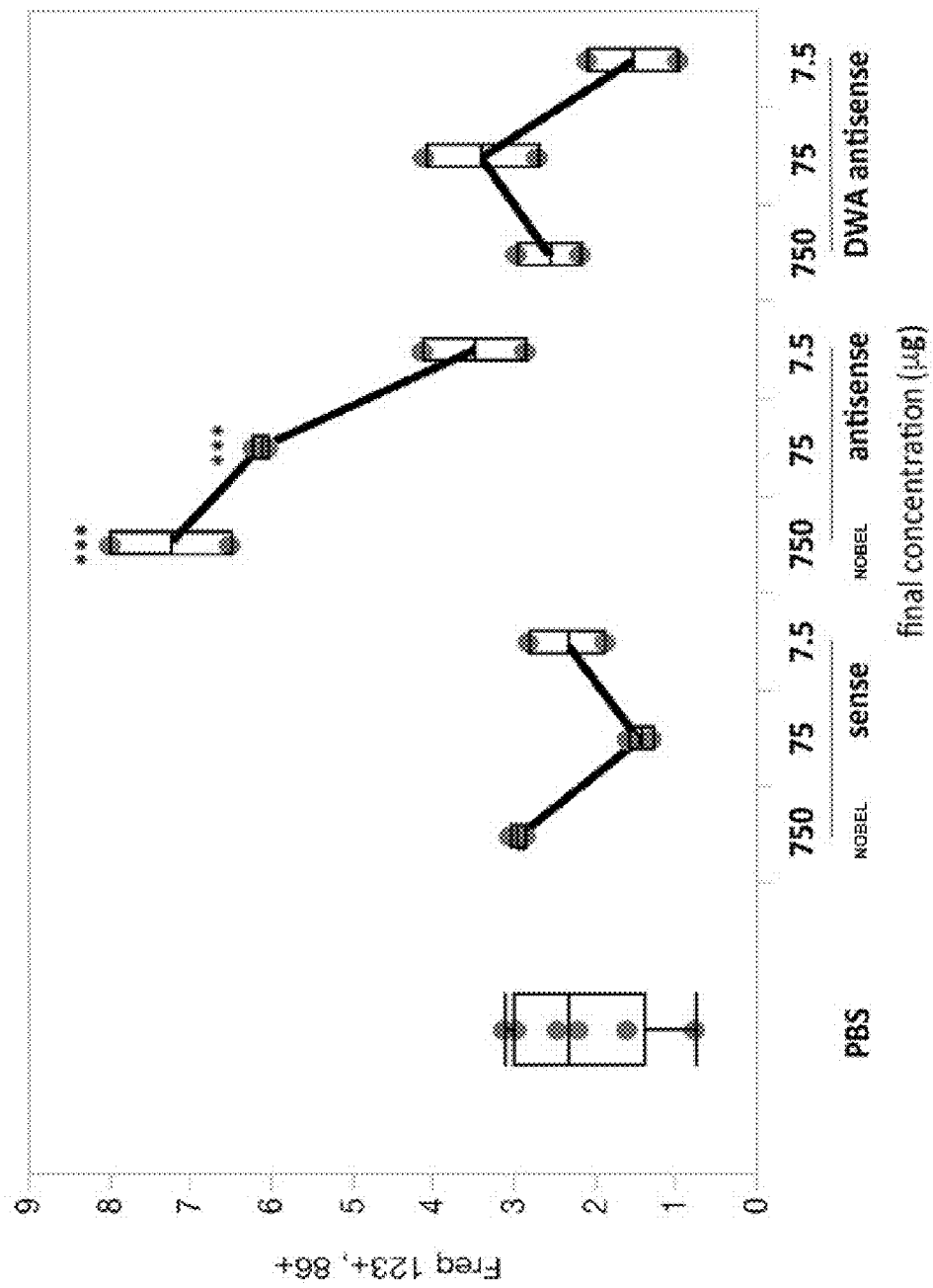
FIG. 12 shows titration curves for dendritic cell (DC) activation of peripheral blood mononuclear cells (PBMC) from two normal subjects (red and blue) by IGF-1R AS ODN; NOBEL antisense 750 µg v. NOBEL sense 75 µg, 7.5 µg, DWA antisense 750 µg, 7.5 µg, control, ***p<0.0009; NOBEL antisense 75 µg v. NOBEL sense, DWA antisense 7.5 µg.
Figure 14A:
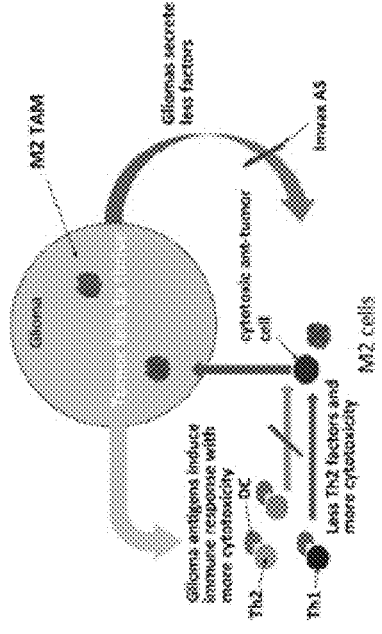
FIGS. 14a-14d are schematic representations of biphasic response to NOBEL antisense dose titration.
Figure 14B:
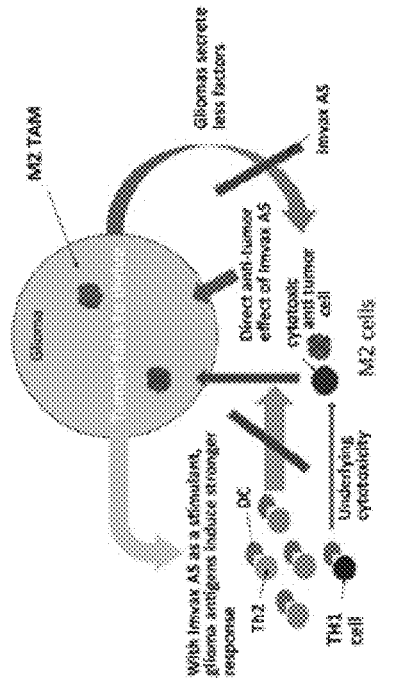
Figure 14C:
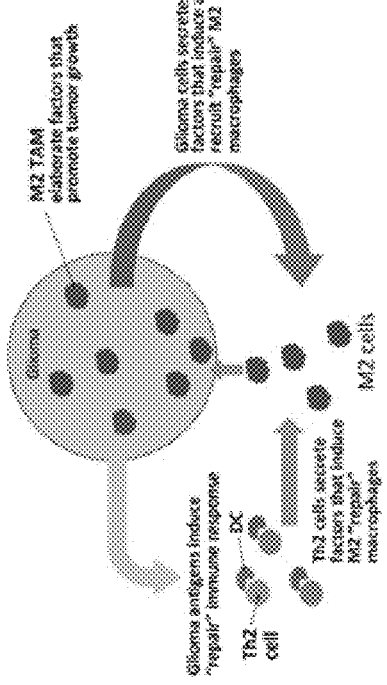
Figure 14D:
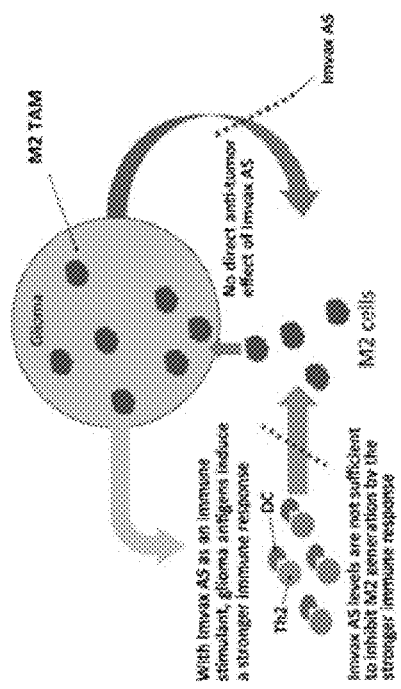

In embodiments, the chamber serves as an antigen depot designed so that tumor antigens diffuse out of the chamber for the purpose of promoting a therapeutic host immune response. Exogenous IGF-1R AS ODN and ex vivo irradiation promote a pro-inflammatory response. This formulation is associated with clinical and radiographic improvements, prolonged survival on protocol, and represents a novel autologous cell vaccine that includes an exogenous active pharmaceutical ingredient (API) and radiation that we interpret as inducing or enhancing tumor immunity effect. Furthermore the addition of low concentration of the IGF-1R AS ODN is critical to a pro-inflammatory response (FIG. 12).

In certain embodiments the disclosure provides a biodiffusion chamber for implantation into a subject suffering from cancer comprising: (a) tumor cells; and (b) an effective amount of an antisense molecule. In other embodiments is provided a method for treating cancer in a subject comprising: (a) obtaining a biodiffusion chamber comprising tumor cells and an effective amount of an antisense nucleic acid; (b) irradiating the biodiffusion chamber and contents; and (c) implanting the irradiated biodiffusion chamber into the subject for a therapeutically effective time.

In certain embodiments, the IGF-1R AS ODN is present in the biodiffusion chamber in an amount ranging from about 0.5 μg to about 10 μg. In certain aspects, the IGF-1R AS ODN is present in an amount ranging from about 1 μg to about 5 μg per chamber, or from about 2 μg to 4 μg per chamber. In specific aspects, the IGF-1R AS ODN is present in an amount of about 2 μg per chamber. In specific aspects, the IGF-1R AS ODN is present in an amount of about 4 μg per chamber. Without being bound by theory it is thought that these levels promote an enhanced Th1 response in a subject, while avoiding an M2 immunostimulatory response in the subject.

In certain embodiments, the tumor cells are not treated with an IGF-1R AS ODN prior to encapsulation in the chamber. Typically, however, the tumor cells are treated with an IGF-1R AS ODN prior to encapsulation in the chamber. The time for treating the cells pre-encapsulation may vary. For example, the tumor cells may be treated ex vivo with an IGF-1R AS ODN immediately before encapsulation, for up to about 4 hours, for up to about 6 hours, for up to about 8 hours, for up to about 12 hours or for up to about 18 hours. Typically, the tumor tissue may be treated ex vivo for about 12 hours to about 18 hours pre-encapsulation. Conveniently, the cells may be encapsulated after a pre-treatment lasting up to overnight. Without being bound by theory, it is thought that the pre-encapsulation treatment plays a desirable role in stimulating production of tumor antigen.

The amount of IGF-1R AS ODN used for the pre-encapsulation treatment may be in a range of about 1 mg to 8 mg per million cells; for example, about 2 mg to about 6 mg per million cells, about 3 mg to about 5 mg per million cells. Typically the amount of IGF-1R AS ODN used for treatment prior to encapsulation is about 4 mg per million cells.

In some embodiments, the IGF-1R AS ODN for ex vivo treatment of the tumor cells is used at a concentration ranging from about at least 2 mg/ml to at least about 5 mg/ml. In certain aspects, the IGF-1R AS ODN is used at a concentration of at least 4 mg/ml. In specific embodiments, the IGF-1R AS ODN is used at a concentration of 4 mg/ml.

In certain embodiments, the IGF-1R AS ODN used to treat tumor cells ex vivo and the IGF-1R AS ODN present in the chamber are the same. In other embodiments, the IGF-1R AS ODN used to treat tumor cells ex vivo and the IGF-1R AS ODN present in the chamber are different. In certain embodiments, the IGF-1R AS ODN used to treat tumor cells ex vivo is at least about 5 nucleotides, at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, or at least about 50 nucleotides in length. In some embodiments, the IGF-1R AS ODN used to treat tumor cells ex vivo is from about 15 nucleotides to about 22 nucleotides in length. In certain aspects, the IGF-1R AS ODN used to treat tumor cells is about 18 nucleotides in length.

In certain embodiments, the IGF-1R AS ODN used to treat tumor cells ex vivo forms a secondary structure at 18° C., but does not form a secondary structure at about 37° C. In other embodiments, the IGF-1R AS ODN used to treat tumor cells does not form a secondary structure at about 18° C. or at about 37° C. In yet other embodiments, the IGF-1R AS ODN used to treat tumor cells ex vivo does not form a secondary structure at any temperature. In other embodiments, the IGF-1R AS ODN used to treat tumor cells does not form a secondary structure at 37° C. In particular embodiments, the secondary structure is a hairpin loop structure.

In some aspects, the IGF-1R AS ODN used to treat tumor cells comprises the nucleotide sequence of SEQ ID NO: 1, or a fragment thereof. In certain embodiments, the IGF-1R AS ODN used to treat tumor cells may have at least about 70%, at least about 75%, at least about 80%, at least about 85%, at least about 90%, at least about 95%, at least about 96%, at least about 98%, or 100% identity to SEQ ID NO: 1, or a fragment thereof. In certain aspects, the IGF-1R AS ODN used to treat tumor cells is SEQ ID NO: 1.

After the tumor cells are treated with the AS-ODN for a period of time, the AS-ODN is removed and fresh AS-ODN is added to the chamber, which is then irradiated prior to implantation into a subject. In certain aspects, the biodiffusion chamber is treated with gamma irradiation at an amount of about 1 Gy, about 2 Gy, about 4 Gy, about 5 Gy, about 6 Gy, about 10 Gy, or up to about 15 Gy. In certain aspects, the dose of radiation is not more than about 5 Gy. In other aspects, the dose of radiation is at least about 5 Gy. In some aspects, the dose of radiation is 5 Gy. In certain embodiments, the biodiffusion chamber may be irradiated at least once, at least twice, at least three times, at least four times, or at least five times. In some embodiments, the chamber is irradiated less than about 24 hours prior to implantation into a subject. In other embodiments, chamber is irradiated about 24 hours prior to implantation into the subject. In yet other embodiments, the chamber is irradiated at least about 24 hours prior to implantation into the subject. In still other embodiments, the chamber is irradiated not more than about 48 hours prior to implantation into the subject. In yet other embodiments, the chamber is irradiated at least about 48 hours prior to implantation into the subject.

While the tumor cells are typically killed prior to implantation; for example by radiation, the cells need not be killed and indeed it may be advantageous to maintain the cells in an alive state to promote release of antigen. Thus, in certain embodiments, the cells may not be irradiated prior to implantation. For safety purposes, however, it is desirable to prevent release of live tumor cells into the subject.

Figure 28D:
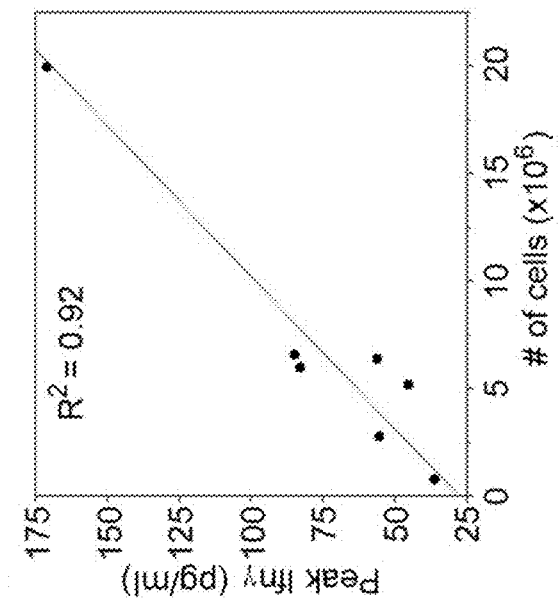
Figure 28C:
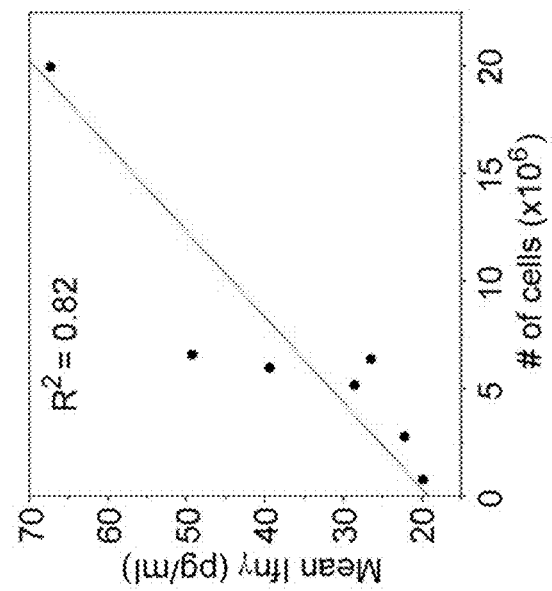

Tumor cells can be placed in a diffusion chamber in varying numbers. In certain embodiments, about $1\times10^4$ to about $5\times10^6$ tumor cells are placed in each diffusion chamber. In other embodiments, about $1\times10^5$ to about $1.5\times10^6$ tumor cells are placed in the diffusion chamber. In yet other embodiments, about $5\times10^5$ to $1\times10^6$ tumor cells are placed in the chamber. with a subject can be used. We have discovered that the number of tumor cells can impact the subjects' anti-tumor response and that an appropriate range should be selected to increase the chance to obtain the desired results. FIG. 28 shows data from patients implanted with 20 chambers and shows cell yield (millions of cells) corresponding to immune response. The anti-tumor immune response is optimal in a range of about 750,000 to about 1,250,000 cells in a chamber, with a peak at about 1 million cells/chamber. Multiple chamber containing irradiated tumor cells are administered and to maintain the optimal immune the response the number of cells/chamber is preferably maintained within the range. Preferably, the tumor cells are intact and not autolyzed or otherwise damaged as described herein.

In certain embodiments, it may be preferable to maintain the ratio of cells to AS ODN in a chamber. Thus, in certain aspects a chambers may contain about 2 μg of AS ODN and between 750,000 and 1,250,000 cells; for example 1,000,000 cells. The ratio of cells to AS ODN may thus be in a range from about $3.75\times10^5$ to about $6.25\times10^5$ per μg AS ODN; for example, about $5.0\times10^5$ cells per μg. Thus, in a typical patient receiving 20 chambers the total dose of AS ODN is about 40 μg.

Typically, administration will be in a chamber as described herein; however, in certain aspects, the irradiated cells and IGF-1R AS ODN may be co-administered to the subject without being contained physically together in the chamber or another container. In certain methods using this approach, the irradiated cells IGF-1R AS ODN thus disperse, diffuse, or are metabolized in the body limited by the physiology of the subject. Thus, in certain aspects, e.g. the tumors cells for use may be prepared as described herein for the chamber and administered with the IGF-1R AS ODN but the administration may be not contained within a physical container. Such administration is typically intramuscular.

Tumor Tissue Preparation for Chamber

Tumor cells for use in the autologous vaccination are surgically removed from the subject. In embodiments, the tumor cells are removed from the patient using a tissue morselator. The extraction device preferably combines a high-speed reciprocating inner cannula within a stationary outer cannula and electronically controlled variable suction. The outer cannula has a diameter of 1.1 mm, 1.9 mm, 2.5 mm, or 3.0 mm, and a length of 10 cm, 13 cm, or 25 cm. The instrument also relies on a side-mouth cutting and aspiration aperture located 0.6 mm from the blunt desiccator end. The combination of gentle forward pressure of the aperture into the tissue to be removed and suction draws the desired tissue into the side aperture, allowing for controlled and precise tissue resection through the reciprocal cutting action of the inner cannula. A key feature is the absence of a rotation blade; this avoids drawing unintended tissue into the aperture. An example of a suitable device is the Myriad® tissue aspirator (NICO Corporation® Indianapolis, Ind.), a minimally invasive surgical system which may be used for the removal of soft tissues with direct, microscopic, or endoscopic visualization. The shaved tissue is suctioned, gathered in to a collection chamber, and is collected in a sterile tissue trap. During collection of the tissue in the sterile tissue trap, blood is removed from the preparation. Preferably, the sterile trap contains a collection dish at the bottom of the trap and a stem that provides access to the trap. The trap structure may also contain an inner ladle-shaped structure that is removable from the trap to facilitate tissue removal from the trap.

Preferably, the morselator generates no heat at the resection site or along its shaft, and requires no ultrasonic energy for tissue removal. Thus, in particular embodiments, the tumor tissue is morselized tumor tissue (i.e. tumor shaved tissue obtained by side-mouth cutting in the absence of heat, and optionally in the absence of ultrasonic treatment). Advantageously, the aspirator-extract and morselized tissue has higher viability than tissue removed by other methods. It is believed that the extraction process maintains higher tumor cell viability in part due to restricting exposure of the tumor cells to high temperatures during removal. For example, the methods herein do not expose tumor cells to above 25° C. during removal. Thus, the cells are not exposed to temperatures above body temperature, i.e., about 37° C.

The amount of tumor tissue obtained from the subject may vary. Preferably, the amount is at least 1, at least 2, at least 3 grams or at least 4 grams of wet tumor tissue is obtained from the patient. The tissue is removed from the sterile tissue trap and disaggregated by pipetting with a sterile pipette to break up large tissue fragments. The disaggregated cell suspension is then placed onto sterile tissue culture plates in serum-containing media, and incubated in a tissue culture incubator. This plating step serves to enrich the desired functional cells by adherence, and also helps to remove debris from the preparation. Thus, the tumor cells used in treatments described herein preferably consist essentially of, or consist of, adherent cells from the tumor tissue.

After a predetermined incubation time (e.g., 6, 12, 24, or 48 hours), the cells are removed from the plates. The cells may be removed by scraping, by chemical methods (e.g. EDTA) or by enzymatic treatment (e.g. trypsin). The cells are placed into one or more diffusion chambers. In some embodiments, the cells are split between 2, 3, 4, 5, 6, 7, 8, 9, 10, 11, 12, 13, 14, 15, 16, 17, 18, 19, 20, 21, 22, 23, 24, 25, 26, 27, 28, 29, 30 or more diffusion chambers. Often, 20 chambers are used. In some embodiments, each diffusion chamber contains an equal number of cells. In some embodiments, a first diffusion chamber contains more cells than a second chamber.

In some embodiments, the cells are sorted before being placed in the chamber. In some embodiments, the cells are enriched by selecting for one or more cellular markers before being placed in the chamber. The selection may be performed, for example, using beads or by cell sorting techniques known to those of skill in the art. In some embodiments, the cells placed into the chamber are enriched for one or more markers.

In some embodiments, implantation of the biodiffusion chamber for a therapeutically effective time reduces or eliminates return of the cancer in the subject. In certain aspects, implantation of the biodiffusion chamber causes a reduction of tumor volume associated with the cancer in the subject. In yet other embodiments, implantation of the biodiffusion chamber for a therapeutically effective time induces elimination of the tumor in the subject. In some embodiments, implantation of the chamber inhibits regrowth of the tumor for at least 3 months, at least 6 months, at least 12 months, at least 36 month, or indefinitely.

The biodiffusion chamber can be implanted in a subject in the following non-limiting ways: subcutaneously, intraperitoneally, and intracranially. In certain embodiments, the diffusion chamber(s) is implanted into an acceptor site of the body having good lymphatic drainage and/or vascular supply such as the rectus sheath. In other embodiments, a refillable chamber can be employed such that the diffusion chamber can be re-used for treatments and emptied following treatments. In certain aspects, a plurality of diffusion chambers, preferably between 5 and 20, can be used in a single subject.

In certain embodiments, at least about 1, at least about 2, at least about 3, at least about 4, at least about 5, at least about 10, at least about 15, at least about 20, at least about 25, at least about 30, at least about 35, at least about 40, at least about 45, or at least about 50 chambers are implanted into the subject. In some embodiments, 10-20 chambers are implanted into the subject. Preferably, about 20 chambers are implanted into the subject. In certain embodiments, the tumor cells are divided equally among each chamber.

Typically, the chamber is removed after period of time. For example, the chamber may be implanted in the subject for about 24 hours, about 48 hours, about 72 hours, or about 96 hours. Implantation for about 48 hours is associated with beneficial therapeutic outcomes. Accordingly, the preferred time of implantation is about 48 hours. In certain embodiments, the vaccination procedure is performed one time per patient. In other embodiments, the vaccination procedure is performed multiple times per patient. In embodiments, the vaccination procedure is performed two times, three times, four times, five times, six times, seven times, or eight times in a single patient. In embodiments, the vaccination is repeated every 7, 14, or 28 days, or every 1, 3, or 6 months for a given period of time. In further embodiments, the vaccination procedure is repeated periodically until the patient is free of cancer.

Without being bound by theory, it is thought that implantation of the biodiffusion chamber causes elimination or reduction of M2 cells at or near the implantation site such that an immune response against tumor antigens diffusing out from the chamber is achieved. In certain aspects, elimination or reduction of M2 cells at the implantation site leads to enhanced presentation of autologous tumor antigens by antigen-presenting cells (APC) to CD4 T cells leading to production of interferon-gamma (IFNγ) and the induction of type 1 tumor immunity. In certain aspects, the production of IFNγ by tumor antigen-specific CD4 T cells and the anti-M2 effects of IGF-1R AS ODN drive type 1 anti-tumor immunity and the loss of anti-inflammatory M2 cells from the circulation and tumor microenvironment indirectly interfering with tumor growth. In some aspects, the production of IFNγ by tumor antigen-specific CD4 T cells and the anti-M2 effects of IGF-1R AS ODN unleashes effector-mediated damage to the tumor cells and tumor microenvironment (M2 cells) and initiates the longer process of programming memory T cells recognizing tumor antigens. In certain embodiments, the anti-tumor adaptive immune response sustains continued tumor regression.

Optionally, the cells introduced into the chamber may be enriched for certain cell types. Nestin a, cytoskeleton-associated class VI intermediate filament (IF) protein, has traditionally been noted for its importance as a neural stem cell marker. We have discovered that in certain brain tumor samples, cells positive for nestin (nestin+ cells) are enriched compared to benign tissue, and that this associated corresponds to improved therapeutic response. Thus, in certain aspects, a subject's tumor can be biopsied to assess the degree of nestin expression, and therefore, in certain aspects, the chamber cells are enriched Nestin-positive ("+") cells compared to benign tissue. Without being bound by theory, it is thought that nestin provides a marker associated with antigens suitable useful in producing an anti-tumor immune response. Accordingly, the cells implanted into the chamber may be enriched for nestin+ cells compared to the tumor cell population as a whole when extracted from the subject. FIG. 30 illustrates the enhance immune response obtained when the tumor sample used to stimulate a response is enriched with Nestin.

Systemic Administration

As an alternative to, or supplement to, implantation of the chambers, IGF-1R AS ODN may be administered systemically. Thus, in embodiments, the IGF-1R AS ODN is provided in a pharmaceutical composition for systemic administration. In addition to the IGF-1R AS ODN, the pharmaceutical composition may comprise, for example, saline (0.9% sodium chloride). The composition may comprise phospholipids. In some aspects, the phospholipids are uncharged or have a neutral charge at physiologic pH. In some aspects, the phospholipids are neutral phospholipids. In certain aspects, the neutral phospholipids are phosphatidylcholines. In certain aspects, the neutral phospholipids are dioleoylphosphatidyl choline (DOPC). In some aspects, the phospholipids are essentially free of cholesterol.

In some aspects, the phospholipids and oligonucleotides are present at a molar ratio of from about 5:1 to about 100:1, or any ratio derivable therein. In various aspects, the phospholipids and oligonucleotides are present at a molar ratio of about 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, or 100:1. In some aspects, the oligonucleotides and phospholipids form an oligonucleotide-lipid complex, such as, for example, a liposome complex. In some aspects, at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the liposomes are less than 5 microns in diameter. In various aspects, the composition further comprises at least one surfactant, such as, for example, polysorbate 20. In some aspects, at least about 5% of the total liposomal antisense drug product consists of surfactant and at least about 90% of the liposomes are less than 5 microns in diameter. In some aspects, at least about 15% of the total liposomal antisense drug product consists of surfactant and at least about 90% of the liposomes are less than 3 microns in diameter. In some aspects, the population of oligonucleotides are incorporated in the population of liposomes.

In some aspects the pharmaceutical composition is a liquid pharmaceutical composition. In other aspects, the pharmaceutical composition is a solid pharmaceutical composition.

Dosages for systemic administration of the antisense in human subjects may be about 0.025 g/kg, about 0.05 g/kg, about 0.1 g/kg, about 0.15 g/kg, or about 0.2 g/kg. In certain embodiments, the dosage for systemic administration may be from 0.025 g/kg to 0.2 g/kg. In some embodiments, the dosage is about 0.2 g/kg. In other embodiments, the dosage is from 0.004 g/kg to 0.01 g/kg. In other embodiments, the dosage is less than 0.01 g/kg. In further embodiments, the dosage is not between 0.01 g/kg to 0.2 g/kg. In certain aspects, the antisense is supplied as a lyophilized powder and re-suspended prior to administration. When resuspended the concentration of the antisense may be about 50 mg/ml, about 100 mg/ml, about 200 mg/ml, about 500 mg/ml, about 1000 mg/ml, or a range between those amounts.

In certain embodiments, the AS ODN may be administered systemically pre-operatively; for example prior to surgery to reduce tumor burden. For example, the AS ODN may be administered up to 24 hours, up to 36 hours, up to 48 hours or up to 72 hours before surgery. In particular aspects, the pharmaceutical composition may be administered about 48 to about 72 hours before surgery. Typically, in such circumstances, the administration is by intravenous bolus.

Combination Therapies

Historically, cancer therapy has involved treating subjects with radiation, with chemotherapy, or both. Such approaches have well-documented challenges. Advantageously, however, the chamber implantation methods disclosed herein may be used to treat a subject having cancer as a monotherapy. Thus it is preferable that the methods disclosed herein do not include chemotherapy or radiation therapy. Notwithstanding the excellent effect achieved by monotherapy approaches herein, however, it may be beneficial under certain circumstances to combine the chamber methods with other therapies; for example, radiation therapy. In certain embodiments, the radiation therapy includes, but is not limited to, internal source radiation therapy, external beam radiation therapy, and systemic radioisotope radiation therapy. In certain aspects, the radiation therapy is external beam radiation therapy. In some embodiments, the external beam radiation therapy includes, but is not limited to, gamma radiation therapy, X-ray therapy, intensity modulated radiation therapy (IMRT), and image-guided radiation therapy (IGRT). In certain embodiments, the external beam radiation therapy is gamma radiation therapy. Radiation may be administered before chamber implantation or after implantation; for example, as a salvage therapy. Typically, such salvage therapy approaches are not implemented until the cancer is determined to have returned.

Thus, in certain combination approaches, both the chamber methods, and the systemic methods and compositions, described herein may be used in the same subject, alone or in combination with radiation or chemotherapy. In the combination approaches described herein, the chamber implantation is preferably used as a first-line therapy. Using the chamber implantation first is desirable because the subject's immune system can be inhibited by other therapies, reducing the therapeutic benefit of the chamber implantation.

Optionally, systemic administration may be performed prior to chamber implantation. Such an approach can be used to enhance the subjects immune system, as a priming approach. The priming approach may be especially advantageous where prior therapy has resulted in the subject having a compromised immune system.

When systemic administration is used in combination, the AS ODN may be systemically administered at least 2 weeks, at least 1 week, at least 3 days, or at least 1 day prior to treatment of the patient using an autologous cancer cell vaccine. In other embodiments, the AS ODN may be systemically administered at least 1 day, at least 3 days, at least 1 week, or at least 2 weeks following treatment of the patient using an autologous cancer cell vaccine; i.e. the chamber.

Optionally, the subject may be revaccinated with chambers using the methods described here subsequent to the first vaccination. A second or further additional vaccination may use tumor cells taken from the subject during the tissue removal and stored. Optionally, the second or further additional vaccination may use fresh tumor tissue removed from the subject and treated as described herein. Any tumor remaining in the subject may express the same antigens and thus act as a depot, providing for re-stimulation. However, recurring tumors may develop new antigens and thus provide additional options to stimulate an anti-tumor response. A subsequent vaccination may be after the first treatment is complete and the tumor has recurred or if the subject has not responded to the first treatment.

Subjects for Treatment with the IGF-1R AS ODN

Suitable subjects are animal with cancer; typically, the subject is a human. While brain cancers, such as glioblastoma, benefit particularly from this methods disclosed herein, the methods apply to cancer generally. Accordingly, the disclosure provides methods of treating cancers, including those selected from the group consisting of: glioma, astrocytoma, hepatocarcinoma, breast cancer, head and neck squamous cell cancer, lung cancer, renal cell carcinoma, hepatocellular carcinoma, gall bladder cancer, classical Hodgkin's lymphoma, esophageal cancer, uterine cancer, rectal cancer, thyroid cancer, melanoma, colorectal cancer, prostate cancer, ovarian cancer, and pancreatic cancer. In specific embodiments, the cancer is a glioma. In certain aspects, the glioma is recurrent malignant glioma. In some embodiments, the cancer is an astrocytoma. In certain embodiments, the subject who is a candidate for treatment is suffering from WHO grade II, WHO grade III, or WHO grade IV tumor. In some aspects, the tumor is an astrocytoma. In certain embodiments, the tumor is selected from grade II astrocytoma, AIII (IDH1 R132H mutant grade III astrocytoma), AIII-G (IDH1 wild-type grade III with characteristics of glioblastoma multiforme astrocytoma), or grade IV astrocytoma.

Grade IV astrocytoma is the highest grade glioma and is synonymous with glioblastoma (GBM). With a yearly incidence of 3 or 4 per 100,000 GBM is the most common malignant primary brain tumor in adults. Standard of care therapy—typically a combination of radiotherapy and chemotherapy using Temozolomide—does not work well and the outcome of GBM patients remains poor with a median life expectancy of 15-17 months. Advantageously, the methods here may be used to treat newly diagnosed brain cancers and may also be used to treat recurrent glioblastoma; for example, in patients previously treated with standard of care therapy. Thus, in certain aspects, the subject may be a newly diagnosed GBM subject or a recurrent GBM subject. The subject is preferably one who has not been previously treated with any therapeutic approaches that are immunosuppressive. In particular aspects, eligible subjects are over 18 years of age and have a Karnofsky score of 60 or above. Optionally, the subjects do not have bihemispheric disease and/or do not have an autoimmune disease.

Optionally, a subject who is a candidate for treatment may be identified by performing a tumor biopsy on the subject. In some embodiments, tumors from the subject are assayed for the presence of monocytes. In certain aspects, the monocytes include, but are not limited to, CD1 b+, CD14+, CD15+, CD23+, CD64+, CD68+, CD163+, CD204+, or CD206+ monocytes. The presence of monocytes in the tumors may be assayed using immunohistochemistry. In certain embodiments, a subject who is a candidate for treatment shows CD163+M2 cells greater than about 10%, about 15%, about 20%, about 25%, about 30%, about 35%, about 40%, about 45%, or about 50% of the subjects total peripheral blood mononuclear cells (PBMCs). In certain aspects, the subject shows CD163+M2 cells greater than about 20% of the subject's total PBMCs.

In yet other embodiments, a subject who is a candidate for treatment is identified by the presence of one or more cytokines in the serum of the subject. These cytokines include, without limitation, CXCL5, CXCL6, and CXCL7, IL6, IL7, IL8, IL10, IL11, IFN-γ, and HSP-70.

In yet other embodiments, a subject who is a candidate for treatment is identified by the presence of one or more growth factors in the serum of the subject. These growth factors include, without limitation, FGF-2, G-CSF, GM-CSF, and M-CSF.

In some embodiments, a subject who is a candidate for treatment with the biodiffusion chamber is identified by measuring the levels of a specific set of cytokines. In some embodiments, the subject has elevated levels of these cytokines in comparison to a healthy subject. As used herein, the term "healthy subject" refers to a subject not suffering from cancer or any other disease and not in need of treatment with the biodiffusion chamber.

In particular embodiments, the cytokines may be added to the chamber to augment the anti-tumor immune response. For example, the cytokines added to the chamber may be selected from the group consisting of CCL19, CCL20, CCL21, and CXCL12, and combinations thereof.

In certain embodiments, the circulating CD14+ monocytes have an elevated level of CD163 in comparison to a healthy subject. In some aspects, the levels of CD163 on the circulating CD14+ monocytes are elevated by at least about 2 fold, at least about 3 fold, at least about 4 fold, at least about 5 fold, at least about 10 fold, at least about 20 fold, at least about 30 fold, at least about 40 fold, at least about 50 fold, at least about 60 fold, at least about 70 fold, at least about 80 fold, at least about 90 fold, or at least about 100 fold in comparison to a healthy subject. In particular embodiments, the levels of CD163 on the circulating CD14+ monocytes are elevated by about 2 fold in comparison to a healthy subject.

In other embodiments, a subject who is a candidate for treatment has serum that polarizes undifferentiated monocytes towards M2 cells. In certain aspects, incubation of the subject's sera with undifferentiated monocytes induces the expression of one or more cell surface markers on the monocytes including, but not limited to, CD11b, CD14, CD15, CD23, CD64, CD68, CD163, CD204, and/or CD206. In other aspects, incubation of the subject's sera with undifferentiated monocytes elevates the expression of one or more cell surface markers on the monocytes in comparison to monocytes not incubated with the subject's sera. In certain aspects, the cell surface markers include, but are not limited to, CD11b, CD14, CD15, CD23, CD64, CD68, CD163, CD204, and/or CD206. In some aspects, the levels of one or more surface markers are elevated by at least about 1.3 fold, at least about 1.5 fold, at least about 1.8 fold, at least about 2 fold, at least about 3 fold, at least about 4 fold, at least about 5 fold, at least about 10 fold, at least about 20 fold, at least about 30 fold, at least about 40 fold, at least about 50 fold, at least about 60 fold, at least about 70 fold, at least about 80 fold, at least about 90 fold, or at least about 100 fold in comparison to undifferentiated monocytes not incubated with the subject's sera. In particular embodiments, the levels of one or more surface markers are elevated by about 2 fold in comparison to undifferentiated monocytes not incubated with the subject's sera. Monocytes polarized by a subject's sera may be measured using FACS.

Target Cells

Without being bound by theory it is thought that the AS ODN reduces the subjects M2 cells and/or inhibits polarization of cells into M2 cells by downregulating IGF-1R expression. In some embodiments, IGF-1R expression in M2 cells is downregulated by at least about 1%, at least about 2%, at least about 5%, at least about 10%, at least about 20%, at least about 30%, at least about 40%, at least about 50%, at least about 60%, at least about 70%, at least about 80%, at least about 90%, or at least about 95% in comparison to cells not treated with the antisense. IGF-1R expression in M2 cells may be measured by quantitative RT-PCR.

In some embodiments, IGF-1R expression in M2 cells remains downregulated in the subject for at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 3 weeks, at least about 4 weeks, at least about 5 weeks, or at least about 6 weeks after receiving one dose of the antisense.

In some aspects, the downregulation of expression of IGF-1R in M2 cells causes a selective reduction of M2 cells in a subject in comparison to cells not expressing IGF-1R. In certain embodiments, M2 cells in a subject are reduced by at least about 2%, at least about 5%, at least about 10%, at least about 20%, at least about 30%, at least about 40%, at least about 50%, at least about 60%, at least about 70%, at least about 80%, at least about 90%, or at least about 95% in comparison to a subject not treated with the antisense. In other embodiments, the M2 cell population is eliminated. For example, after implantation of the biodiffusion chamber, the M2 cell population may be about 1%, about 2%, about 5%, or about 10% of the population before implantation of the biodiffusion chamber. M2 cells in a subject may be measured using FACS. In certain aspects, after treatment the M2 cells are eliminated; i.e., undetectable by FACS. In other aspects, the decrease in M2 cells may be measured using a proxy assay; for example, serum from the subject may be obtained before and after treatment to assess its ability to polarize M2 cells. Following treatment with methods disclosed herein, the ability of the serum to polarize M2 cells is reduced by about 80% to about 100%, about 20% to about 60%, or about 10% to about 50%.

In some embodiments, targeting the expression of IGF-1R in M2 cells causes the M2 cells to undergo cell death. In certain embodiments, the cell death is necrosis. In other embodiments, the cell death is apoptosis. Apoptosis, for purposes of this disclosure, is defined as programmed cell death and includes, but is not limited to, regression of primary and metastatic tumors. Apoptosis is a programmed cell death which is a widespread phenomenon that plays a crucial role in the myriad of physiological and pathological processes. Necrosis, in contrast, is an accidental cell death which is the cell's response to a variety of harmful conditions and toxic substances. In yet other embodiments, targeting the expression of IGF-1R in M2 cells causes the M2 cells to undergo cell cycle arrest.

Kits

Preparation of a completed chamber requires multiple components and multiple steps. In another aspects of the disclosure kits containing components for practicing the methods disclosed herein are provided. In certain aspects, the kits comprise the chamber body, which may be present in one portion or in two halves. Items to seal the chamber may also be included including one or more membranes, glues and solvents (e.g., an alcohol, or 2 dichloroethane). Optionally, the membrane may by sonically welded onto the chamber to create a seal. The kits include the antisense ODN. Optionally, the ODN may be divided into two portions. A first portion to treat the cells after surgical removal from the subject, and a second portion to combine with the cells when introduced into the subject. Other optional kit items include media for culturing the cells, and antibiotics for preventing bacterial growth in the media.

Optionally, chambers in the kit may be pre-connected (e.g by suture) to each other using an eyelet or other device attached to the chamber and adapted to receive the connecting material. Advantageously, by pre-connecting multiple chambers, the desired number of chambers may be readily introduced and removed by the surgeon.

EXAMPLES

Example 1

Vaccination with Autologous Tumor Cells and IGF-1R AS ODN in Patients with Recurrent Glioblastoma Criteria and Study Objective Twelve subjects were enrolled for treatment after failure from standard therapy. Each patient met the following criteria: age >18, a Karnofsky performance score of 60 or better, and no co-morbidities that would preclude elective surgical re-resection. The subjects were treated by 24 hour implantation in the rectus sheath of ten biodiffusion chambers containing irradiated autologous tumor cells and IGF-1R AS ODN with the objective of stimulating tumor immunity. Patients were monitored for safety, clinical and radiographic as well as immune responses. Study objectives included assessment of safety and radiographic responses as well as exploratory objectives looking at immune function and response.

TABLE 1

Summary of Patients enrolled

| Subject | Age | KPS | Time between surgeries (weeks) | Chambers (No.) | Original lymphocyte count (cells/mm2) | Lymphocyte count at enrollment (cells/mm2) | Previous treatment | IDH-1&IDH-2 mutation/ MGMT methylation |
|---|---|---|---|---|---|---|---|---|
| TJ01 | 39 | 70 | 177 | 10 | N/A | 400 | S, RT + TMZ, Bev | −/NA |
| TJ02 | 57 | 80 | 90 | 9 | N/A | 1570 | S, RT + TMZ | −/methylated |
| TJ03 | 75 | 70 | 32 | 7 | 700 | 300 | S, RT + TMZ | −/NA |
| TJ06/R[1] | 66 | 80 | 54 | 8 | 2000 | 1300 | S, RT + TMZ | −/NA |
| TJ07 | 43 | 80 | 215 | 10 | 500 | 430 | S, RT + TMZ, Bev; RTOG 0525 | +/methylated |

TABLE 1-continued

Summary of Patients enrolled

| Subject | Age | KPS | Time between surgeries (weeks) | Chambers (No.) | Original lymphocyte count (cells/mm2) | Lymphocyte count at enrollment (cells/mm2) | Previous treatment | IDH-1&IDH-2 mutation/ MGMT methylation |
|---|---|---|---|---|---|---|---|---|
| TJ08 | 55 | 80 | 52 | 8 | 1000 | 500 | S, RT + TMZ | −/TNS |
| TJ09 | 57 | 80 | 61 | 7 | 1400 | 300 | S, RT + TMZ, RTOG 0929 | −/ unmethylated |
| TJ10 | 47 | 60 | 376 | 7 | N/A | 1800 | S, RT + TMZ, Bev | −/methylated |
| TJ11 | 39 | 70 | 32 | 11* | 2400 | 200 | S, RT + TMZ | −/TNS |
| TJ12 | 60 | 80 | 74 | 7 | 1100 | 600 | S, RT + TMZ, Panobinostat | −/TNS |
| TJ13 | 64 | 80 | 182 | 11 | N/A | 2100 | S, RT + TMZ | −/methylated |
| TJ14/R | 77 | 90 | 30 | 9/11 | 1800 | 1100 | S, RT + TMZ | − unmethylated |

[1]Compassionate retreatment;
*Protocol amendment to include control chamber filled with phosphate buffered saline;
S: surgery;
RT: radiation therapy;
TMZ: temozolamide chemotherapy;
Bev: bevacizumab chemotherapy;
IDH-1: isocitrate dehydrogenase-1;
NA: not available;
TNS: tissue not sufficient Experimental Protocol Tumor tissue was surgically removed from patients using a tissue aspirator (NICO Myriad®) and placed into sterile tissue traps. The sterile tissue traps were transferred to a designated BSL-2 facility, where the tumor tissue was processed and placed into biodiffusion chambers. The biodiffusion chambers were irradiated prior to implantation.

The day following surgery to remove tumor tissue, ten irradiated biodiffusion chambers were implanted into the rectus sheath of the subjects. After 24 hours, they were removed.

The biodiffusion chambers contained autologous tumor cells removed at surgery. Prior to being added to the biodiffusion chambers, the cells were pretreated overnight (approx. 12-18 hours) with a first amount (4 mg/ml) of an 18-mer IGF-1R AS ODN with the sequence 5'-TCCTCCG-GAGCCAGACTT-3' (NOBEL). Based on data showing that the AS ODN has immunomodulatory properties, a second amount (2 μg) of exogenous NOBEL antisense was added to the chambers (C-v), and the chambers were subsequently irradiated. Ten chambers were implanted in each patient. An eleventh control chamber containing PBS (C-p) was also implanted.

Radiological Assessments

Serial imaging assessments were performed on Philips 1.5T and 3T MRI scanners and a GE 1.5T MRI scanner. Routine anatomic MRI features were rated by two neuroradiologists in all 12 patients. Physiologic MRI techniques of dynamic susceptibility weighted (DSC) MR perfusion and 15-direction diffusion tensor imaging (DTI) were also utilized. MR perfusion and DTI post processing was performed on Nordic Ice workstation (v.2.3.14). rCBV was calculated in relation to contralateral normal white matter. Averaged diffusion coefficient (mean diffusivity) was calculated from the DTI data.

Immunological Assessments

Plasma leukopheresis was performed one week before surgery for baseline assessment of immune function. Blood was obtained post-operatively on days 7, 14, 28, 42, 56, and every 3 months after vaccination. Sera and cell fractions were separated by centrifugation and cells were treated with red blood cell lysis buffer. White blood cells were either quantified by flow cytometry or stored in DMSO at −80° C. Serum samples were also stored at −80° C. Flow cytometry was performed using an EasyCyte 8HT (Millipore) and fluorescently-conjugated mAb specific for human CD4, CD8, CD11b, CD14, CD16, CD20, CD45, CD56, CD80, CD83, and CD86 (all from BD Biosciences), and CD163 (R&D Systems). Post-collection analysis was performed with FlowJo software (Tree Star Inc, Ashland, Oreg.). Serum cytokine factors were quantified using Luminex bead arrays (human cytokine/chemokine panels I, II, and III from Millipore) and HCMBMAG/MILLIPLEX Mag Cancer multiplex assay (emdmillipore.com). This included 6 serum markers for glioma related to stem cell function including DKK-1, NSE, Osteonectin, Periostin, YKL-40, and TWEAK. Serum nitrate levels were assayed according to the Greiss method (Green L. C., et al., 1982, Anal Biochem 126:131-8). T cell stimulation was performed with phorbol 12-myristate, 13 acetate (PMA) and ionomycin as previously described (Verbrugge, I., et al., 2012, Cancer Res, 72:3163-74).

Cytokine/chemokine levels in tumor cell supernatant (SN) and explanted chamber contents were analyzed by Luminex kits as designated above. Membranes from paired vaccine and control chambers were embedded in paraffin for standard immunopathologic examination.

Tumor tissue sections were assessed by immunohistochemistry for GFAP (glial fibrillary acidic protein), IGF-1R, CD163, CD14, VWF (Von Willebrand Factor), CD4, and CD8 or fluorescence immunohistochemistry adapting the method described in Emoto, K., et al., 2005, Histochem Cytochem 53:1311-21). Immunopositive cells were counted quantitatively with Aperio or qualitatively by an experienced neuropathologist (LCK) using an ordinal scale from 0 (no staining) to 6 (strong diffuse staining) with staining intensity rated as low, moderate and strong and staining patterns described as focal or diffuse. Post-mortem autopsy was limited to examination of the brain and findings were compared to archival paraffin blocks of previously treated or untreated glioblastomas diagnosed at autopsy. Both canonical in vitro polarization of naïve monocytes or mixing experiments involving naive monocytes co-incubated with serum derived from trial subjects at enrollment were performed as previously described (Harshyne, LA, et al., 2015, Neuro Oncol 18(2):206-15; Solinas, G., et al., 2010, J Immunol 185:642-52).

Statistical Analysis

The level of statistical significance between quantitative measures in different samples was determined by a two-tailed unpaired t-test or matched pairs t-test with $p<0.05$. Survival analysis was performed by Kaplan-Meier analysis and significance established by log rank comparisons. All statistical analysis including mixture discriminant analysis was performed with JMP v. 11 software (SAS, North Carolina).

Safety Assessment and Clinical Course

Only one severe adverse event (SAE) was related to the protocol (femoral vein thrombosis after leukopheresis). Nine patients succumbed to tumor progression while three patients died from other causes. Five autopsies were performed.

Median overall survival from initial diagnosis was 91.4 weeks (FIG. 2a) which compared favorably to other recurrent glioma immunotherapy trials. Two significantly different protocol survival cohorts of 48.2 and 10 weeks were identified as longer and shorter survival cohorts, respectively (FIG. 2b). Excluding one outlier (Patient TJ03), we documented a significant correlation between protocol survival and degree of lymphopenia at enrollment (FIG. 2c). Comparison of CBC values at initial diagnosis and at protocol enrollment indicated that the mean lymphocyte count had dropped significantly (65%) after standard therapy (N=8, p=0.012, paired t-test).

Radiographic Responses

Figure 3B:
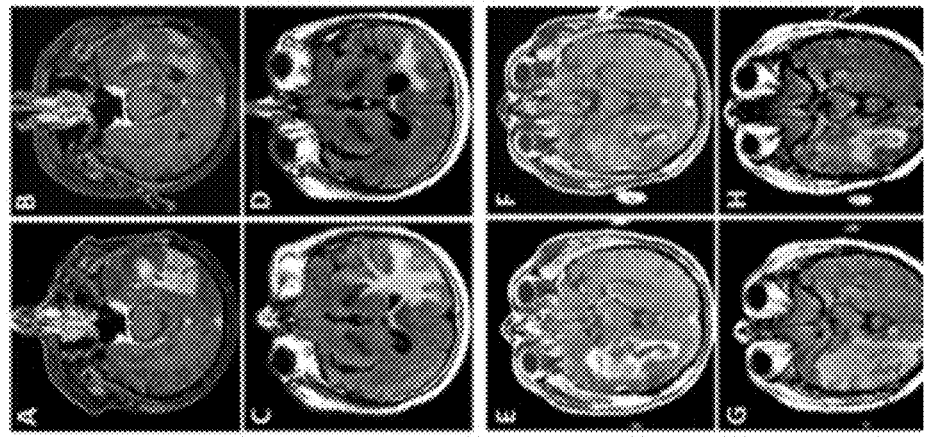
Figure 3A:
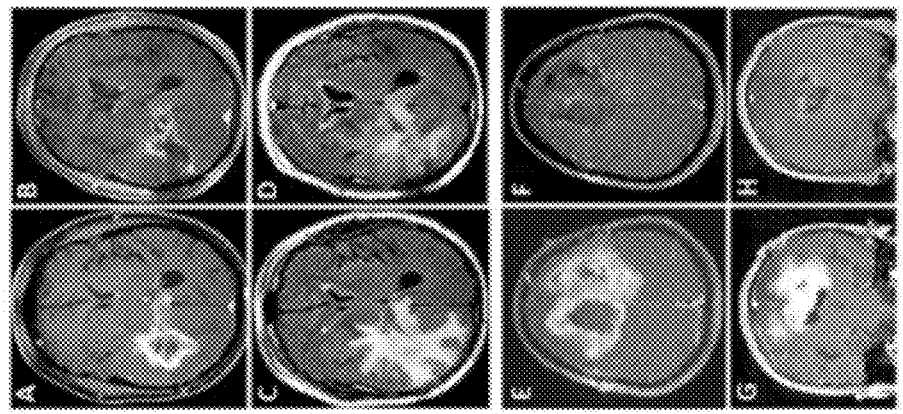

Routine MRI features were assessed and rated by two neuroradiologists (K.S.T. and A.E.F.). In the longer cohort, diminished size of enhancement and FLAIR envelope at the primary tumor site were observed, along with slower progression. Examples of anatomic responses in both cohorts is shown in FIGS. 3a and 3b. Physiologic MRI measurements augmented these anatomic observations. Sequential DSC MR perfusion was performed in 7 patients, including 3 longer-term survivors (Patients TJ03, TJ06, and TJ09) who had a paradoxical increase in relative Cerebral Blood Volume (rCBV) while improving clinically; however, this effect was transient and there was a more sustained decrease in rCBV. Sequential 15 directions DTI data included two long-term survivors (Patients TJ03 and TJ06) who showed apparent diffusion co-efficient (ADC) values increasing in the affected hemisphere, reflecting loss of tumor cellularity associated with disease regression. We noted a high correlation between the paradoxical rCBV response and increasing ADC not seen in the short cohort (FIGS. 3c and 3d). Corresponding levels of serum nitrate in the longer cohort reflected the likelihood that an inflammatory response had been initiated (data not shown).

Examination of Explanted Chambers v. Peri-Operative Serum by Survival Cohort

Figure 4A:
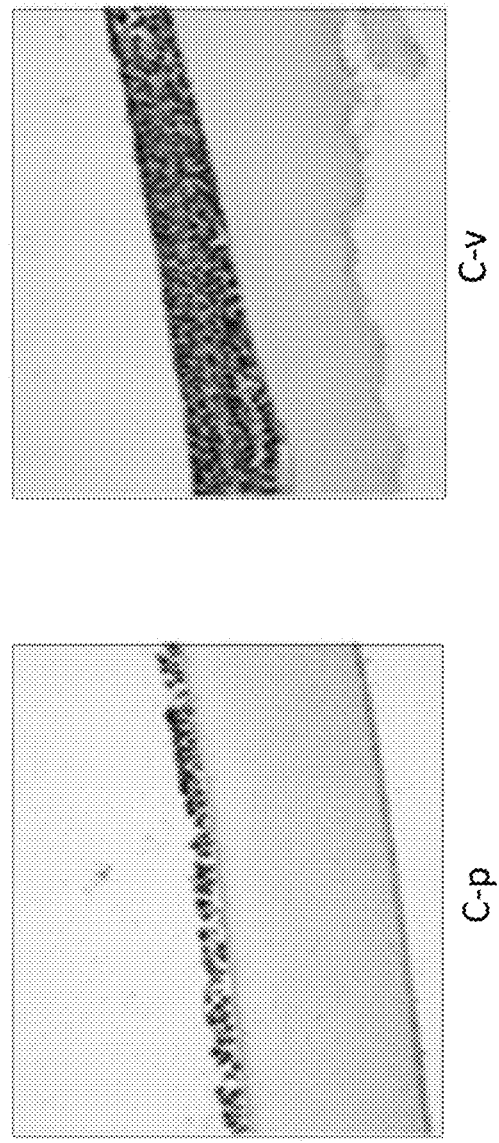
FIGS. 4a-4c depict an examination of the explanted chambers by survival cohorts.

Explanted chambers were structurally intact with no viable cells. Outer surfaces of membranes from both C-p and C-v chambers were coated with CD15+ and CD163+ cells, but with dramatically increased numbers on C-v membranes (FIG. 4a).

For the entire study cohort, analysis of the chamber soluble contents revealed significant elevations of a number of growth factors and cytokines/chemokines over matched perioperative serum levels, many of which are well-documented in the glioma tumor microenvironment (TME). Thirty two of 78 cytokines/chemokines tested were significantly elevated over serum and matched pairs analysis revealed significant elevations of cytokines as noted in Table 2 below.

TABLE 2

Chamber Values by Survival Cohort

| Cytokines/chemokines present in explanted chambers | | | | |
|---|---|---|---|---|
| cytokine | longer | short | P value | Fold |
| VEGF | 4382 | 1207 | .001 | 3.63 |
| PDGF-AA | 272 | 90 | .02 | 3.02 |
| IL-11 | 1096 | 181 | .002 | 6.06 |
| CCL7/MCP-3 | 3293 | 1581 | .001 | 2.08 |
| CCL5/RANTES | 1484 | 169 | .003 | 8.78 |
| CCL22/MDC | 385 | 1847 | .02 | 0.208 |
| I-309 | 4.47 | 11.5 | .02 | 0.389 |
| MW-1d | 311 | 182 | .002 | 1.71 |

| Chambers: Matched pairs (chambers v. serum) | | | | |
|---|---|---|---|---|
| cytokine | longer | P value | short | P value |
| VEGF | 4028/81 | .02 | 1178/80 | .24 |
| PDGF-AA | 236/1803 | .06 | 80/1431 | .0011 |
| IL-11 | 958/54 | .11 | 181/25 | .047 |
| CCL7/MCP-3 | 3276/29 | .005 | 1581/18 | .0004 |
| CCL5/RANTES | 1194/5571 | .004 | 175/6201 | <.001 |
| CCL22/MDC | 412/366 | .8 | 1847/348 | .09 |
| MW-1d | 294/523 | .02 | 182/473 | .0095 |

| Cancer markers present in explanted chambers | | | | |
|---|---|---|---|---|
| marker | longer | short | P value | Fold |
| DKK1 | 629 | 1389 | .02 | 0.452 |
| NSE | 7304 | 11712 | .03 | 0.624 |
| osteonectin | 1022 | 1729 | .02 | 0.591 |
| periostin | 286 | 224 | .10 | 1.27 |
| TRAP5 | 1421 | 2441 | .007 | 0.582 |
| OPG | 481 | 1409 | .002 | 0.341 |
| YKL40 | 8615 | 12889 | .13 | 0.668 |
| TWEAK | 190 | 171 | .87 | 1.11 |

| Chambers: Matched pairs (chambers v. serum) | | | | |
|---|---|---|---|---|
| Marker | Longer | P value | short | P value |
| DKK1 | 214/539 | .16 | 457/1389 | .01 |
| NSE | 6263/2182 | .30 | 11723/1902 | .01 |
| osteonectin | 886/953 | .70 | 1729/956 | .04 |
| periostin | 249/532 | .03 | 224/421 | .004 |
| TRAP5 | 998/1915 | .13 | 2442/1940 | .15 |
| OPG | 419/205 | .48 | 1409/168 | .01 |
| YKL40 | 7300/12559 | .19 | 12191/5574 | .03 |
| TWEAK | 142/310 | .15 | 324/217 | .53 |

These elevations were interpreted as either cytokines/chemokines produced by the encapsulated tumor cells or factors produced by the local innate immune response that had diffused into the chambers.

Figure 4B:
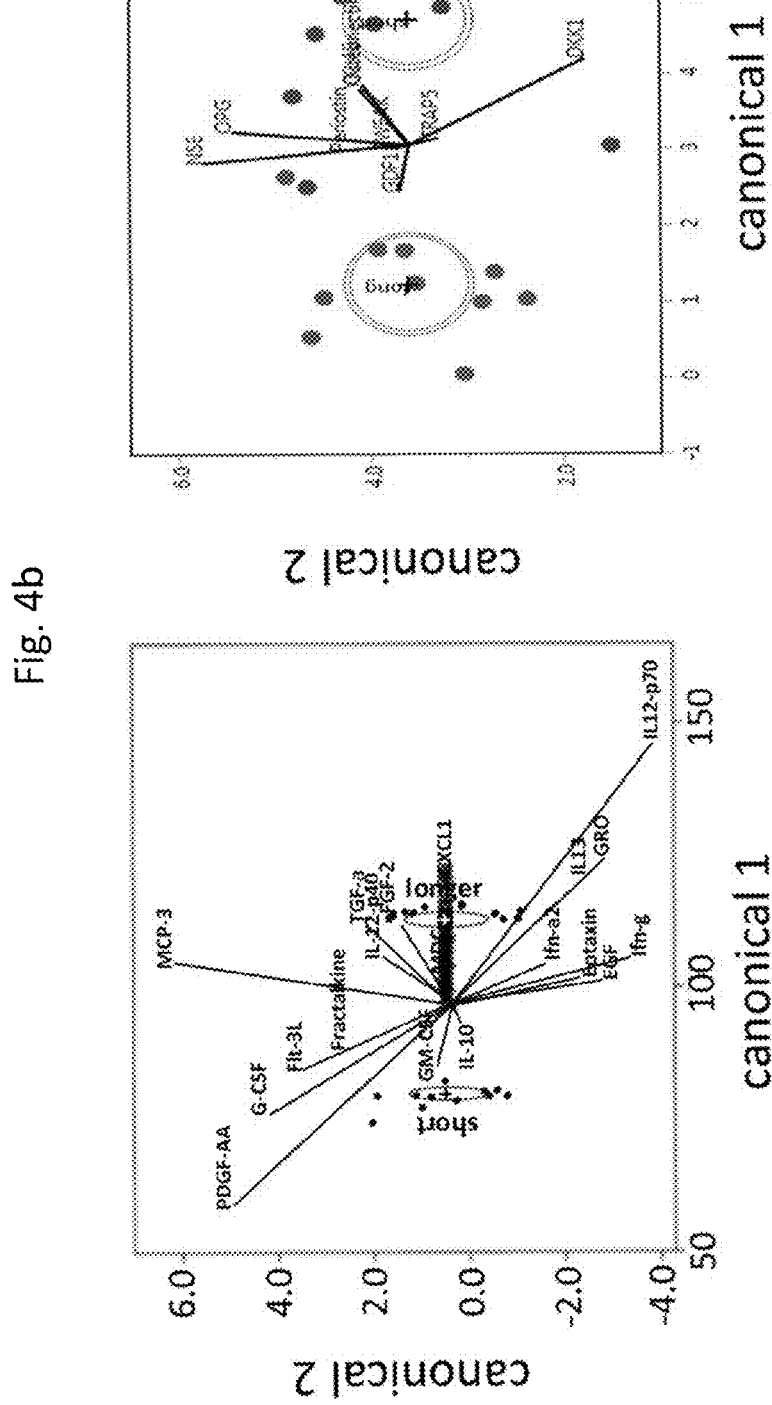

Analysis of factors in chambers between survival cohorts revealed significant chamber elevations of VEGF, PDGF-α, IL-11, CCL5, MCP-3, and MIP-1d in the longer cohort while a number of soluble cancer markers were significantly elevated in the short cohort including NSE, osteonectin, and YKL40. Mixture discriminant analysis independently identified these cohort differences (FIG. 4b).

Figure 4C:
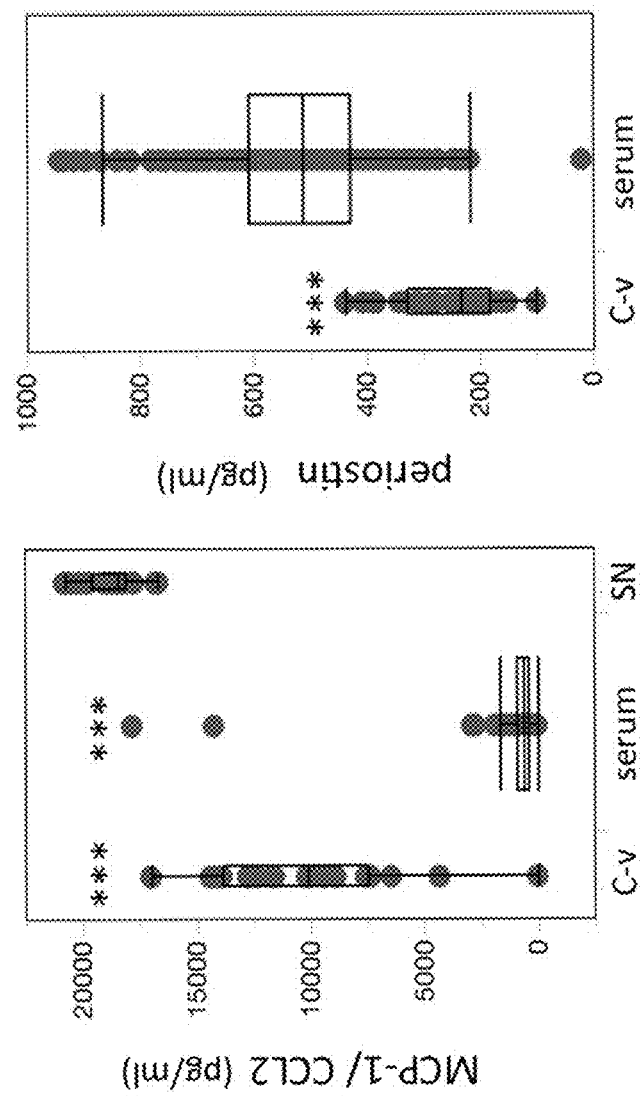

For both cohorts, both Periostin and CCL2 levels were significantly lower in the chambers (C-v) than serum or SN values, suggesting elimination of cells producing these chemokines in the chambers (FIG. 4c).

Serum Cytokines/Chemokines and PBMC after Vaccination by Survival Cohort

Levels of 24 of the 78 cytokines/chemokines assessed were significantly higher in serum from the longer cohort compared to the short cohort, as shown in Table 3 below.

TABLE 3

Serum Values by Cohort
Cytokine/chemokine serum values (long cohort v. short cohort)

| cytokine | long | short | P value |
| --- | --- | --- | --- |
| CCL21 | 279 | 148 | .0007 |
| CTACK | 1313 | 1009 | .01 |
| Flt-3L | 28 | 10.6 | .02 |
| Fractalkine | 102 | 73 | .004 |
| I-309 | 10.2 | 6.7 | .02 |
| IL-1RA | 59 | 36 | .001 |
| IL-10 | 15 | 5 | .003 |
| IL-12-p40 | 41 | 3 | .001 |
| IL-13 | 8.6 | 3.1 | .005 |
| IL-15 | 11.4 | 4.6 | .0005 |
| IL-1a | 41 | 3.6 | .003 |
| IL-1b | 6.04 | 2.46 | .003 |
| IL-2 | 7.18 | 2.87 | .006 |
| IL-3 | 5.06 | 3.13 | .007 |
| IL-5 | 2.8 | 1.35 | <.0001 |
| IL-9 | 5.61 | 3.07 | .005 |
| MCP-3 | 28 | 17 | .002 |
| MIP-3b | 826 | 304 | .005 |
| MIP-1b | 33 | 24 | .01 |
| SCF | 11.8 | 3.6 | .007 |
| CXCL12 | 516 | 3.6 | .008 |
| TGF-α | 2.91 | 1.93 | .005 |
| TNF-α | 10.8 | 5.9 | <.0001 |
| TPO | 110 | 55 | .02 |

A spike in serum CCL2 occurred after surgery but was absent at re-operation in two patients. CCL2 levels remained significantly higher throughout the post-operative period in the short cohort. These post-operative spikes were highly correlated with TNF-α spikes (FIGS. 5 and 6).

Actual CD4 and CD8 T cell counts as well as dendritic cell (DC) counts were significantly higher in the longer cohort and perioperative CD14+16− counts were significantly lower compared to the short cohort. There was a significant correlation between CD4 and DC cells and between CD4 and CXCL12 only in the longer cohort. Day 14 PBMC from the longer survival subjects manifested significantly higher Th-1 cytokine production including IFNγ after stimulation with PMA and ionomycin than the short cohort (data not shown). Coordinated changes between circulating levels of T cells, monocytes, and pro-inflammatory chemokines/cytokines after vaccination were seen in three of four subjects. The highest correlation was noted between total monocyte count and CD14+16− monocyte levels (FIGS. 5b and 5d). An inverse relationship between circulating T cell and monocyte numbers was also noted in the longer cohort (FIG. 5) without significant differences in the short cohort (FIG. 6). Predictable and reciprocal relationships between immunosuppressive and pro-inflammatory cell populations as well as monocyte-chemokine relationships suggested more immune fitness in the longer cohort.

Examination of Paraffin Sections

Figure 7A:
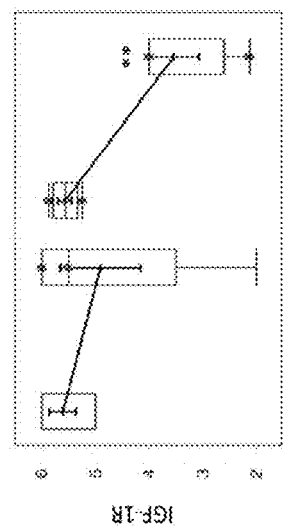
Figure 7B:
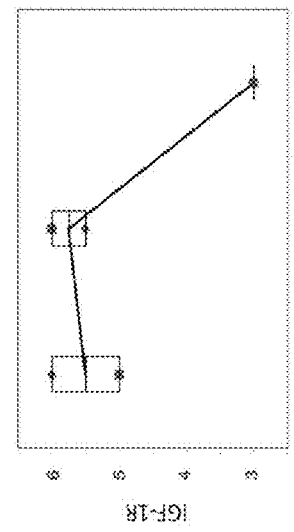

Paraffin sections from surgical interventions through autopsies were available for analysis in four cases allowing us to look at the post-vaccination TME. We compared trial autopsies to autopsies from re-operated and untreated GBM patients (FIG. 7). Immunostains revealed a significant decrease in IGF-1R positive cells after vaccination in matched pairs that was corroborated by fluorescence immunohistochemistry (FIGS. 7a and 7g). Qualitative comparisons to either recurrent or untreated glioma autopsies revealed abundant CD163 TAMs and IGF-1R+ cells in both, diminishing any concern of cell loss as autopsy artifact (FIG. 7g).

Figure 7C:
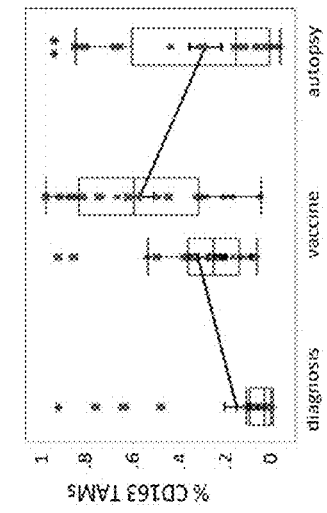
Figure 7G:
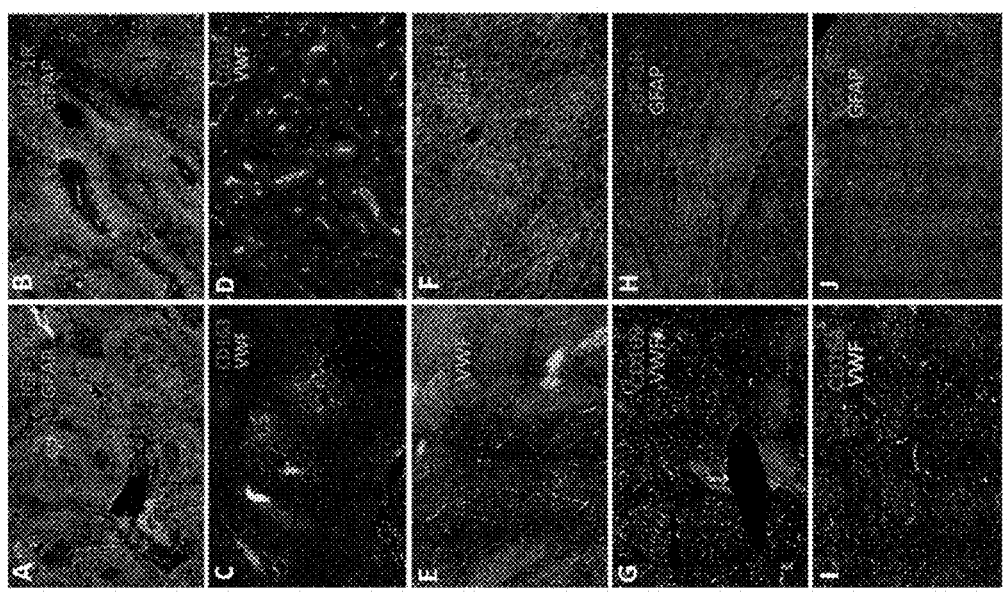
Figure 7H:
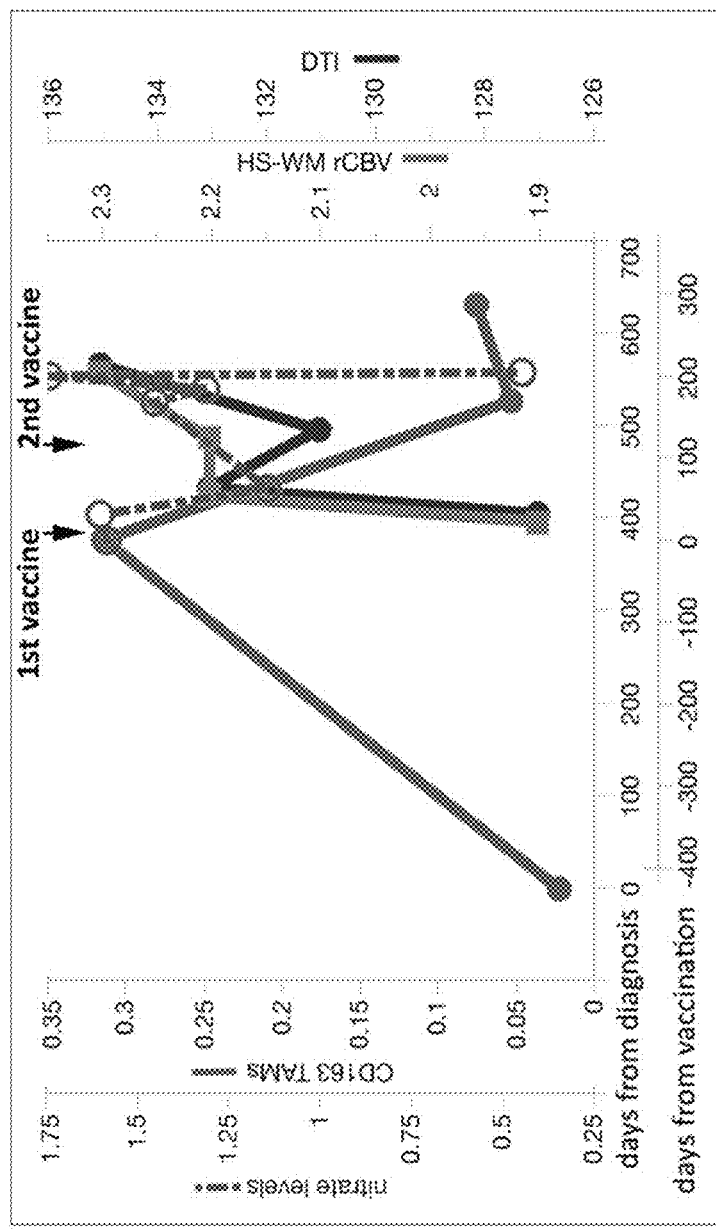

CD163 TAMs peaked at recurrence in matched comparisons to both initial surgery and autopsy (FIGS. 7c and 7g). Patients TJ06 and TJ10 supported these trends with evaluable samples through all phases of treatment (FIGS. 7b and 7d). In the case of TJ06, CD163 cells dropped after the second vaccination and persisted through autopsy. This decrease correlated inversely with rCBV and ADC values as well as serum nitrate levels all of which increased after each vaccine (see FIG. 7f).

Exploring an association with peripheral monocytes, a strong correlation was noted between peripheral CD163+ monocytes and CD163 TAMs (FIG. 7e) in the short cohort not seen in the longer cohort (FIG. 7f).

We did not see the emergence of T cell populations in the TME after vaccination in either cohort.

Coincubation of Subject Serum with Undifferentiated Monocytes

Figure 8B:
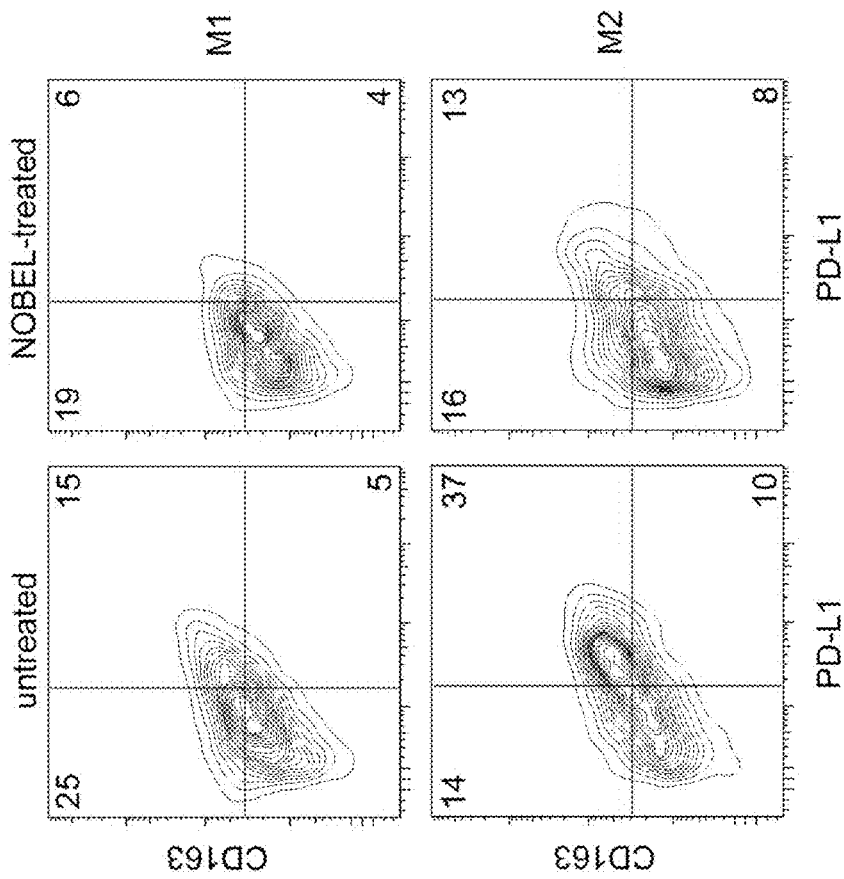
FIGS. 8a-8d depict differentiation of immature monocytes by cytokines or serum from study subject.
Figure 8A:
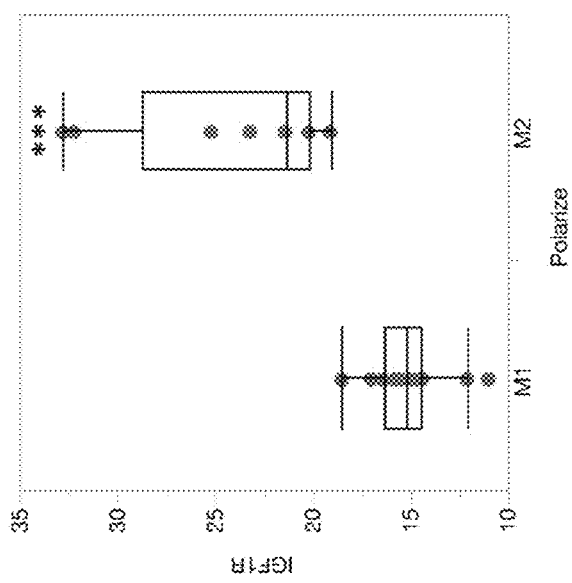

To explore the genesis of the circulating CD163+ monocytes in the patients we first polarized naïve monocytes with canonical M1 and M2 cytokines IFN-γ and IL-4, respectively. We observed upregulation of IGF-1R with M2 polarization only (FIG. 8a). The M2 polarized CD163+ population was selectively knocked down when incubated with IGF-1R AS ODN (FIG. 8b).

Figure 8D:
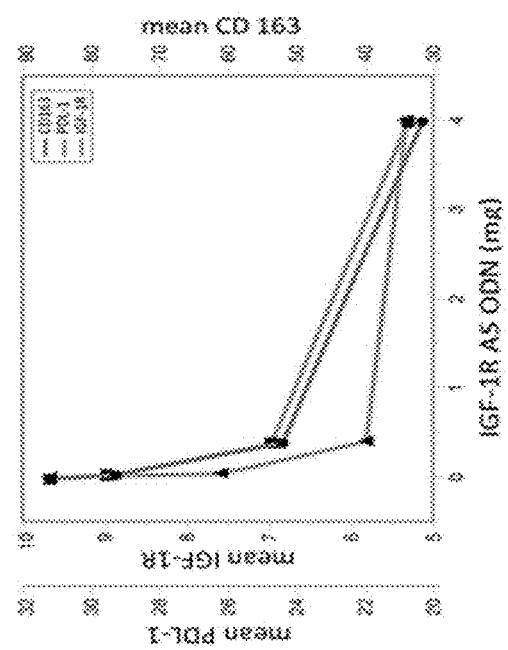
Figure 8C:
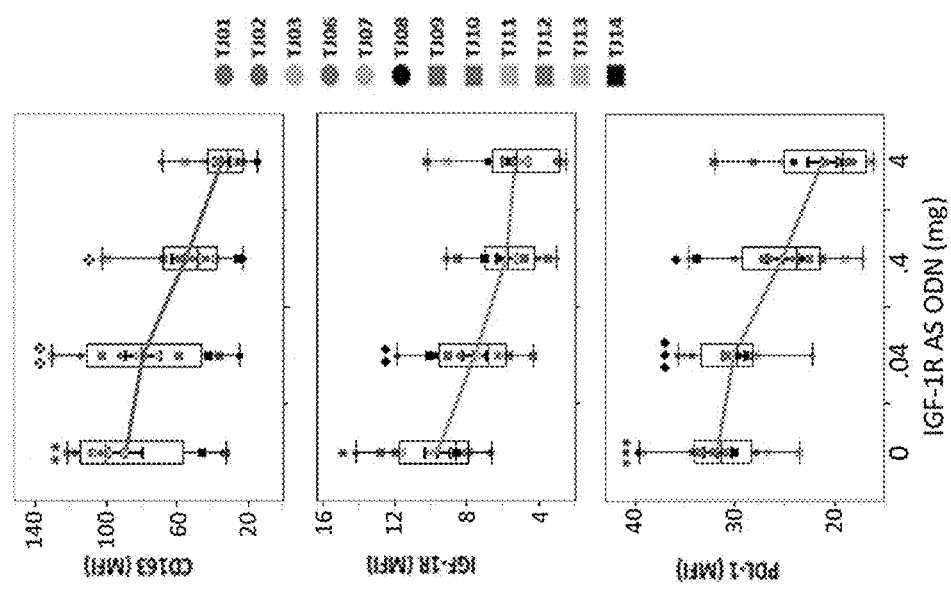
Figure 9A:
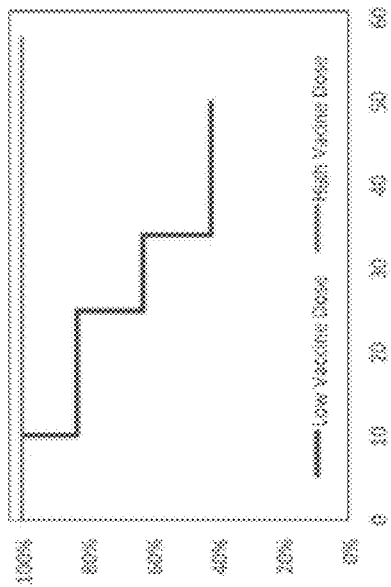
FIGS. 9a-9d show that compared to standard of care in the first interim analysis, there were significant improvements in both progression-free survival and overall survival.
Figure 9B:
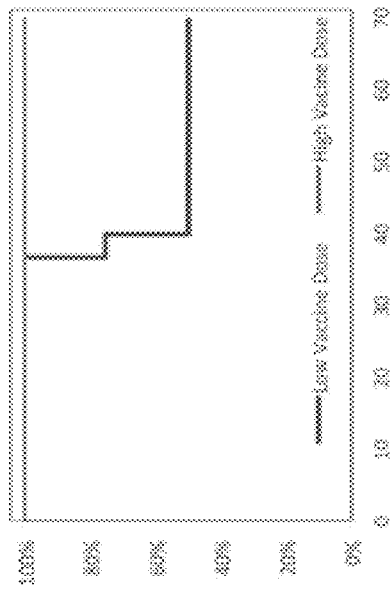
Figure 9C:
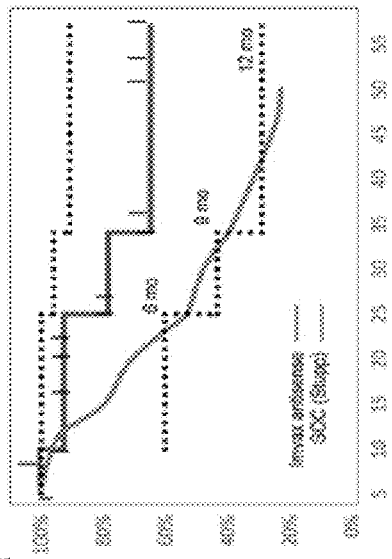
Figure 9D:
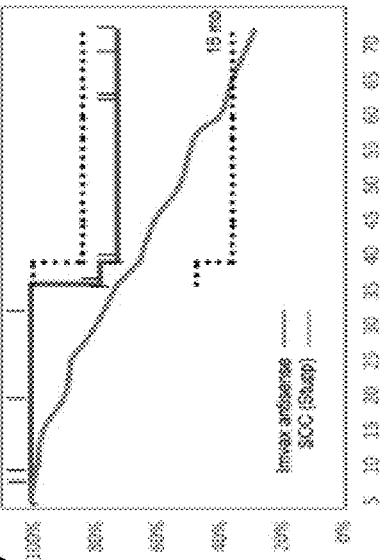
Figure 10A:
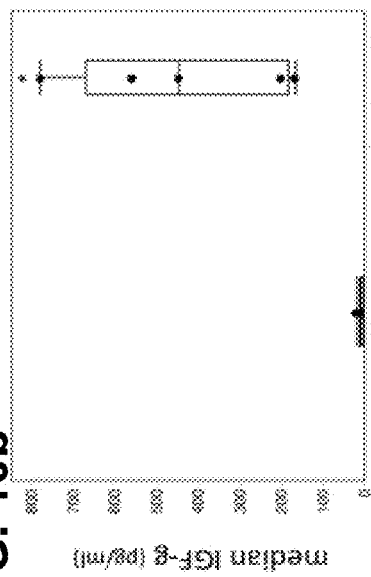
FIGS. 10a-10d depict a summary of the Phase 1b study and a comparison of interferon-gamma levels to the prior trial and between cohorts within the trial.
Figure 10B:
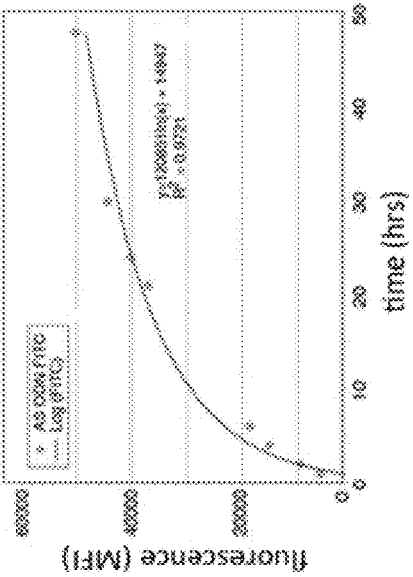
Figure 10C:
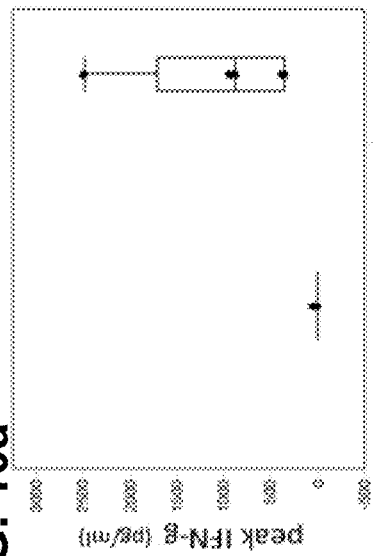
Figure 10D:
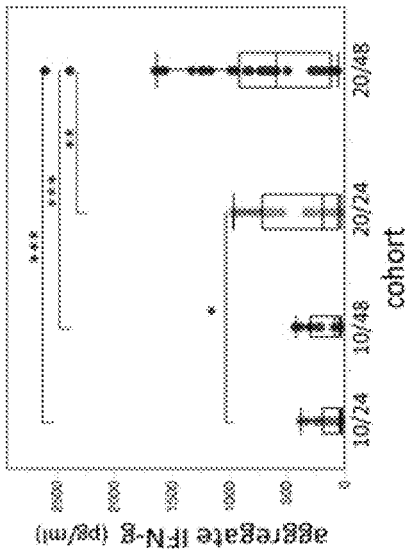
Figure 11A:
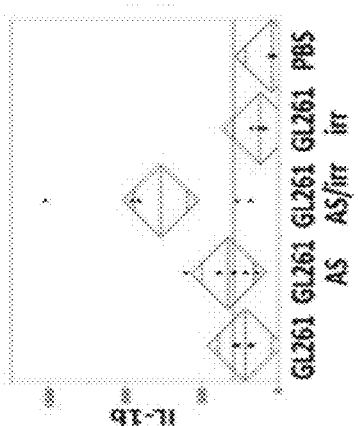
Figure 11B:
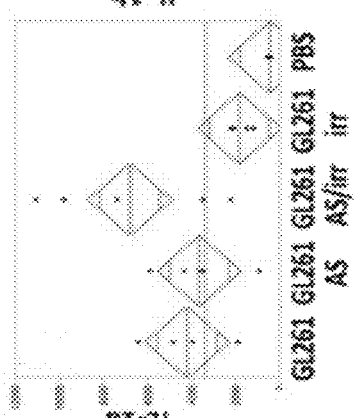
Figure 11C:
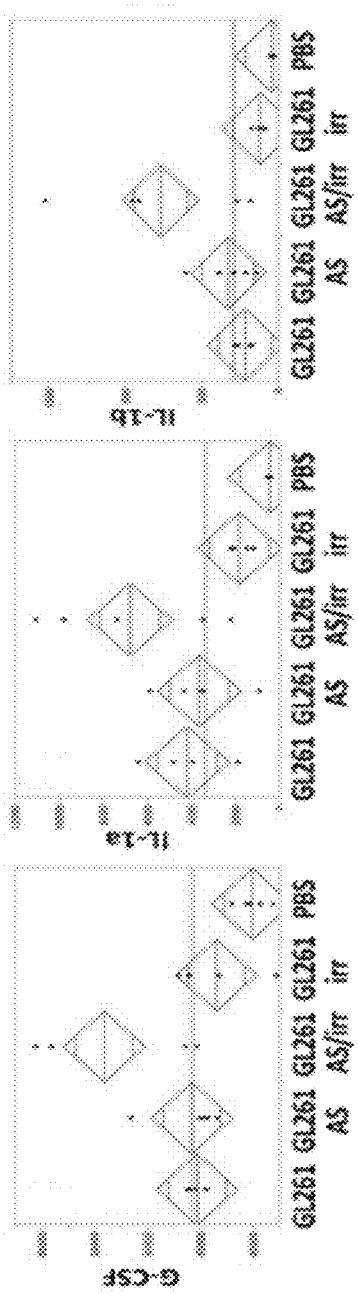
Figure 11E:
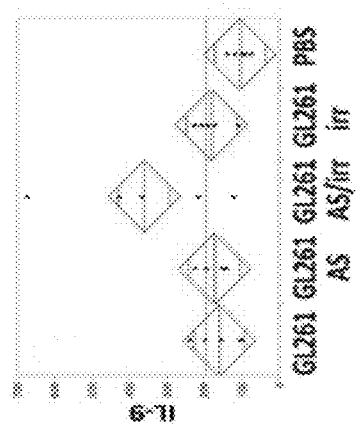
Figure 11D:
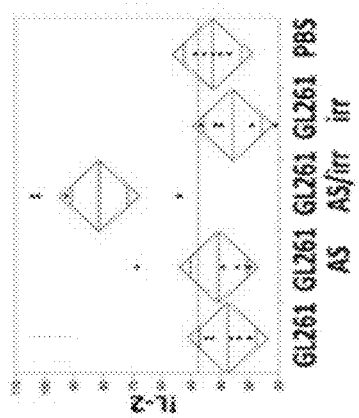

Subsequently, we coincubated naïve monocytes with serum obtained from all study subjects and documented the emergence of CD163+ cells that co-expressed both IGF-1R and PDL-1 (FIG. 8c). When treated with IGF-1R AS ODN, cells expressing IGF-1R, PD-L1 and CD163 were significantly knocked down in a parallel and dose-dependent manner (FIG. 8c) summarized in FIG. 8d.

DISCUSSION

The revised autologous cell/chamber-based glioblastoma multiforme (GBM) vaccination trial did not raise any significant safety concerns.

We identified two significantly different survival cohorts with different responses to this vaccine paradigm. See FIGS. 5 and 6. Longer cohort subjects typically exhibited elevated levels of tumor-specific antibody isotypes and cytokines/chemokines commonly associated with Th1 immunity including IgG1, IgG3, IL12, CXCL10, CXCL12, CCL7, CCL19, and CCL21 following surgery and vaccination. Elevated levels of these cytokines/chemokines were not seen in the short cohort. Accordingly, levels of cytokines/chemokines commonly associated with Th1 immunity (e.g., IgG1, IgG3, IL12, CXCL10, CXCL12, CCL7, CCL19, CCL21) may be assessed following surgery/vaccination to predict survival and to inform further treatment strategies.

Of interest, CCL21 and CXCL12 synergize with CpG adjuvants and enhance the migratory and T cell stimulatory capacity of DCs in a vaccination paradigm. Also, noted elevations of GM-CSF, IL-6, Flt-3L and SCF in the longer cohort could enhance DC proliferation, and may have contributed to the significant 76% increase in pDCs after vaccination. The significant elevations of CD4 cells as well as correlations between CD4 cells, pDC, and the cytokine CXCL12 also suggests the successful induction of T cell proliferation facilitated by CXCL12 during immune synapse.

Patients in the short survival cohort were typically subjected to a longer course of treatment prior to vaccination, leading to lymphophenia. Accordingly, vaccination is most effective when administered to patients with normal lymphocyte levels, i.e. non-lymphopenic patients. The treatment-induced lymphopenia and the lower CD4:CD8 ratio could also be ascribed to temozolamide. (Standard of care included conformal radiation with concomitant temozolamide followed by maintenance temozolamide initiated at 6 weeks post-surgery). A consequence of longer overall survival would include chronic exposure to tumor antigens and ongoing glioma inhibitory signals leading to T cell exhaustion. Similarly, monocytes/macrophages had an apparent lack of responsiveness with only modest fluctuations after vaccination but a distinct correlation between peripheral CD14+16− cells and TAMs. TAMs have been associated with CCL2 production and this correlation could reflect a closed loop amplification promoting tumor growth. Supporting this, elevated serum CCL2 levels found in the short cohort have been associated with the mesenchymal gene expression profile and a poor prognosis in glioma patients.

The explanted chambers provided a unique snapshot of the encapsulated TME and its commerce with the initial immune response. Cytokine elevations in the longer cohort chambers collectively indicated that the vaccinations induced a Th1 response, and serum from this cohort contained tumor-specific antibody isotypes associated with Th1 immunity. Mixture discriminant analysis established associations with IFN-$\gamma$, TNF-$\alpha$, and IL12 production.

In contrast, the short cohort chambers had greater elevations of cancer markers reflecting the emergence of glioma stem cell (GSC)-associated resistance after standard therapy. One conspicuous exception was periostin levels that were dramatically lower in all chambers compared to paired serum values. Tumor-promoting cell populations in glioma include TAMs and GSC, the former supporting the latter in the same perivascular niche (Zhou, W., et al., 2015, Nat Cell Biol 17:170-82) and both representing strategic targets for treatment. M2 macrophages recruited by GSC-secreted periostin play a critical role in tumor growth and their elimination would have therapeutic advantage. The reduction in periostin levels in chambers containing treated tumor cells suggests that GSCs secreting this factor themselves are a target for IGF-1R AS ODN.

Notably, despite pre-existing immunosuppression (due to prior treatment according to the standard of care) we documented radiographic and clinical improvements supported by a pro-inflammatory response after vaccination in 4 of 12 patients. These patients also had a significant survival advantage on protocol. Exploring this survival difference further we noted a higher level of immune fitness in the longer cohort.

IGF-1R reduction after vaccination was associated with longer protocol survival in some subjects. Without being bound to any particular theory, it is possible that the IGF-1R+ cell populations are knocked down as a consequence of type 1 immune mechanisms promoted in these individuals by the vaccination paradigm.

As we have shown in vitro, IGF-1R AS ODN inactivates the CD163+ cells contained in the vaccine preparation, thereby eliminating their immunomodulatory factors and promoting type 1 immunity. Moreover, any IGF-1R AS ODN that diffuses out of the vaccine chamber has a similar effect on M2 macrophages that it reaches. This represents a novel platform in which cells expressing a variety of tumor-promoting ligands and factors, including PDL-1, other immunomodulatory factors, angiogenic factors, nutrient support, and tumor invasiveness, are targeted.

Differences in the radiographic observations between the longer and short survival patient cohorts provide further support for the concept that the vaccination paradigm has an impact on the broader glioma TME. Higher rCBV values are typically associated with tumor progression, and MR perfusion had only transient increases in the longer cohort, a finding not previously described. ADC measurements differentiated tumor progression (lower values) from what we interpreted as cell loss (higher values). Since this vaccination paradigm is associated with loss of both IGF-1R cell and CD163+ TAM populations, it is possible that rising ADC values are a reflection of this.

In summary, we have established the safety profile of an improved combination glioma vaccine product and have documented alterations in immune parameters associated with clinical and radiographic improvements. With the promise of knocking down specific monocyte cell populations that promote tumor growth (e.g. CD163+ cells that co-express IGF-1R), this paradigm offers a treatment scheme that does not result in immune compromise.

Summary of Results

Figure 2A:
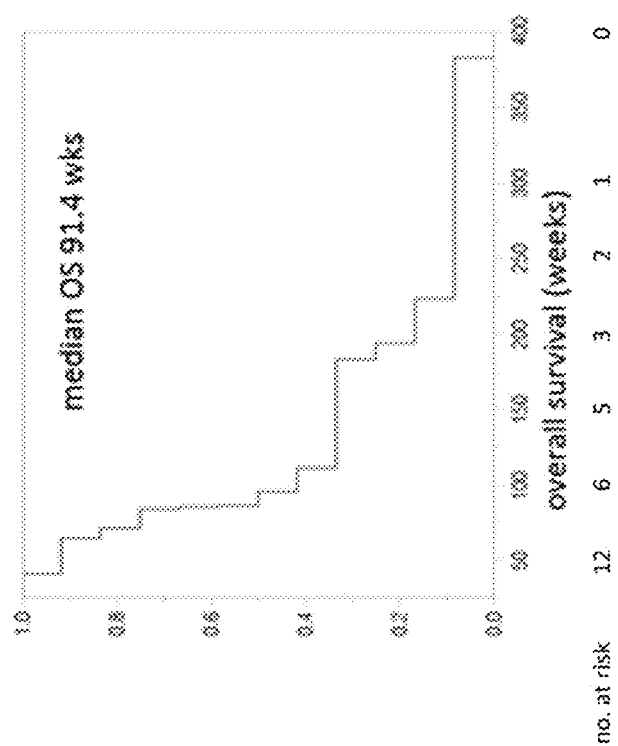
FIGS. 2a-2c depict survival metrics of subjects in Phase I trial (IND 14379-101, NCT01550523).
Figure 2B:
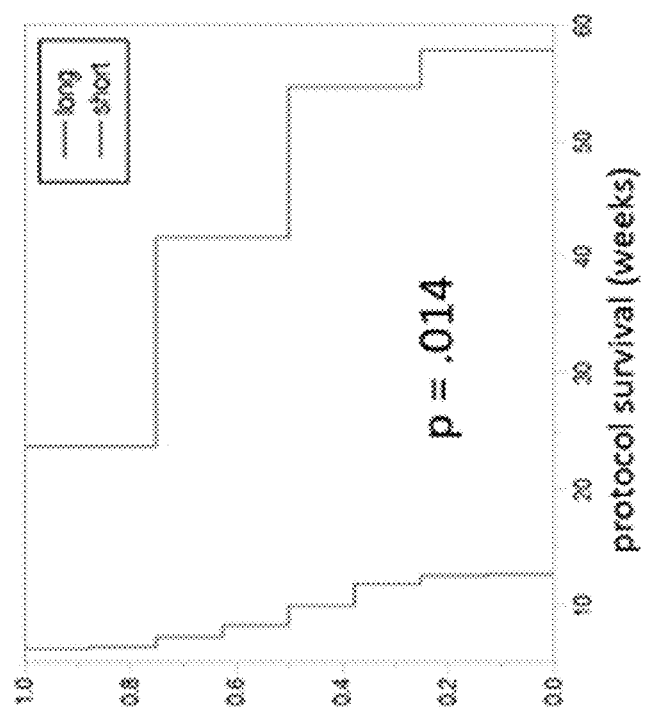
Figure 2C:
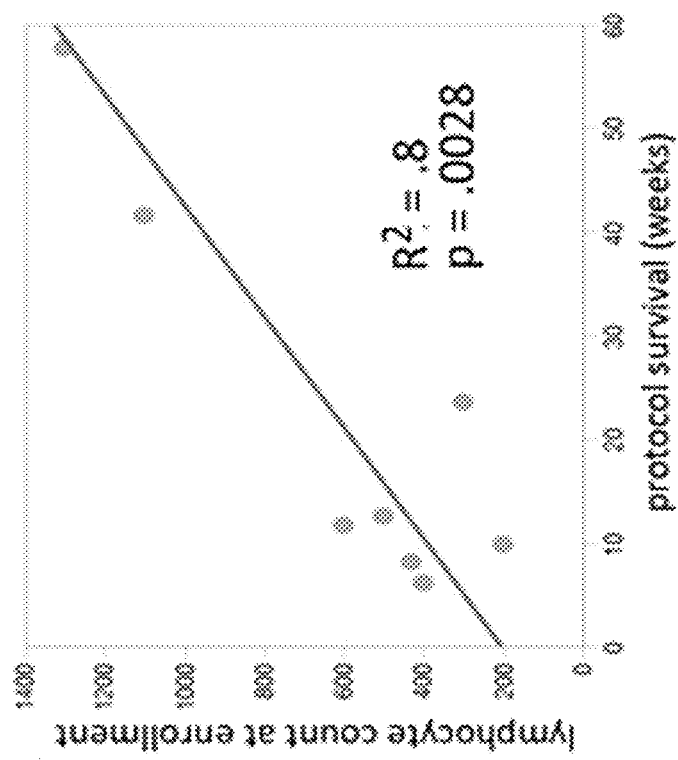

There were no Grade 3 toxicities related to protocol treatment and overall median survival from initial diagnosis was 91.4 weeks (FIG. 2a). Two protocol survival cohorts with median survivals of 48.2 ("long") and 10 weeks ("short") were identified (FIG. 2b). Longer survival subjects had imaging findings including transient elevations in cerebral blood volume (rCBV) and sustained elevations of apparent diffusion coefficient (ADC) values interpreted as transient hyperemia and cell loss. Vaccine therapy resulted in the sustained loss of tumor-promoting CD163+M2 and IGF-1R+ cell populations from the tumor microenvironment (TME). In vitro experiments were performed to explore the origin of CD163+ T cells, and these experiments confirmed that subjects' serum differentiated immature monocytes into CD163+ cells with upregulation of both IGF-1R and PDL-1. Subsequent incubation with IGF-1R AS ODN resulted in a dose-dependent knock down of this M2 population which has implications for the immunogenicity of the encapsulated TME (tumor microenvironment) treated with IGF-1R AS-ODN in the vaccine chamber. The vaccine paradigm was well-tolerated with a favorable median survival.

Example 2

Vaccination of Newly Diagnosed Subjects with Glioblastoma

We demonstrated biological effectiveness of the vaccine protocol involving an autologous cell vaccine delivered as part of a formulated combination product involving implanted biodiffusion chambers in patients with recurrent malignant gliomas who had failed standard treatment, Example 2 describes responses to administering the vaccine to newly diagnosed glioma patients, including implanting 20 chambers for 24 or 48 hours and 10 chambers for 24 or 48 hours. In each case, 2 μg of NOBEL was added into the chamber prior to irradiation in each case. When compared to standard of care in the first interim analysis, there were significant improvements in both progression-free survival and overall survival (FIG. 9). This was most notably due to the performance of the higher dose cohorts after vaccination. We first noted significantly higher peak and mean interferon-gamma levels after vaccination in the newly diagnosed patients compared to patient treated at recurrence. In the trial enrolling newly diagnosed glioma patients, we noted striking and significant increases in IFN-γ with each vaccine dose escalation when measuring aggregate serum measurements. The higher interferon-gamma levels with longer implantation correlated roughly with the rate at which the antisense diffuses out of the biodiffusion chamber.

These data, summarized in FIG. 10, illustrate that the autologous chamber vaccine induces anti-tumor responses in newly diagnosed glioblastoma patients. We further noted that increased IFNγ levels may represent patient responses to tumor antigens and, if so, be a predictor of anti-tumor immunity and improved outcomes. Finally, the more robust response obtained in newly diagnosed GBM patients versus recurrent patients, illustrates the impact of the subject's immune system and supports vaccination of patients as a first-line therapy.

Example 3

Fully Formulated Chambers have Greater Adjuvanticity

The fully formulated chamber includes the autologous tumor cells and other cells included in the tumor microenvironment (TME) treated 6 hours prior to implantation with 4 mg/ml of IGF-1R AS ODN. The treated TME is then encapsulated with exogenous addition of at least 2 μg of IGF-1R AS ODN and the chamber is then irradiated with 5 Gy of gamma-irradiation.

We increased the number of chambers, meaning that the dose of IGF-1R AS ODN received by each patient increased compared to previous studies. For example, twice the number of chambers implanted resulted in twice the amount of the antisense implanted and capable of diffusing out of the chamber, meaning the dose of AS ODN was about 40 μg, split between 20 chambers.

The antisense sequence, particularly its palindromic CpG motif, and the direct mixture with glioma cells in situ effectively initiate anti-tumor immunity. Notably, the sense sequence with the same palindromic CpG motif, is ineffective in the vaccine paradigm. Additionally, the antisense sequence must be directly admixed with the tumor inoculum in order to see a satisfactory response. The dose of the IGF-1R AS ODN that will inhibit M2 monocyte polarization is at least an order of magnitude lower than the dose necessary to down-regulate expression of IGF-1R.

In preclinical animal modeling we assessed the efficacy of various antigen preparations in restimulating therapeutic IFN-γ-producing CD4 T cells from C57 B6 mice that had rejected syngeneic GL261 glioma cells implanted in their cerebral cortex after vaccination. CD4 T cells were isolated from the spleens of these animals using conventional approaches and added to bone marrow-derived dendritic cells from antigen naïve mice that had been incubated with various GL261 antigen preparations. Antigens recovered from the soluble fraction of a fully formulated vaccine chamber including autologous tumor cells, exogenous antisense, and irradiation elicited significantly greater numbers of IFN-γ-producing CD4 T cells than incomplete formulations.

Analysis of chambers containing different GL261 preparations implanted into the flanks of C57BL/6 mice for 24 hours also provides evidence that the fully formulated chamber is most immunogenic. While IGF-1R AS ODN and irradiation each alone cause elevations of cytokines above a PBS control, 16 of 32 cytokines were significantly elevated over all other variables, including irradiation alone, when combined with IGF-1R AS ODN. Among these, at least 11 cytokines are associated with an inflammatory response, including IL-1β, IL-6 and TNF-α which are commonly produced by a radiation-induced pro-inflammatory cytokine network.

A proinflammatory response to the fully formulated chambers was validated in our second Phase 1 human trial for patients with recurrent glioblastoma. We noted two distinctly different survival cohorts after vaccination and established associations between immune fitness, a proinflammatory response after vaccination, and longer survival (unpublished observations). In particular we noted an elevated CD4:CD8 ratio after vaccination in the longer cohort that we interpreted as local TLR9 DC activation directing CD4+ cells toward a Th1 phenotype perhaps augmented further by the irradiation of tumor cells in the chamber.

Example 4

Fully Formulated Chamber in Naïve Mice

In naïve C57B6 mice, implantation of a fully formulated vaccine chamber was significantly more effective at eliciting an initial immune response than partially formulated chambers. Mice were vaccinated in the flank with one chamber for 24 hours. Chamber contents varied from no contents (PBS), partially formulated chambers (GL261 glioma cells alone, GL261 with AS ODN, or GL261 and 5Gy of irradiation), and fully formulated chambers (GL261, AS ODN, and irradiation).

As shown in FIG. 11, there was a greater production of pro-inflammatory cytokines in mice implanted with a fully formulated vaccine chamber compared to mice implanted with partially formulated vaccine chambers (i.e. vaccine chambers containing tumor cells but no antisense molecules).

Example 5

Dose-Dependent Dendritic Cell Activation in Normal Samples by IGF-1R AS ODN

PBMC from two normal donor sources were used to assess dose-dependent DC activation by NOBEL anti sense as well as the sequence used previously (DWA, 18-mer two codons upstream from the NOBEL sequence and described in Andrews et al. (2001) "Results of a pilot study involving the use of an antisense oligodeoxynucleotide directed against the insulin-like growth factor type I receptor in malignant astrocytomas." J Clin Oncol 19:2189-2200).

PBMC were incubated overnight with the antisense sequences, along with the sense sequence to the NOBEL antisense, then analyzed by flow cytometry, gating for a CD123+, CD68+ activated DC population. As shown in FIG. 12, the NOBEL antisense yielded a dose-dependent DC activation that was significantly different from unstimulated controls or NOBEL sense sequence, and more effective than the DWA sequence. These data illustrate that, even compared to other IGF-1 AS, the NOBEL sequence is especially effective.

Example 6

In Vitro T Cell Response from Contents of Fully Formulated Chamber Utilizing T Cells Derived from Vaccinated Mice We hypothesized that, given the small pore size of the diffusion chamber (100 nm) that exosomes were the likely source of tumor antigen diffusing through the chamber membrane during implantation. C57B6 mice vaccinated with a flank injection that included GL261 glioma cells and IGF-1R AS ODN were fully protected against a subsequent brain intra-parenchymal tumor challenge. We assessed vaccinated, tumor therapeutic T cell immunoreactivity derived from these mice to contents of the fully formulated chamber with Elispot assays for IFNγ using the following antigen sources: 1/Centrifuged supernatants from chambers loaded with GL261 cells and IGF-1R AS ODN irradiated and implanted in the mouse flank for 24 hours; 2/Centrifuged supernatants from similarly prepared chambers incubated in isotonic PBS medium overnight at 37° C.; 3/Exosomes prepared from GL261 cells. These antigen preparations were added to dendritic cells from tumor antigen naïve mice and then added to CD4 T cells isolated from the spleens of GL261 immune mice or incubated overnight prior to addition to the T cells to allow antigen processing and presentation. Following 24 hour coculture of the T cells antigen and dendritic cells the number of IFNγ-producing CD4 T cells was quantified in an Elispot assay. Chamber contents were compared to GL261 exosomes at various dilutions. Elispot results revealed a robust IFN-γ response only with chamber contents retrieved from 24 hour PBS incubation assayed with antigen presentation. Neither implanted chambers nor control Elispot assays in which dendritic cells were included without preincubation yielded significant differences from exosomes. These data reveal that antigens derived from the TME are not exosomal in nature, are most abundantly produced in irradiated chambers containing the tumor cells and IGF-1R AS ODN, that they are expended during implantation, and that they require antigen presentation by DCs. Results are summarized in FIG. 13.

Example 7

Biphasic Dose Response to M2 Monocyte/Macrophage Polarization

To determine the optimal dose of NOBEL IGF-1R AS-ODN to inhibit M2 polarization in vivo, C57BL/6 mice were injected in the flank with $10^6$ GL261 cells. 20 days later, the mice were given a single 0.75 or 0.075 mg dose of NOBEL IGF-1R AS-ODN intraperitoneally. The mice were then followed for tumor development.

Figure 17:
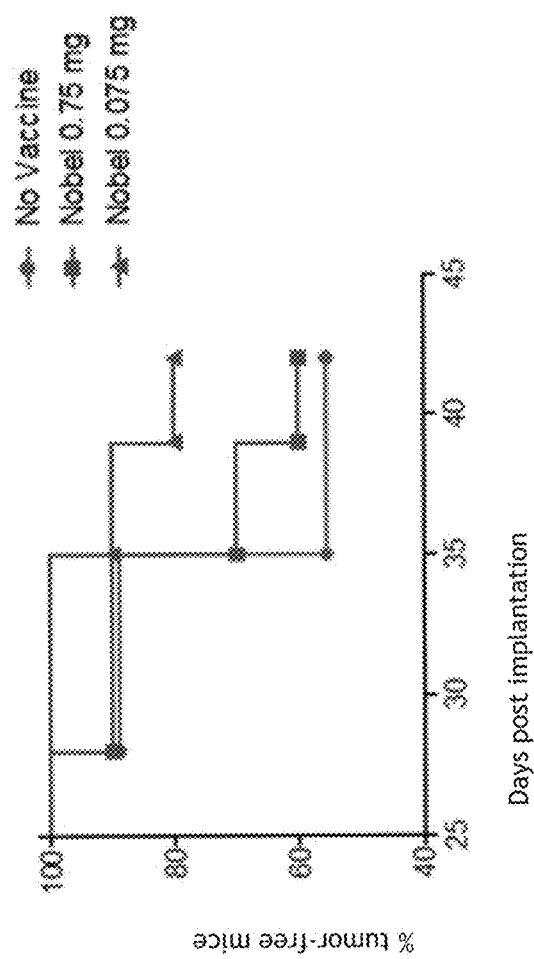
FIG. 17 is a dose-response curve, showing the biphasic response of systemic IGF-1R AS-ODN on inhibition of flank glioma tumor growth. $10^6$ GL261 cells were implanted into the flanks of C57BL/6 mice and 20 days later, prior to the period when an elevation in circulating CD163 positive cells is typically observed, the mice were injected intraperitoneally with a single 0.75 mg (squares) or 0.075 mg (triangles) dose of NOBEL IGF-1R AS-ODN. The mice were then followed for tumor development. Unvaccinated mice (circles) were used as a control.

The dose titrations of the NOBEL antisense on M2 generation in vivo yielded a paradoxical biphasic response. While doses at either extreme of a dose-seeking titration resulted in M2 monocyte knockdown, intermediate doses actually stimulated M2 monocyte generation. In US 2017/0056430, it was shown that a single dose of 4 mg is highly effective in similar experiments. In the instant experiment, a single dose of 0.075 mg was highly effective, whereas an intermediate dose of 0.75 mg was unexpectedly less effective. (FIG. 17). Without being limited, held or bound to any particular theory or mechanism of action, we hypothesize that the biphasic effect may be a consequence of the immunostimulatory attributes of the NOBEL sequence.

The effective dose for inhibition of monocyte polarization by AS ODN is considerably lower than the dose necessary to downregulate IGF-1R translation according to Watson-Crick base-pairing rules. Notably, in vitro doses equivalent to the 0.075 mg dose per mouse have no effect on cells that are already expressing IGF-1R. In vitro titration experiments with human monocytes reveal a substantial difference in the capacity of IGF-1R AS-ODN treatment to prevent polarization as opposed to impact the phenotype or function of polarized M2 monocytes.

As shown in FIG. 14, the lowest dose achieves the same efficacy as the highest dose suggesting a complex dynamic between the NOBEL antisense and M2 generation. Based on the monophasic response to DC activation, the ideal chamber dose would be the point of maximal DC activation.

Example 8

Dose Response Curve for Inhibition of Monocyte Polarization by NOBEL

We performed a NOBEL antisense titration to levels in the aggregate range of concentrations that feasibly would diffuse locally out of the implanted chambers.

As shown in the FIG. 15, allogeneic naïve monocytes from three normal PBMC collections were incubated overnight with six different sera obtained from patients with glioblastoma, in the presence or absence of different concentrations of IGF-1R specific AS-ODN (NOBEL). Each colored dot represents serum from an individual glioblastoma patient. Expression of markers including CD163 was assessed by flow cytometry. CD163 expression levels are presented as the mean fluorescence index of cells stained with fluorescent conjugated CD163 antibodies.

Each patient's sera caused differentiation of M0 monocytes into M2 CD163 phenotype with upregulation of both IGF-1R and PDL-1. M0 cells cultured without patient sera (ctrl) maintained very low levels of CD163 while overnight incubation in sera strongly induced expression of this M2 marker (untreated). The addition of IGF-1R specific AS-ODN to the culture media inhibited M0-M2 polarization as indicated by the elevated expression of CD163 in a dose-dependent manner. We noted a downward trend starting at 100 pg and reaching a significant level of inhibition at 1 μg. These data confirm that excess antisense diffusing out of the chamber can facilitate the initiation of a Th1 response in the initial stages of innate immunity.

Example 9

Prevention of the Appearance of Anti-Inflammatory M2 Monocytes in Mice Implanted with CL261 Glioma Cells C57BL/6 mice implanted with GL261 glioma cells develop tumors in parallel with elevated numbers of circulating CD163 expressing M2 monocytes. We hypothesized that the glioma cells produce factors that cause monocyte recruitment and polarization to M2. These cells then infiltrate tumor tissues where their products promote tumor progression. Systemic treatment with IGF-1R AS-ODN may prevent the appearance of M2 cells and thereby inhibit tumor formation.

Figure 18:
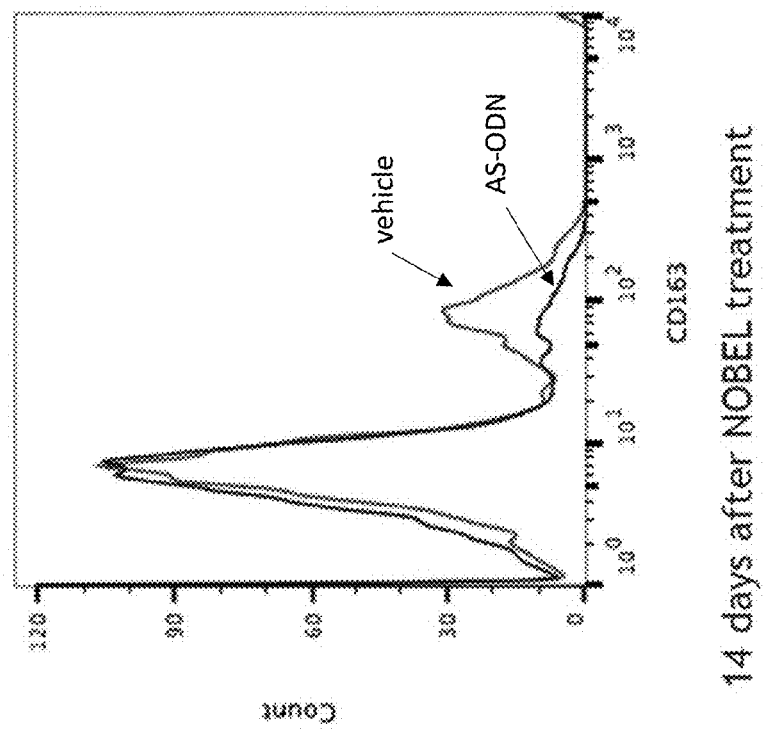
FIG. 18 is flow cytometry data showing that systemic IGF-1R AS-ODN treatment inhibited the accumulation of circulating M2 monocytes. The data is expressed as a histogram of cell numbers expressing CD163 (right hand peak) where the red line represents tumor-implanted mice treated with PBS (vehicle) and the blue line represents implanted mice treated with NOBEL IGF-1R AS-ODN.

C57BL/6 mice were implanted in the flank with $10^6$ GL261 cells and given a single dose of 4 mg NOBEL IGF-1R AS-ODN intraperitoneally or intravenously 20 days later. 14 days later peripheral blood was obtained from the animals and circulating monocytes assessed by flow cytometry for the expression of CD163. FIG. 18 shows a histogram of cell numbers expressing CD163 (right hand peak) where the red line represents implanted mice treated with PBS vehicle and the blue line implanted mice treated with the AS-ODN. The data shows that CD163+ cells significantly decline. The appearance of cells expressing CD204 or CD206 was similarly inhibited (data not shown). Peripheral blood from normal, non-implanted mice did not contain cells with high levels of CD163, CD204, or CD206 (data not shown).

Example 10

Systemic IGF-1R AS-ODN Treatment of Mice Implanted in the Flank with Glioma Cells Prevents the Development of Tumors.

Figure 19:
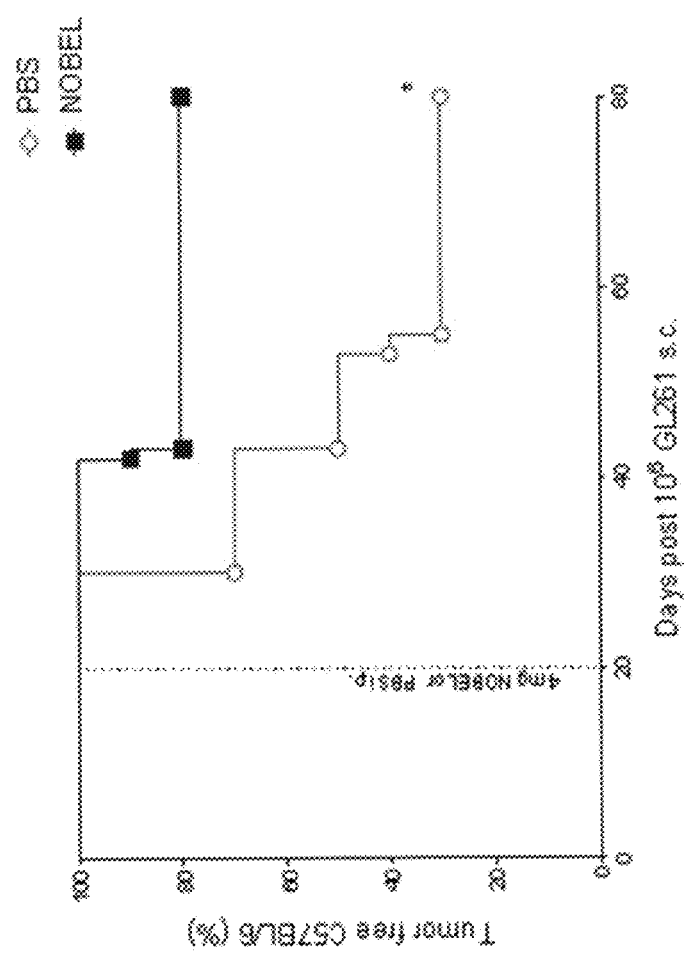
FIG. 19 shows tumor incidence in mice implanted in the flank with glioma cells, treated with NOBEL IGF-1R AS-ODN or PBS (vehicle). Tumor incidence between the treated and untreated groups was significantly different (*=p<0.05).

C57BL/6 mice were implanted in the flank with $10^6$ GL261 cells and given a single 4 mg dose of NOBEL IGF-1R AS-ODN intraperitoneally or intravenously 20 days later, prior to the appearance of circulating CD163-positive monocytes. Another group of C57BL/6 mice were injected with PBS as a control. Both groups of mice were then followed for tumor development. As shown in FIG. 19, tumor incidence between the treated and untreated groups was significantly different (*=p<0.05) with the NOBEL-treated mice much more like to remain tumor-free.

Example 11

Systemic IGF-1R AS-ODN Inhibition of Flank Glioma Tumor Growth is Independent of Anti-Tumor Immunity.

Tbet is a T-cell associated transcription factor, and Tbet deficient mice lack the ability to mount anti-glioma immunity. To test whether IGF-1R AS-ODN inhibition of flank glioma tumor growth is independent of anti-tumor immunity, Tbet deficient mice on a C57BL/6 background were implanted in the flank with $10^6$ GL261 cells and given a single 4 mg dose of NOBEL IGF-1R AS-ODN intraperitoneally or intravenously 20 days later. The mice were then followed for tumor development.

Figure 20:
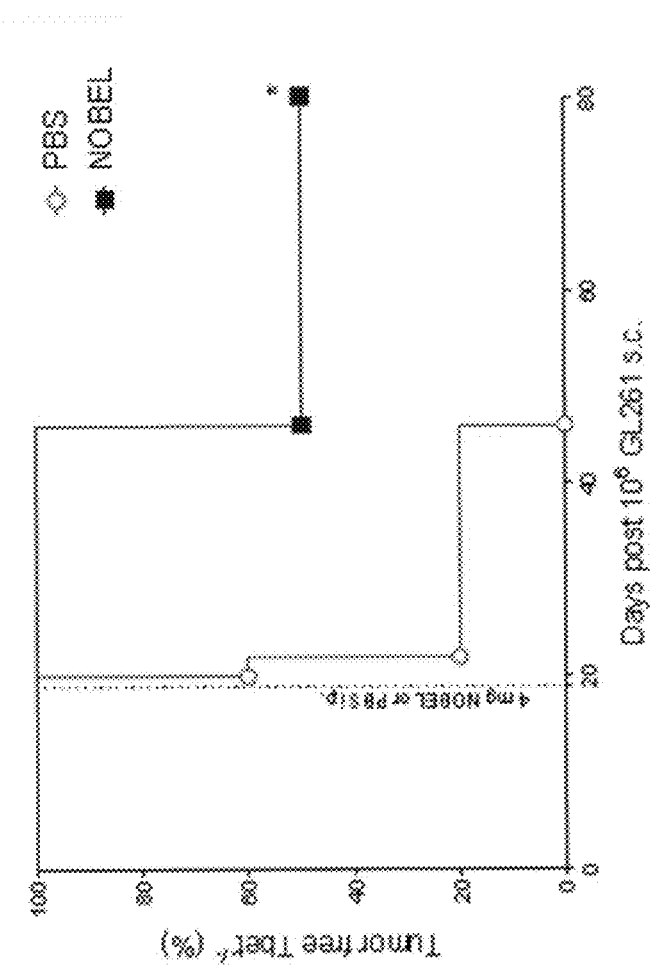
FIG. 20 shows tumor incidence in Tbet deficient mice implanted in the flank with glioma cells, and treated with or without NOBEL IGF-1R AS-ODN. Tumor incidence between the groups was significantly different (*=p<0.05).

As shown in FIG. 20, tumor incidence between mice treated with PBS and mice treated with NOBEL IGF-1R AS-ODN was significantly different (*=p<0.05) despite the inability of Tbet deficient mice to mount therapeutic anti-glioma immunity.

Example 12

Targeting Nestin+ Stem Cells in the Chamber with NOBEL

We have shown that Nestin+ stem cells can be knocked down in a dose-dependent manner by the NOBEL antisense in vitro and further that these cells are eliminated from the TME after the autologous cell vaccine (trial 14379-101, unpublished observations). As stem cells that are part of the glioma tumor microenvironment (TME), selectively knocking them out has clear therapeutic benefit. With a morphology that supports an embryonic radial glial cell, these cells by their design and long processes could serve as scaffolding allowing for deployment of glioma cells throughout the brain. Removing them along with CD163 TAMs could reverse the invasive nature of these tumors as well as tumor growth itself. As a targetable cell in the chamber, antigens from these cells could be very immunogenic and tumor-specific since they would be embryonic in origin. Nestin is primarily expressed in neural progenitor/stem cells and is located in the cytoplasm as a type VI intermediate filament. It has also been identified as a surface protein and a biomarker for glioma stem cells. It would therefore be possible to bead-select and enrich this population thereby increasing the proinflammatory titer of the chamber. See Jin et al., "Cell surface Nestin is a biomarker for glioma stem cells," Biochem Biophys Res Commun. 2013 Apr. 19; 433(4):496-501

Example 13

The Impact of Irradiation on the Chamber Formulation

Figure 1F:
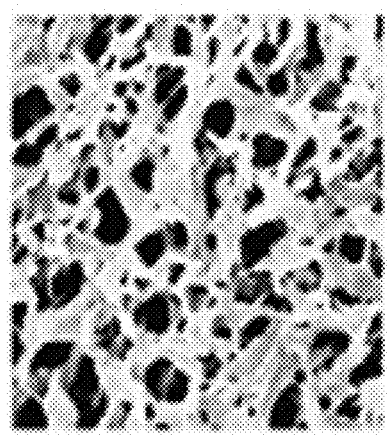
Figure 1G:
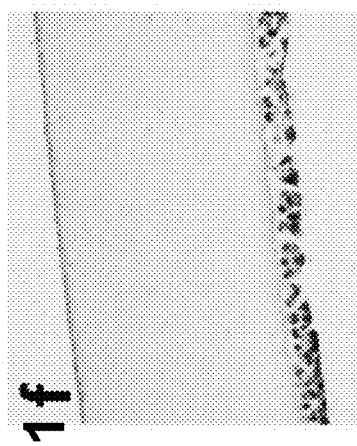

During preparation of the fully formulated chamber, autologous tumor cells (i.e. freshly resected tumor tissue) are plated in serum-free culture, optionally treated with a first amount of an IGF-1R AS ODN, and later treated with ex vivo irradiation (FIGS. 1f and 1g). A second amount of IGF-1R AS ODN is added to the chamber before irradiation.

Since the autologous vaccination includes irradiation of the combination product prior to implantation at a site remote from the tumor and our data support an immune response with tumor regression, these data support a novel abscopal effect. Typically, abscopal effects are attributed to activation of anti-tumor immunity after in situ radiation of a targeted tumor, which leads to tumor regression at sites distant from the radiation. In this particular formulation, the addition of exogenous antisense with a CpG motif to the chamber, and subsequent treatment with gamma-irradiation has been shown to up-regulate genes engaged in the activation, proliferation, and survival of memory T-cells. Such a formulation also prevents the activation of genes involved in the generation of Tregs and the induction of immune tolerance. Additionally, down-regulation of the IGF-1R radiosensitizes cells which are overexpressing this surface receptor. Coincubation with IGF-1R AS ODN also promotes apoptosis of targeted tumor cells (only in vivo) and tumor-associated M2 macrophages. Irradiation with 5 Gy leads to death of all encapsulated cells and causes the release of endogenous danger signals known as danger/damage-associated molecular patterns (or DAMPS) that augment the presentation of tumor antigens released from dying tumor cells.

Example 14

Figure 16:
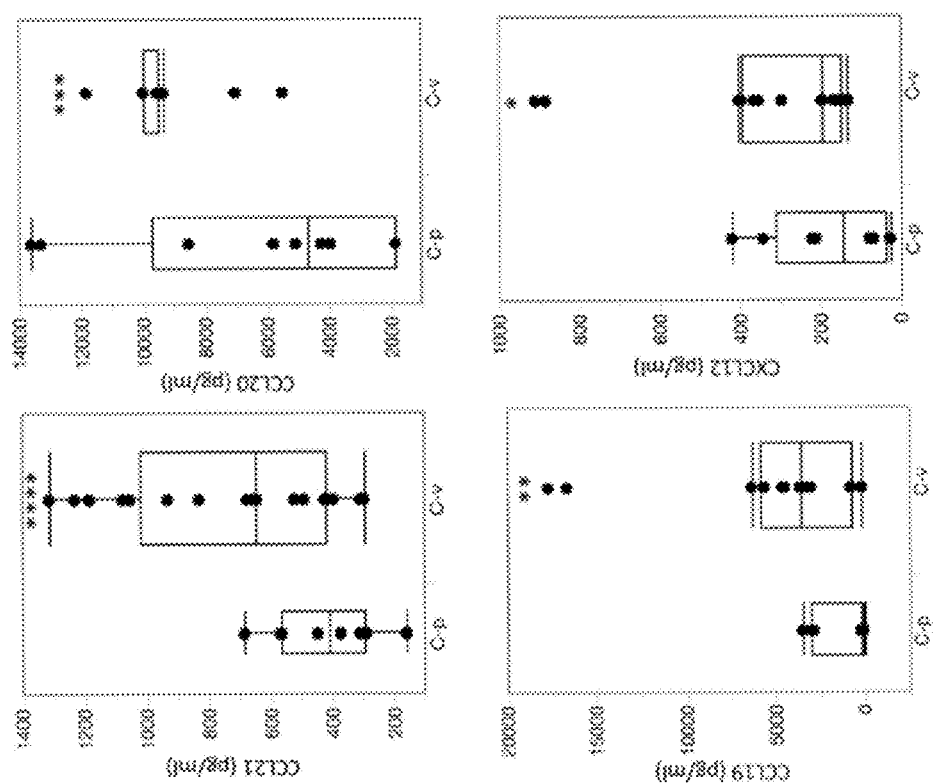
FIG. 16 depicts comparison of explanted vaccine chamber cytokine levels v. explanted PBS control chamber. *p, 0.005; *p<0.01; *p<0.02; p<0.03; *p<0.05.

The Explanted Chamber as a Means of Identifying Pro-Inflammatory Agents for Future Chamber Formulations The explanted biodiffusion chamber, retrieved after its application as a depot antigen device, also serves as repository documenting the initial immune response corroborated in a preclinical mouse model and in a human trial. Characterization of the chamber contents, with an appropriate PBS (dummy) chamber control, provides insight into both the host immune response (in-diffusion of cytokines/chemokines above the dummy control) as well as production of cytokines/chemokines/DAMPS by cells within the chamber (undetectable in the dummy chamber). Consistent presence of an array of cytokines informs exogenous additions of these cytokines to future formulations. As examples, CCL21 and CXCL, are both elevated in the vaccine chambers over PBS chambers, synergize with CpG adjuvants and enhance the migratory and T cell stimulatory capacity of DCs in a vaccination paradigm. See FIGS. 16 and 17. The exogenous addition of these cytokines to the chamber formulation could enhance the initial Th-1 response.

Example 15

Optimum Ratio of Cells to IGF-1R AS ODN in Chamber Leads to Higher Cytokine Values Patients were vaccinated with 20 chambers each containing irradiated tumor cells and AS NOBEL ODN (2 μg) for 48 hours. In each case, patients also received mandatory Thomas Jefferson University Hospital (TJUH) Standard of Care (SOC) therapy. Patients were followed to determine progression-free survival (P-FS) (i.e., those patients both alive and showing no development of cancer or remission) and overall survival (OS) at certain time-points. FIGS. 21a-c illustrate responses at certain time-points. FIGS. 24-27 illustrate patient outcomes and compares those patients treated ("vaccinated") vs. the historic standard of care ("SOC"). To determine the optimum ratio of cells to IGF-1R AS ODN in the chambers, we measured pro-inflammatory cytokine levels in patient serum after vaccination and compared these cytokine levels to cell number of tumor tissue removed from each patient.

Initially, as shown in FIGS. 21a-c, a significant dose-dependent increase in pro-inflammatory cytokines was observed in patient serum. Overall levels of IFN-γ were elevated quite significantly for the highest dose cohort. The levels of IL12 and TNFa were also elevated in this cohort.

Each of the three cytokine values from days 14-42 for each patient were pooled and plotted against IFNγ, IL12 and TNFa mean values. Two polynomial plots with similar degree fits of 4 and 5 revealed peak pro-inflammatory cytokine values (FIGS. 21d-f).

FIGS. 24a and 24b show Kaplan-Meier curves illustrating progression-free survival and overall survival in the intention to treat group as a whole. In vaccinated patients, over about 35% were alive and were progression-free at 20 months. In contrast, less than 10% of SoC-treated patients showed progression-free survival at 20 months. Overall survival was similarly much improved with about 40% of patients surviving beyond 25 months, whereas SOC-treatment shows around 5% survival at that time-point. FIG. 24b.

FIGS. 25a and 25b shows survival data for patients with a median age of 61.5 years and matched such that the female/male numbers are 12/18 in both groups. Again, the data illustrate the significantly improved survival at various timepoints.

During the trial, some patients withdrew from protocol and others died from unrelated causes. FIGS. 26a and 26b illustrate survival data absent data from patients from those withdrawn patients or where deaths were from other causes. Again, the vaccinated patients perform significantly better. Certain patients were unable to complete the standard of care. Data excluding those patients is shown in FIGS. 27a and 27b. These data confirm that the vaccination approach is effective when standard of care protocol is not followed.

FIGS. 28a and 28b illustrate the dosing effect of the cell number on patient response. IFN-γ levels correspond to subject response. Higher IFN-γ levels are associated with better patient immune response and hence anti-tumor response. Here, we optimized that response by determining the correct titration of cells. The peak response is around the 20 mark, i.e., 20 million cells, divided among 20 chambers. Thus, peak response is around 1 million cells/chamber while an excellent response is obtained with around 15 to 25 million cells, each divided and implanted in 20 chambers; i.e. a range of 750,000 cells to 1,250,000 cells per chamber. These data demonstrate the efficacy of the optimized vaccination protocol.

Example 16

Figure 30A:
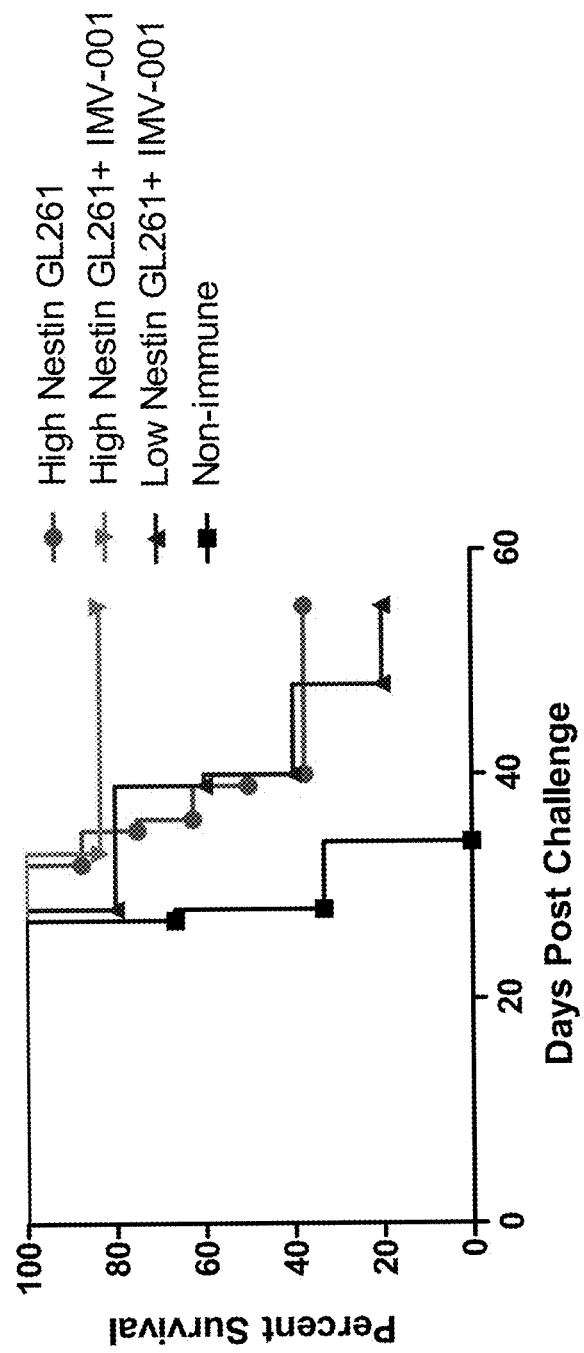
FIGS. 30a, 30b, 30c, and 30d illustrate the impact levels of expression of Nestin on efficacy in a mouse model.
Figure 30B:
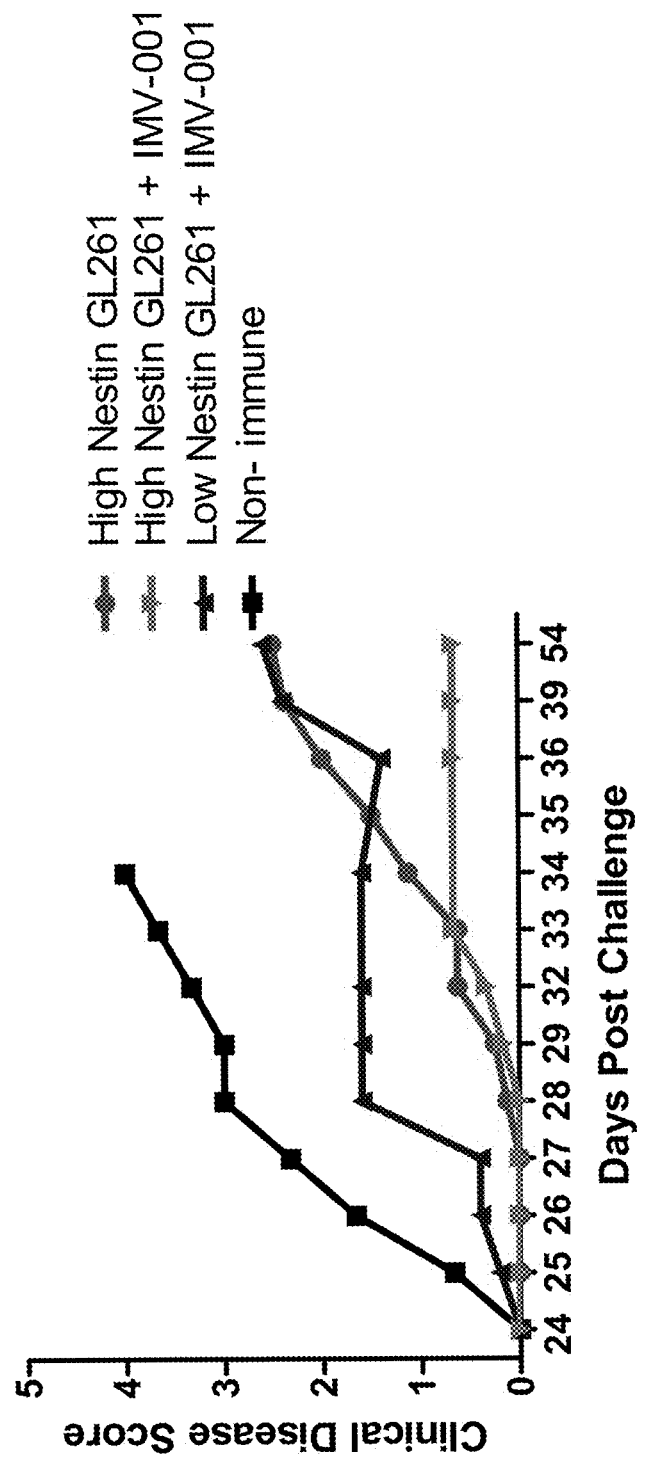
Figure 30D:
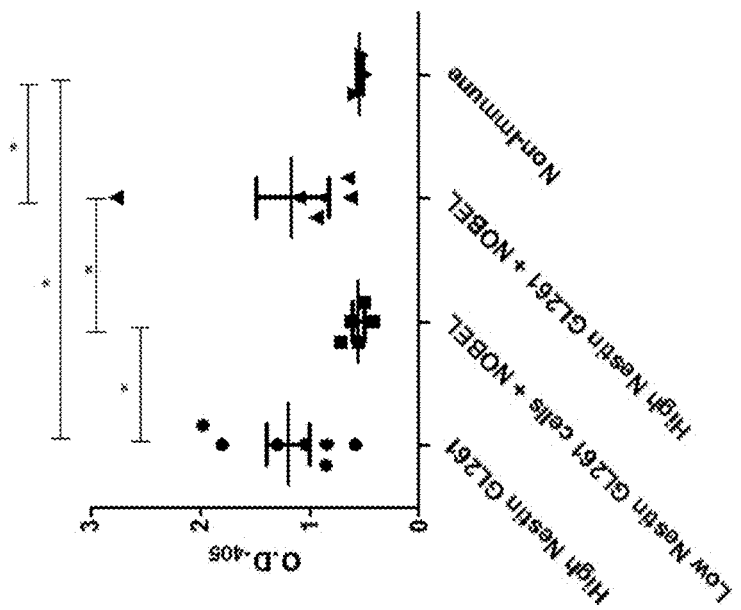
Figure 30C:
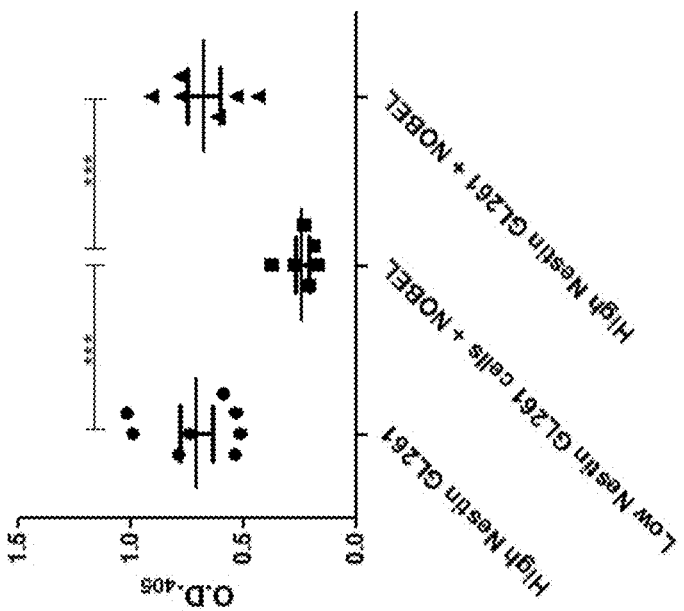

Enhanced Anti-Tumor Response Mediated by Vaccination with Cell Population Enriched for Nestin Expression The production of antigens by IGF-1R-treated glioma cells in chambers was tested ex-vivo using glioma-immune T cells isolated from C57BL/6 mice immunized using the chamber paradigm and challenged intra-cranially with congenic GL261 cells to detect the presence of antigen. Mice to serve as donors of immune T cells were immunized as follows: Fully formulated chambers filled with GL261 cells and antisense were implanted for 24 hours in the flank. Chambers with only cells and no antisense were also implanted as controls for antisense activity. Mice were bled throughout the experiment and sera was tested for antibody reactivity to GL261 cells (FIG. 30c, 30d). At 35 days post-chamber implantation, the mice were challenged intra-cranially with GL261 cells stereotactically. Survival and clinical signs of disease for the separate groups of mice were monitored for at least 40 days post-challenge. Survival and clinical disease score are shown in FIGS. 30a and 30b, respectively.

Figure 29A:
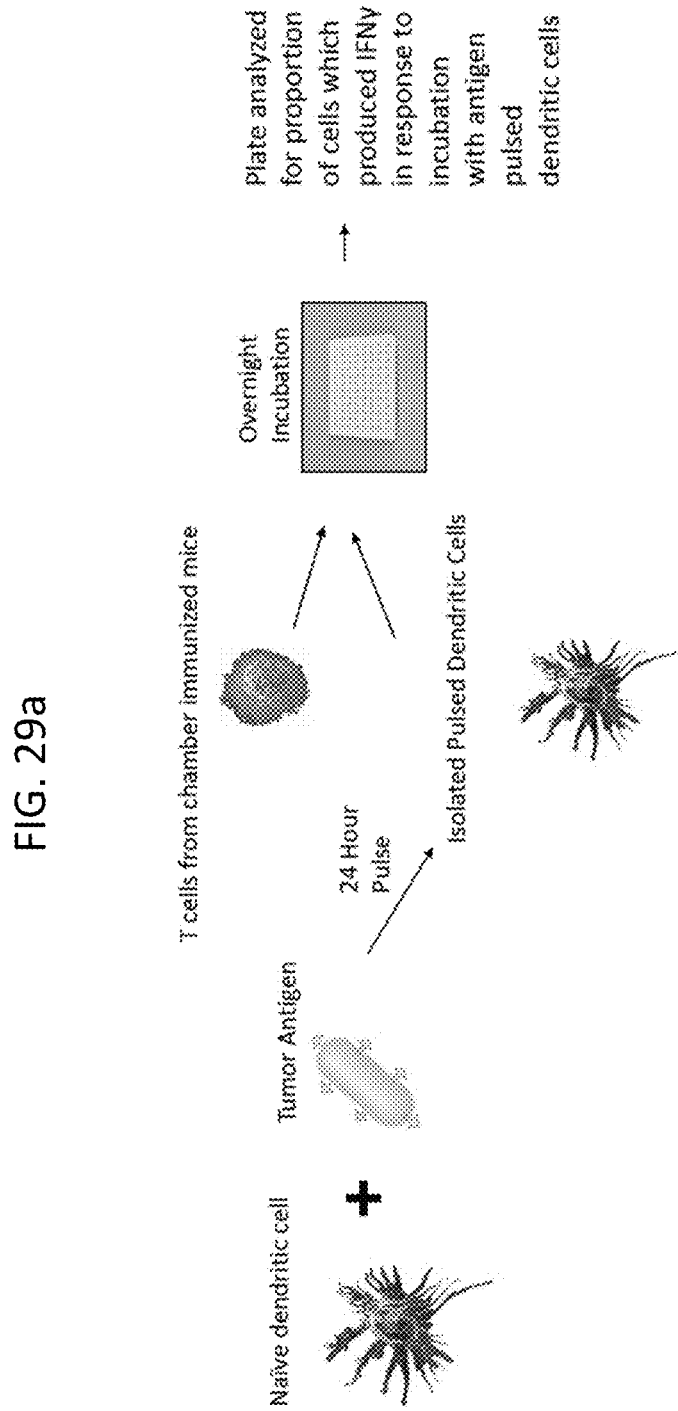
FIGS. 29a, 29b, and 29c illustrate IFN-γ T cell response relative to chamber formulation regarding IGF-1R antisense pre-incubation prior to encapsulation.

CD4+ T cells were isolated from the spleens of immunized mice using magnetic beads. Naïve dendritic cells (DC), which were used to present the antigens to immune CD4 T cells, were isolated from the bone marrow of autologous, non-immune C57BL/6 mice. The DC were pulsed by overnight culture with GL261 antigens recovered from GL261 cells cultured in chambers overnight under different conditions, thereby mirroring what is happening with respect to antigen production when similar chambers are implanted in a subject. The chambers contained either GL261 cells alone or GL261 with 3 different doses of antisense in phosphate buffered saline (PBS). Antisense at the different doses was added to antigen preparations from G261 cells cultured without antisense to determine whether the antisense content or the effect of antisense in the chambers is responsible for optimal antigen production. IFNγ production, believed to be the key measure of anti-tumor cell immunity, was used to assess the stimulatory effects of the various antigen preparations on T cell activation, with the specific number of responding cells quantified by the ELISPOT assay, as depicted in FIG. 29a.

To stimulate production of the antigen, we followed the in-vivo clinical chamber paradigm. Approximately 1 million ex-vivo GL261 tumor cells were injected into chambers alone or with indicated antisense concentrations and incubated overnight in the chamber which was placed in PBS). The following day, chamber content was extracted and used to pulse naïve dendritic cells. Chamber content which was not treated overnight with antisense was added to the dendritic cells with the indicated amounts of NOBEL. Dendritic cells were also left naïve for control. Following an overnight pulse with antigen, dendritic cells were collected and incubated overnight with T cells from immunized animals in a cell culture plate coated with an ELIPSPOT detection antibody for the cytokine IFNγ. After overnight incubation, the coated plate was processed and developed to enumerate the number of IFNγ-producing T-cells which responded to each respective antigen.

Figure 29C:
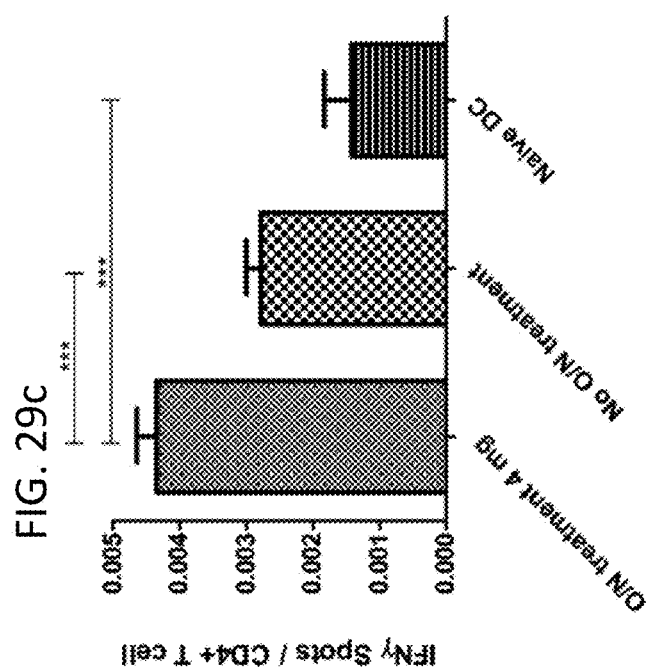
Figure 29B:
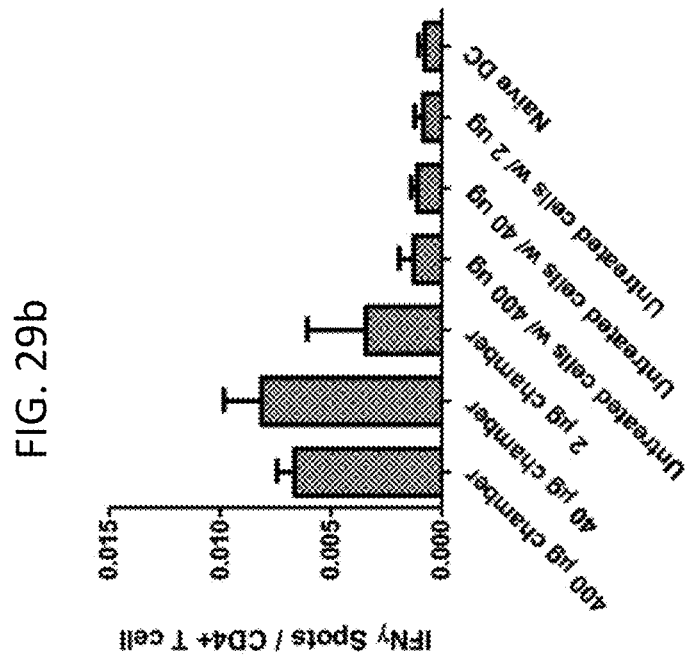

As shown in FIG. 29b, tumor antigens were detected in materials recovered from chambers containing GL261 cells plus antisense but not materials from chambers cultured with cells alone, even if antisense was added to the material when the DC were pulsed. This shows that the presence of antisense in chambers with the glioma cells is required to produce immunostimulatory tumor antigen.

To test the impact of overnight treatment with antisense, we also incubated cells overnight with 4 mg of antisense prior to addition of the cells to chambers. GL261 cells were plated in petri dishes and treated overnight with 4 mg NOBEL per 1 million cells or were left untreated. The cells were then collected and placed into chambers at 1 million cells and 2 g NOBEL per chamber. The chambers were then incubated overnight in PBS and the content was extracted the following day. Dendritic cells were then pulsed with the chamber content and IFNγ secretion was measured as described above.

As shown in FIG. 29c overnight treatment of GL261 cells with antisense enhances the amount of antigen produced by these cells as detected by an increase in the numbers of tumor-immune T cells producing IFNγ when DC were pulsed with GL261 cells treated with 4 mg antisense overnight.

To determine if the glioma tumor cell subset that expresses nestin is associated with enhanced immunogenicity, mice were immunized with chambers with or without IMV-001 (NOBEL) antisense containing GL261 cells grown under conditions that resulted in higher versus lower levels of the protein nestin. Long-term protection against the subsequent intracranial implantation of GL261 glioma cells (FIG. 30a, 30b) as well as the production of GL261 antibody (FIG. 30c, 30d) by the mice were assessed.

Chambers containing GL261 cells with high levels of nestin and antisense induced considerably better immune protection than chambers with similar cells without antisense or chambers with low-nestin GL261, regardless of whether or not antisense was included. Chambered GL261 cells expressing high levels of nestin were also superior at inducing GL261-specific antibody production in the mice than those containing low nestin levels. However, with respect to antibody production, the inclusion of antisense had minimal impact.

INCORPORATION BY REFERENCE

All patents and publications referenced herein are hereby incorporated by reference in their entireties.

What is claimed is:

1. A method of vaccinating a subject having a brain cancer comprising:
   (i) obtaining viable morselized tumor tissue from the subject;
   (ii) collecting the morselized tissue in a sterile trap;
   (iii) harvesting adherent cells from the morselized tissue;
   (iv) encapsulating the harvested cells in a biodiffusion chamber along with insulin-like growth factor receptor-1 antisense oligodeoxynucleotide (IGF-1R AS ODN) having the sequence of SEQ ID NO:1; wherein the chamber contains about 1×10⁴ to about 5×10⁶ tumor cells and about 1 μg to about 5 μg of the IGF-1R AS ODN;
   (v) irradiating the chamber, and
   (vi) implanting the chamber in the subject,
   wherein an immune response against the brain cancer is obtained.

2. The method of claim 1 comprising the step of treating the adherent cells with IGF-1R AS ODN for up to 18 hours prior to encapsulation.

3. The method of claim 1, wherein the subject is vaccinated with 20 chambers for about 48 hours.

4. The method of claim 1, wherein the chamber comprises from about $1\times10^5$ to about $1.5\times10^6$ tumor cells.

5. The method of claim 1, wherein the chamber contains about 4 µg of the IGF-1R AS ODN.

6. The method of claim 1, wherein the tumor cells are not exposed to temperatures above body temperature.

7. The method of claim 1, wherein the chamber contains about $10^6$ tumor cells.

8. The method of claim 1, wherein the brain cancer is selected from a grade II astrocytoma, a grade AIII astrocytoma, a grade AIII-G astrocytoma, and a grade IV astrocytoma (glioblastoma multiforme).

9. A biodiffusion chamber for implantation into a subject having brain cancer, the biodiffusion chamber comprising:
   (a) irradiated tumor cells,
      wherein the tumor cells comprise adherent cells obtained from the subject's tumor tissue using a tissue morselator;
      wherein the tumor cells are pre-incubated with insulin-like growth factor receptor-1 antisense oligodeoxynucleotide (IGF-1R AS ODN) prior to encapsulation within the chamber; and
   (b) irradiated IGF-1R AS ODN wherein the IGF-1R AS ODN has the sequence of SEQ ID NO: 1;
wherein the chamber contains about $1\times10^4$ to about $5\times10^6$ tumor cells and about 1 µg to about 5 µg of the IGF-1R AS ODN.

10. The biodiffusion chamber of claim 9, wherein the chamber contains about 4 µg of the IGF-1R AS ODN.

11. The biodiffusion chamber of claim 9, wherein the tumor cells in the chamber are enriched for Nestin-positive cells compared to the tumor tissue obtained from the subject.

12. The biodiffusion chamber of claim 9, wherein the chamber contains about $10^6$ tumor cells.

13. The biodiffusion chamber of claim 9, wherein the tissue morselator comprises a high speed reciprocating inner cannula within a stationary outer cannula.

14. The biodiffusion chamber of claim 9, wherein the tissue morselator does not produce heat directed to the tumor tissue when the tissue is obtained from the subject.

15. The biodiffusion chamber of claim 9, wherein the chamber contains from about $1\times10^5$ to about $1.5\times10^6$ tumor cells.

16. The biodiffusion chamber of claim 9, wherein a ratio of tumor cells to AS ODN in the chamber is about $5.0\times10^5$ cell: µg.

17. The biodiffusion chamber of claim 13, wherein the outer cannula comprises a side aperture, and further wherein the tumor cells are drawn into the side aperture by electronically controlled variable suction.

\* \* \* \* \*